United States Patent
Connor

(10) Patent No.: US 11,172,859 B2
(45) Date of Patent: Nov. 16, 2021

(54) WEARABLE BRAIN ACTIVITY DEVICE WITH AUDITORY INTERFACE

(71) Applicant: Robert A. Connor, St. Paul, MN (US)

(72) Inventor: Robert A. Connor, St. Paul, MN (US)

(73) Assignee: Medibotics, St. Paul, MN (US)

( * ) Notice: Subject to any disclaimer, the term of this patent is extended or adjusted under 35 U.S.C. 154(b) by 389 days.

(21) Appl. No.: 16/022,987

(22) Filed: Jun. 29, 2018

(65) Prior Publication Data

US 2018/0310855 A1   Nov. 1, 2018

Related U.S. Application Data

(63) Continuation-in-part of application No. 15/136,948, filed on Apr. 24, 2016, which is a continuation-in-part of application No. 14/599,522, filed on Jan. 18, 2015, now Pat. No. 9,814,426.

(60) Provisional application No. 61/932,517, filed on Jan. 28, 2014.

(51) Int. Cl.
  *A61B 5/291*  (2021.01)
  *A61B 5/00*   (2006.01)
  *A61B 5/375*  (2021.01)

(52) U.S. Cl.
  CPC ............. *A61B 5/291* (2021.01); *A61B 5/375* (2021.01); *A61B 5/6803* (2013.01); *A61B 5/6814* (2013.01); *A61B 5/7405* (2013.01); *A61B 5/7203* (2013.01); *A61B 5/725* (2013.01); *A61B 5/7257* (2013.01); *A61B 5/7267* (2013.01)

(58) Field of Classification Search
  CPC ... A61B 5/0478; A61B 5/6803; A61B 5/0482; A61B 5/7405; A61B 5/6814; A61B 5/7203; A61B 5/7267; A61B 5/725; A61B 5/7257; A61B 5/291; A61B 5/369; A61B 2018/00839
  See application file for complete search history.

(56) References Cited

U.S. PATENT DOCUMENTS

| | | |
|---|---|---|
| 3,998,213 A | 12/1976 | Price |
| 4,697,598 A | 10/1987 | Bernard et al. |
| 4,709,702 A | 12/1987 | Sherwin |
| 4,770,180 A | 9/1988 | Schmidt et al. |
| 4,836,219 A | 6/1989 | Hobson et al. |
| 4,967,038 A | 10/1990 | Gevins et al. |
| 5,038,782 A | 8/1991 | Gevins et al. |
| 5,293,867 A | 3/1994 | Oommen |
| 5,479,934 A | 1/1996 | Imran |
| 5,740,812 A | 4/1998 | Cowan |
| 5,800,351 A | 9/1998 | Mann |
| 5,954,667 A | 9/1999 | Finkenzeller et al. |
| 6,001,065 A | 12/1999 | Devito |
| 6,067,464 A | 5/2000 | Musha |
| 6,154,669 A | 11/2000 | Hunter et al. |
| 6,161,030 A | 12/2000 | Levendowski et al. |

(Continued)

*Primary Examiner* — Jacqueline Cheng
*Assistant Examiner* — Tho Q Tran

(57) ABSTRACT

This invention is a wearable brain activity device with electrodes held on a person's head by a frame comprising a ring portion which encircles the person's head and an arc portion which loops over the top of the person's head. Data from the electrodes is used to analyze the person's brain activity within a frequency band of 0.5-4 Hz. The device includes a speaker or vibrating member which is used to help to guide the person's brain activity from a first pattern to a second pattern.

9 Claims, 8 Drawing Sheets

(56) References Cited

U.S. PATENT DOCUMENTS

| | | | |
|---|---|---|---|
| 6,167,298 | A | 12/2000 | Levin |
| 6,171,258 | B1 | 1/2001 | Karakasoglu et al. |
| 6,254,536 | B1 | 7/2001 | Devito |
| 6,381,481 | B1 | 4/2002 | Levendowski et al. |
| 6,488,617 | B1 | 12/2002 | Katz |
| 6,574,513 | B1 | 6/2003 | Collura et al. |
| 6,811,538 | B2 | 11/2004 | Westbrook et al. |
| 7,158,822 | B2 | 1/2007 | Payne, Jr. |
| 7,297,119 | B2 | 11/2007 | Westbrook et al. |
| 7,344,244 | B2 | 3/2008 | Goodall et al. |
| D565,735 | S | 4/2008 | Washbon |
| 7,390,088 | B2 | 6/2008 | Goodall et al. |
| 7,551,952 | B2 | 6/2009 | Gevins et al. |
| 7,689,274 | B2 | 3/2010 | Mullen et al. |
| 7,885,706 | B2 | 2/2011 | Ludvig et al. |
| 8,103,328 | B2 | 1/2012 | Turner et al. |
| 8,244,342 | B2 | 8/2012 | Goodall et al. |
| 8,271,075 | B2 | 9/2012 | Chuang et al. |
| 8,301,218 | B2 | 10/2012 | Nguyen et al. |
| 8,346,354 | B2 | 1/2013 | Hyde et al. |
| 8,355,769 | B2 | 1/2013 | Levendowski et al. |
| 8,392,250 | B2 | 3/2013 | Pradeep et al. |
| 8,392,251 | B2 | 3/2013 | Pradeep et al. |
| 8,396,744 | B2 | 3/2013 | Pradeep et al. |
| 8,463,354 | B2 | 6/2013 | Fadem |
| 8,467,133 | B2 | 6/2013 | Miller |
| 8,472,120 | B2 | 6/2013 | Border et al. |
| 8,477,425 | B2 | 7/2013 | Border et al. |
| 8,482,859 | B2 | 7/2013 | Border et al. |
| 8,488,246 | B2 | 7/2013 | Border et al. |
| 8,548,852 | B2 | 10/2013 | Pradeep et al. |
| 8,562,540 | B2 | 10/2013 | Goodall et al. |
| 8,639,313 | B2 | 1/2014 | Westbrook et al. |
| 8,655,428 | B2 | 2/2014 | Pradeep et al. |
| 8,812,075 | B2 | 8/2014 | Nguyen et al. |
| 2001/0056225 | A1 | 12/2001 | DeVito |
| 2002/0029005 | A1 | 3/2002 | Levendowski et al. |
| 2002/0165462 | A1 | 11/2002 | Westbrook et al. |
| 2002/0188216 | A1 | 12/2002 | Kayyali et al. |
| 2003/0018278 | A1 | 1/2003 | Jordan |
| 2004/0267152 | A1 | 12/2004 | Pineda |
| 2005/0027207 | A1 | 2/2005 | Westbrook et al. |
| 2005/0277821 | A1 | 12/2005 | Payne |
| 2006/0252978 | A1 | 11/2006 | Vesely et al. |
| 2006/0252979 | A1 | 11/2006 | Vesely et al. |
| 2007/0010757 | A1 | 1/2007 | Goodall et al. |
| 2007/0019279 | A1 | 1/2007 | Goodall et al. |
| 2007/0032737 | A1* | 2/2007 | Causevic .............. A61B 5/411 600/544 |
| 2007/0093706 | A1 | 4/2007 | Gevins et al. |
| 2007/0106145 | A1 | 5/2007 | Kim et al. |
| 2007/0106169 | A1 | 5/2007 | Fadem |
| 2007/0112262 | A1 | 5/2007 | Payne |
| 2007/0191727 | A1 | 8/2007 | Fadem |
| 2007/0225585 | A1 | 9/2007 | Washbon et al. |
| 2007/0238945 | A1 | 10/2007 | Delic et al. |
| 2007/0249952 | A1 | 10/2007 | Rubin et al. |
| 2008/0013747 | A1* | 1/2008 | Tran .................... A61B 7/04 381/67 |
| 2008/0082019 | A1 | 4/2008 | Ludving et al. |
| 2008/0161673 | A1 | 7/2008 | Goodall et al. |
| 2008/0177197 | A1 | 7/2008 | Lee et al. |
| 2008/0208072 | A1 | 8/2008 | Fadem et al. |
| 2009/0088619 | A1 | 4/2009 | Turner et al. |
| 2009/0105576 | A1 | 4/2009 | Do et al. |
| 2009/0124920 | A1* | 5/2009 | Patterson ............ A61B 5/0482 600/544 |
| 2009/0281446 | A2 | 11/2009 | Ludvig et al. |
| 2010/0099954 | A1 | 4/2010 | Dickinson et al. |
| 2010/0125190 | A1 | 5/2010 | Fadem |
| 2010/0240982 | A1 | 9/2010 | Westbrook et al. |
| 2011/0015503 | A1 | 1/2011 | Joffe et al. |
| 2011/0028798 | A1 | 2/2011 | Hyde et al. |
| 2011/0029038 | A1 | 2/2011 | Hyde et al. |
| 2011/0029044 | A1 | 2/2011 | Hyde et al. |
| 2011/0098593 | A1 | 4/2011 | Low et al. |
| 2011/0221656 | A1 | 9/2011 | Haddick et al. |
| 2011/0221669 | A1 | 9/2011 | Shams et al. |
| 2011/0221672 | A1 | 9/2011 | Osterhout et al. |
| 2011/0222745 | A1 | 9/2011 | Osterhout et al. |
| 2011/0227820 | A1 | 9/2011 | Haddick et al. |
| 2011/0237971 | A1 | 9/2011 | Pradeep et al. |
| 2011/0270117 | A1 | 11/2011 | Warwick et al. |
| 2011/0282231 | A1 | 11/2011 | Pradeep et al. |
| 2011/0282232 | A1 | 11/2011 | Pradeep et al. |
| 2012/0029379 | A1 | 2/2012 | Sivadas |
| 2012/0062445 | A1 | 3/2012 | Haddick et al. |
| 2012/0072289 | A1 | 3/2012 | Pradeep et al. |
| 2012/0075168 | A1 | 3/2012 | Osterhout et al. |
| 2012/0150545 | A1 | 6/2012 | Simon |
| 2012/0212398 | A1 | 8/2012 | Border et al. |
| 2012/0212400 | A1 | 8/2012 | Border et al. |
| 2012/0218172 | A1 | 8/2012 | Border et al. |
| 2012/0218301 | A1 | 8/2012 | Miller |
| 2012/0226127 | A1 | 9/2012 | Asjes et al. |
| 2012/0235883 | A1 | 9/2012 | Border et al. |
| 2012/0235886 | A1 | 9/2012 | Border et al. |
| 2012/0235887 | A1 | 9/2012 | Border et al. |
| 2012/0235900 | A1 | 9/2012 | Border et al. |
| 2012/0236030 | A1 | 9/2012 | Border et al. |
| 2012/0242678 | A1 | 9/2012 | Border et al. |
| 2012/0242698 | A1 | 9/2012 | Haddick et al. |
| 2012/0253220 | A1* | 10/2012 | Rai .................... A61B 5/369 600/544 |
| 2013/0046206 | A1 | 2/2013 | Preminger |
| 2013/0056010 | A1 | 3/2013 | Walker et al. |
| 2013/0060097 | A1 | 3/2013 | Rubin |
| 2013/0127708 | A1 | 5/2013 | Jung et al. |
| 2013/0127980 | A1 | 5/2013 | Haddick et al. |
| 2013/0131464 | A1 | 5/2013 | Westbrook et al. |
| 2013/0131537 | A1 | 5/2013 | Tam |
| 2013/0177883 | A1 | 7/2013 | Barnehama et al. |
| 2013/0185144 | A1 | 7/2013 | Pradeep et al. |
| 2013/0204153 | A1* | 8/2013 | Buzhardt ............ A61B 5/0476 600/544 |
| 2013/0242262 | A1 | 9/2013 | Lewis |
| 2013/0303837 | A1 | 11/2013 | Berka et al. |
| 2013/0310676 | A1 | 11/2013 | Jung |
| 2013/0314243 | A1 | 11/2013 | Le |
| 2013/0314303 | A1 | 11/2013 | Osterhout et al. |
| 2013/0317382 | A1 | 11/2013 | Le |
| 2013/0317384 | A1 | 11/2013 | Le |
| 2013/0338446 | A1 | 12/2013 | Van Vugt et al. |
| 2014/0023999 | A1 | 1/2014 | Greder |
| 2014/0267005 | A1 | 9/2014 | Urbach |
| 2014/0267401 | A1 | 9/2014 | Urbach |
| 2014/0316230 | A1 | 10/2014 | Denison et al. |
| 2014/0336473 | A1* | 11/2014 | Greco .................. A61B 5/742 600/301 |
| 2014/0347265 | A1 | 11/2014 | Aimone et al. |
| 2014/0375545 | A1 | 12/2014 | Ackerman et al. |
| 2016/0213300 | A1* | 7/2016 | Allen .................. A61B 5/6803 |

* cited by examiner

WEARABLE BRAIN ACTIVITY DEVICE WITH AUDITORY INTERFACE

CROSS-REFERENCE TO RELATED APPLICATIONS

This patent application is a continuation-in-part of U.S. patent application Ser. No. 15/136,948 with a filing date of Apr. 24, 2016 which, in turn, is a continuation-in-part of U.S. patent application Ser. No. 14/599,522 with a filing date of Jan. 18, 2015 which, in turn, claims the priority benefit of U.S. Provisional Patent Application No. 61/932,517 with a filing date of Jan. 28, 2014. The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices for monitoring and modifying electromagnetic brain activity.

Introduction

A wearable brain activity monitor has many potential applications in the fields of medicine, health and fitness, sports, and communication. Incorporation of an auditory interface into a wearable brain activity monitor further expands the range of potential applications to include biofeedback for improved mental well-being during the day and improved sleep during the night.

Review of the Relevant Art

It can be challenging trying to classify relevant art in this field into discrete categories. However, classification of relevant art into categories, even if imperfect, can be an invaluable tool for reviewing the relevant art. Towards this end, I herein identify 21 categories of relevant art and provide examples of relevant art in each category (including patent or patent application number, inventor, publication date, and title). Some examples of relevant art disclose multiple concepts and thus appear in more than one category.

The 21 categories of relevant art which are used for this review are as follows: (1) device like a skull cap with EEG/brainwave sensors; (2) device like a baseball cap with EEG/brainwave sensors; (3) device with [multiple] front-to-back arcuate members and EEG/brainwave sensors; (4) device with [multiple] side-to-side arcuate members and EEG/brainwave sensors; (5) device with multiple cross-crossing arcuate members and EEG/brainwave sensors; (6) device with multiple arms radially-extending from side and EEG/brainwave sensors; (7) device with multiple arms radially-downward from top and EEG/brainwave sensors; (8) device with multiple arms radially-forward from rear and EEG/brainwave sensors; (9) device with multiple arms radially-backward from front and EEG/brainwave sensors; (10) device with circular horizontal loop (e.g. headband style) and EEG/brainwave sensors; (11) device with top semicircular loop (e.g. headphone style) and EEG/brainwave sensors; (12) device with rear semicircular loop and EEG/brainwave sensors; (13) device with frontal semicircular loop and EEG/brainwave sensors; (14) device like eyeglasses or other eyewear with EEG/brainwave sensors; (15) device like a hearing aid or other earwear with EEG/brainwave sensors; (16) device like a breathing mask with EEG/brainwave sensors; (17) specific type of EEG/brainwave sensor; (18) adhesive EEG/brainwave sensors; (19) method for EEG/brainwave analysis; (20) device that actively emits brain-stimulating energy; and (21) miscellaneous.

1. Device Like a Skull Cap with EEG/Brainwave Sensor(s)

Devices in this category hold electromagnetic brain activity sensors in contact with (or proximity to) a person's head using a sensor-positioning member configured like a skull cap. A "skull cap" is defined herein as a wearable cap-like or hat-like member that covers most of the hair-covered portion of a person's head and flexibly conforms to the contours of the head. A skull cap is generally held snugly against the surface of the head by straps and/or elastic bands. Due to the high percentage of the surface area of the top of a person's head which is covered by such a device, such a device can be used to hold a relatively large number of electromagnetic brain activity sensors in a variety of positions across a person's head. Most of the devices in this category are relatively obtrusive and would be awkward to wear outside a medical setting. They are generally not appropriate for wearing during the activities of daily life.

Prior art which appears to be within this category includes U.S. Pat. No. 4,537,198 (Corbett, Aug. 27, 1985, "Electrode Cap"), U.S. Pat. No. 4,632,122 (Johansson, Dec. 30, 1986, "Method and Apparatus for Conducting Brain Function Diagnostic Test"), U.S. Pat. No. 4,683,892 (Johansson, Aug. 4, 1987, "Method and Apparatus for Conducting Brain Function Diagnostic Test"), U.S. Pat. No. 4,709,702 (Sherwin, Dec. 1, 1987, "Electroencephalographic Cap"), U.S. Pat. No. 4,800,888 (Itil et al., Jan. 31, 1989, "Enhanced Electrode Headset"), U.S. Pat. No. 5,038,782 (Gevins et al., Aug. 13, 1991, "Electrode System for Brain Wave Detection"), U.S. Pat. No. 5,724,987 (Gevins et al., Mar. 10, 1998, "Neurocognitive Adaptive Computer-Aided Training Method and System"), U.S. Pat. No. 6,067,464 (Musha, May 23, 200, "Electrode"), U.S. Pat. No. 8,155,736 (Sullivan et al., Apr. 10, 2012, "EEG Control of Devices Using Sensory Evoked Potentials"), and U.S. Pat. No. 8,391,966 (Luo et al., Mar. 5, 2013, "Sensory-Evoked Potential (SEP) Classification/Detection in the Time Domain").

Prior art which appears to be within this category also includes U.S. patent applications: 20070225577 (Mathan, Sep. 27, 2007, "System and Method for Providing Sensor Based Human Factors Protocol Analysis"), 20070225585 (Washbon and Delic, Sep. 27, 2007, "Headset for Electrodes"), 20070238945 (Delic et al., Oct. 11, 2007, "Electrode Headset"), 20070255127 (Mintz et al., Nov. 1, 2007, "Mobile Electroencephalograph Data Collection and Diagnosis System"), 20080275359 (Mintz et al., Nov. 6, 2008, "Mobile in Vivo Brain Scan and Analysis System"), 20100234752 (Sullivan et al., Sep. 16, 2010, "EEG Control of Devices Using Sensory Evoked Potentials"), 20110040202 (Luo et al., Feb. 17, 2011, "Sensory-Evoked Potential (SEP) Classification/Detection in the Time Domain"), 20110298706 (Mann, Dec. 8, 2011, "Brainwave Actuated Apparatus"), and 20120059273 (Meggiolaro et al., Mar. 8, 2012, "Process and Device for Brain Computer Interface").

Prior art which appears to be within this category also includes U.S. patent applications: 20120136273 (Michelson Jr., May 31, 2012, "Apparatus and Method for Monitoring and Analyzing Brainwaves"), 20120220889 (Sullivan et al., Aug. 30, 2012, "EEG Control of Devices Using Sensory Evoked Potentials"), 20120289869 (Tyler, Nov. 15, 2012, "Devices and Methods for Modulating Brain Activity"), 20130211276 (Luo et al., Aug. 15, 2013, "Sensory-Evoked Potential (SEP) Classification/Detection in the Time Domain"), 20130281759 (Hagedorn et al., Oct. 24, 2013, "Transcranial Stimulation Device and Method Based on Electrophysiological Testing"), 20140163408 (Kocher, Jun. 12, 2014, "System for Analyzing Mental and Behavioral Correlations"), and 20140288614 (Hagedorn et al., Sep. 25, 2014, "Electrophysiology Measurement and Training and Remote Databased and Data Analysis Measurement Method and System").

2. Device Like a Baseball Cap with EEG/Brainwave Sensor(s)

Devices in this category hold electromagnetic brain activity sensors in contact with (or proximity to) a person's head using a sensor-positioning member configured like a baseball cap. A "baseball cap" is defined herein as a wearable member with a generally-hemispherical portion which fits over the top of a person's head and an attached visor which extends outward from the person's forehead. Sometimes arcuate bands are embedded in the cap in circular-around-the-head, side-to-side-over-the-top, and/or front-to-back-over-the-top configurations. Devices in this category generally do not cover as much of the surface of the head and may not fit as tightly against the surface of the head as skull cap devices. On the plus side, devices in this category are generally less obtrusive than skull cap devices. However, there are still many circumstances and settings wherein wearing a baseball cap is inappropriate.

Prior art which appears to be within this category includes U.S. Pat. No. 4,697,598 (Bernard et al., Oct. 6, 1987, "Evoked Potential Autorefractometry System"), U.S. Pat. No. 4,709,702 (Sherwin, Dec. 1, 1987, "Electroencephalographic Cap"), U.S. Pat. No. 6,161,030 (Levendowski et al., Dec. 12, 2000, "Portable EEG Electrode Locator Headgear"), U.S. Pat. No. 6,381,481 (Levendowski et al., Apr. 30, 2002, "Portable EEG Electrode Locator Headgear"), U.S. Pat. No. 6,574,513 (Collura et al., Jun. 3, 2003, "EEG Electrode Assemblies"), U.S. Pat. No. 6,640,122 (Manoli et al., Oct. 28, 2003, "EEG Electrode and EEG Electrode Locator Assembly"), and U.S. Pat. No. 7,204,250 (Burton, Apr. 17, 2007, "Bio-Mask"), U.S. Pat. No. 8,281,787 (Burton, Oct. 9, 2012, "Bio-Mask with Integral Sensors").

Prior art which appears to be within this category also includes U.S. patent applications: 20020029005 (Levendowski et al., Mar. 7, 2002, "Portable EEG Electrode Locator Headgear"), 20040073129 (Caldwell et al., Apr. 15, 2004, "EEG System for Time-Scaling Presentations"), 20040163648 (Burton, Aug. 26, 2004, "Bio-Mask with Integral Sensors"), 20100147304 (Burton, Jun. 17, 2010, "Bio-Mask with Integral Sensors"), 20110015503 (Joffe et al., Jan. 20, 2011, "Medical Apparatus for Collecting Patient Electroencephalogram (EEG) Data"), 20110046502 (Pradeep et al., Feb. 24, 2011, "Distributed Neuro-Response Data Collection and Analysis"), 20110046504 (Pradeep et al., Feb. 24, 2011, "Distributed Neuro-Response Data Collection and Analysis"), and 20110270117 (Warwick et al., Nov. 3, 2011, "Remote Continuous Seizure Monitor and Alarm").

3. Device with [Multiple] Front-to-Back Arcuate Member(s) and EEG/Brainwave Sensor(s)

Devices in this category hold electromagnetic brain activity sensors in contact with (or proximity to) a person's head using (multiple) arcing member(s) which span a person's head from front-to-back (or vice versa). Devices in this category can look similar to some types of bicycle helmets with front-to-back arcuate members. In an example, the front-to-back arcing members can converge at the forehead and at the rear of the head. In an example, a device in this category can comprise: a first arcuate member which encircles a person's head: a second arcuate member which loops front-to-back over the top of the head; and third and fourth arcuate members which loop front-to-back over the sides of the head between the first and second members. Devices in this category can hold a relatively large number of electromagnetic brain activity sensors along arcuate front-to-rear lines on a person's head. However, such devices tend to be too obtrusive to wear during the activities of daily life.

Prior art which appears to be within this category includes U.S. Pat. No. 3,998,213 (Price, Dec. 21, 1976, "Self-Adjustable Holder for Automatically Positioning Electroencephalographic Electrodes"), U.S. Pat. No. 8,355,769 (Levendowski et al., Jan. 15, 2013, "System for the Assessment of Sleep Quality in Adults and Children"), U.S. Pat. No. 8,463,354 (Fadem, Jun. 11, 2013, "Electrode System with Rigid-Flex Circuit"), U.S. Pat. No. 8,639,313 (Westbrook et al, Jan. 28, 2014, "System for the Assessment of Sleep Quality in Adults and Children"); and U.S. patent applications 20100125190 (Fadem, May 20, 2010, "Electrode System"), 20100240982 (Westbrook et al., Sep. 23, 2010, "System for the Assessment of Sleep Quality in Adults and Children"), and 20130131464 (Westbrook et al., May 23, 2013, "System for the Assessment of Sleep Quality in Adults and Children").

4. Device with [Multiple] Side-to-Side Arcuate Member(s) and EEG/Brainwave Sensor(s)

Devices in this category hold electromagnetic brain activity sensors in contact with (or proximity to) a person's head using (multiple) arcing member(s) which span a person's head from side to side. In an example, side-to-side arcing members can converge near, or over, the person's ears. In an example, devices in this category can be similar to those in the previous category, except having been rotated 90 degrees so that the arcuate members converge on the sides of the person's head rather than the front and rear of the person's head. Devices in this category can hold a relatively large number of electromagnetic brain activity sensors along arcuate side-to-side lines on a person's head. However, such devices tend to be too obtrusive to wear during the activities of daily life.

Prior art which appears to be within this category includes U.S. Pat. No. 4,836,219 (Hobson et al., Jun. 6, 1989, "Electronic Sleep Monitor Headgear"), U.S. Pat. No. 5,800,351 (Mann, Sep. 1, 1998, "Electrode Supporting Head Set"), U.S. Pat. No. 6,574,513 (Collura et al., Jun. 3, 2003, "EEG Electrode Assemblies"), U.S. Pat. No. 7,158,822 (Payne Jr., Jan. 2, 2007, "Electrode Holder, Headwear, and Wire Jacket Adapted for Use in Sleep Apnea Testing"), and U.S. Pat. No. 7,885,706 (Ludvig et al., Feb. 8, 2011, "System and Device for Seizure Detection").

Prior art which appears to be within this category also includes U.S. patent applications: 20030018278 (Jordan, Jan. 23, 2003, "Electroencephalogram Acquisition Unit and System"), 20050277821 (Payne, Dec. 15, 2005, "Electrode Holder, Headwear, and Wire Jacket Adapted for Use in Sleep Apnea Testing"), 20070112262 (Payne, May 17, 2007, "Electrode Holder, Headwear, and Wire Jacket Adapted for Use in Sleep Apnea Testing"), 20080082019 (Ludving et al., Apr. 3, 2008, "System and Device for Seizure Detection"), 20090281446 (Ludvig et al., Nov. 12, 2009, "System and Device for Seizure Detection"), 20110015503 (Joffe et al., Jan. 20, 2011, "Medical Apparatus for Collecting Patient Electroencephalogram (EEG) Data"), and 20110270117 (Warwick et al., Nov. 3, 2011, "Remote Continuous Seizure Monitor and Alarm").

5. Device with Multiple Cross-Crossing Arcuate Members and EEG/Brainwave Sensor(s)

Devices in this category hold electromagnetic brain activity sensors in contact with (or proximity to) a person's head using multiple arcing members which span a person's head from front-to-rear and also multiple arcing members which span a person's head from side-to-side. In an example, the front-to-rear arcuate members and the side-to-side arcuate members can form a criss-cross pattern on the person's head. Devices in this category can hold a relatively large number of electromagnetic brain activity sensors on a person's head. However, such devices tend to be too obtrusive to wear during the activities of daily life.

Prior art which appears to be within this category includes U.S. Pat. No. 3,998,213 (Price, Dec. 21, 1976, "Self-Adjustable Holder for Automatically Positioning Electroencephalographic Electrodes"), U.S. Pat. No. 5,293,867 (Oommen, Mar. 15, 1994, "Method and Apparatus for Marking Electrode Locations for Electroencephalographic Procedure"), U.S. Pat. No. 5,479,934 (Imran, Jan. 2, 1996, "EEG Headpiece with Disposable Electrodes and Apparatus and System and Method for Use Therewith"), U.S. Pat. No. 6,488,617 (Katz, Dec. 3, 2002, "Method and Device for Producing a Desired Brain State"), U.S. Pat. No. 8,463,354 (Fadem, Jun. 11, 2013, "Electrode System with Rigid-Flex Circuit"); and U.S. patent applications 20030018278 (Jordan, Jan. 23, 2003, "Electroencephalogram Acquisition Unit and System"), and 20100125190 (Fadem, May 20, 2010, "Electrode System").

6. Device with Multiple Arms Radially-Extending from Side and EEG/Brainwave Sensor(s)

Devices in this category hold electromagnetic brain activity sensors in contact with (or proximity to) a person's head using multiple sensor-holding protrusions, fingers, or arms which extend radially outward from a central position on one side (or from central positions on both sides) of a person's head. In an example, such devices can include bilateral clusters (one on each side of the head) of radially-extending protrusions, fingers, or arms. In an example, radially-extending protrusions, fingers, or arms can curve around the head toward the front, top, and/or rear portions of the head. To use colorful language, some such devices can look like a wearer has one or two starfish (or even octopi) clinging to the sides of their head. Such devices can be less obtrusive than those in the preceding categories (especially when they do not span the forehead or the top of the head), but can still attract attention if worn during the activities of daily life.

Prior art which appears to be within this category includes U.S. Pat. No. 5,954,667 (Finkenzeller et al., Sep. 21, 1999, "Device for Deriving Acoustically Evoked Brain Potentials"), U.S. Pat. No. 8,271,075 (Chuang et al., Sep. 18, 2012, "Audio Headset with Bio-Signal Sensors"), U.S. Pat. No. 8,392,250 (Pradeep et al., Mar. 5, 2013, "Neuro-Response Evaluated Stimulus in Virtual Reality Environments"), U.S. Pat. No. 8,392,251 (Pradeep et al., Mar. 5, 2013, "Location Aware Presentation of Stimulus Material"), U.S. Pat. No. 8,396,744 (Pradeep et al., Mar. 12, 2013, "Effective Virtual Reality Environments for Presentation of Marketing Materials"), U.S. Pat. No. 8,548,852 (Pradeep et al., Oct. 1, 2013, "Effective Virtual Reality Environments for Presentation of Marketing Materials"), and U.S. Pat. No. 8,655,428 (Pradeep et al., Feb. 18, 2014, "Neuro-Response Data Synchronization").

Prior art which appears to be within this category also includes U.S. patent applications: 20070106169 (Fadem, May 10, 2007, "Method and System for an Automated E.E.G. System for Auditory Evoked Responses"), 20070191727 (Fadem, Aug. 16, 2007, "Evoked Response Testing System for Neurological Disorders"), 20070225585 (Washbon and Delic, Sep. 27, 2007, "Headset for Electrodes"), 20070238945 (Delic et al., Oct. 11, 2007, "Electrode Headset"), 20080208072 (Fadem et al., Aug. 28, 2008, "Biopotential Waveform Data Fusion Analysis and Classification Method"), 20110237971 (Pradeep et al., Sep. 29, 2011, "Discrete Choice Modeling Using Neuro-Response Data"), and 20110282231 (Pradeep et al., Nov. 17, 2011, "Mechanisms for Collecting Electroencephalography Data").

Prior art which appears to be within this category also includes U.S. patent applications: 20110282232 (Pradeep et al., Nov. 17, 2011, "Neuro-Response Data Synchronization"), 20120072289 (Pradeep et al., Mar. 22, 2012, "Biometric Aware Content Presentation"), 20130131537 (Tam, May 23, 2013, "Tong Ren Brainwave Entrainment"), 20130185144 (Pradeep et al., Jul. 18, 2013, "Systems and Methods for Analyzing Neuro-Reponse Data and Virtual Reality Environments"), 20130314243 (Le, Nov. 28, 2013, "System and Method for Enabling Collaborative Analysis of a Biosignal"), 20130317382 (Le, Nov. 28, 2013, "System and Method for Providing and Aggregating Biosignals and Action Data"), and 20130317384 (Le, Nov. 28, 2013, "System and Method for Instructing a Behavior Change in a User").

7. Device with Multiple Arms Radially-Downward from Top and EEG/Brainwave Sensor(s)

Devices in this category hold electromagnetic brain activity sensors in contact with (or proximity to) a person's head using multiple sensor-holding protrusions, fingers, or arms which extend radially downward from a position on the top of a person's head. In an example, radially-extending protrusions, fingers, or arms can curve around the head toward the front, sides, and/or rear portions of the head. To use the colorful language from the previous category, now a figurative starfish (or octopus) is clinging to the top of the person's head. Such devices can be less obtrusive than some of those in the preceding categories, but can still attract attention if worn during the activities of daily life.

Prior art which appears to be within this category includes U.S. Pat. No. 6,067,464 (Musha, May 23, 200, "Electrode"), U.S. Pat. No. 6,154,669 (Hunter et al., Nov. 28, 2000, "Headset for EEG Measurements"), U.S. Pat. No. 6,161,030 (Levendowski et al., Dec. 12, 2000, "Portable EEG Electrode Locator Headgear"), U.S. Pat. No. 6,381,481 (Levendowski et al., Apr. 30, 2002, "Portable EEG Electrode Locator Headgear"), U.S. Pat. No. 7,551,952 (Gevins et al., Jun. 23, 2009, "EEG Electrode Headset"), U.S. Pat. No. 8,103,328 (Turner et al., Jan. 24, 2012, "Self-Locating Sensor Mounting Apparatus"), U.S. Pat. No. 8,392,250 (Pradeep et al., Mar. 5, 2013, "Neuro-Response Evaluated Stimulus in Virtual Reality Environments"), U.S. Pat. No. 8,392,251 (Pradeep et al., Mar. 5, 2013, "Location Aware Presentation of Stimulus Material"), U.S. Pat. No. 8,396,744 (Pradeep et al., Mar. 12, 2013, "Effective Virtual Reality Environments for Presentation of Marketing Materials"), U.S. Pat. No. 8,548,852 (Pradeep et al., Oct. 1, 2013, "Effective Virtual Reality Environments for Presentation of Marketing Materials"), and U.S. Pat. No. 8,655,428 (Pradeep et al., Feb. 18, 2014, "Neuro-Response Data Synchronization").

Prior art which appears to be within this category also includes U.S. patent applications: 20020029005 (Levendowski et al., Mar. 7, 2002, "Portable EEG Electrode Locator Headgear"), 20070093706 (Gevins et al., Apr. 26, 2007, "EEG Electrode Headset"), 20090088619 (Turner et al., Apr. 2, 2009, "Self-Locating Sensor Mounting Apparatus"), 20110098593 (Low et al., Apr. 28, 2011, "Head Harness & Wireless EEG Monitoring System"), 20110237971 (Pradeep et al., Sep. 29, 2011, "Discrete Choice Modeling Using Neuro-Response Data"), 20110282231 (Pradeep et al., Nov. 17, 2011, "Mechanisms for Collecting Electroencephalography Data"), 20110282232 (Pradeep et al., Nov. 17, 2011, "Neuro-Response Data Synchronization"), 20120072289 (Pradeep et al., Mar. 22, 2012, "Biometric Aware Content Presentation"), and 20130185144 (Pradeep et al., Jul. 18, 2013, "Systems and Methods for Analyzing Neuro-Reponse Data and Virtual Reality Environments").

8. Device with Multiple Arms Radially-Forward from Rear and EEG/Brainwave Sensor(s)

Devices in this category hold electromagnetic brain activity sensors in contact with (or proximity to) a person's head using multiple sensor-holding protrusions, fingers, or arms which extend radially forward from a central position at the rear of a person's head. In an example, radially-extending protrusions, fingers, or arms can curve around the head toward the top and sides of the head. To use the colorful language from the previous category, now a figurative starfish (or octopus) is clinging to the back of the person's head. Such devices can be less obtrusive than some of those in the preceding categories, but can still attract attention if worn during the activities of daily life.

Prior art which appears to be within this category includes U.S. Pat. No. 4,770,180 (Schmidt et al., Sep. 13, 1988, "Electroencephalographic Head Set with a Disposable Monitor"), U.S. Pat. No. 4,967,038 (Gevins et al., Oct. 30, 1990, "Dry Electrode Brain Wave Recording System"), U.S. Pat. No. 5,038,782 (Gevins et al., Aug. 13, 1991, "Electrode System for Brain Wave Detection"), and D565735 (Washbon, Apr. 1, 2008, "Electrode Headset"); and U.S. patent applications 20070225585 (Washbon and Delic, Sep. 27, 2007, "Headset for Electrodes"), 20070238945 (Delic et al., Oct. 11, 2007, "Electrode Headset"), 20090105576 (Do et al., Apr. 23, 2009, "Electrode Conductive Element"), 20120029379 (Sivadas, Feb. 2, 2012, "Mind Strength Trainer"), and 20130046206 (Preminger, Feb. 21, 2013, "System and Method for Neurocognitive Training and/or Neuropsychological Assessment").

9. Device with Multiple Arms Radially-Backward from Front and EEG/Brainwave Sensor(s)

Devices in this category hold electromagnetic brain activity sensors in contact with (or proximity to) a person's head using multiple sensor-holding protrusions, fingers, or arms which extend radially backward from a position on the front of a person's head (such as the forehead). In an example, radially-extending protrusions, fingers, or arms can curve around the head toward the top and sides of the head. Such devices can be obtrusive and attract attention, especially if worn to a showing of the movie "Aliens". Prior art which appears to be within this category includes U.S. patent application 20020188216 (Kayyali et al., Dec. 12, 2002, "Head Mounted Medical Device").

10. Device with Circular Horizontal Loop (e.g. Headband Style) and EEG/Brainwave Sensor(s)

Devices in this category hold electromagnetic brain activity sensors in contact with (or proximity to) a person's head using a sensor-positioning member which is configured like a headband, ring, or other generally-circular member which encircles a person's head in (or close to) a horizontal plane when the person is upright. In an example, such a device can span a portion of a person's forehead as it encircles the person's head. Since devices in this category can span a portion of the forehead, such devices can be used with sensors which require contact with (or proximity to) portions of the head which do not have hair. Such devices can be appropriate for wearing while running or doing other types of exercise, but there are still many settings wherein wearing a headband or head-encircling ring is generally not appropriate.

Prior art which appears to be within this category includes U.S. Pat. No. 6,001,065 (Devito, Dec. 14, 1999, "Method and Apparatus for Measuring and Analyzing Physiological Signals for Active or Passive Control of Physical and Virtual Spaces and the Contents Therein"), U.S. Pat. No. 6,171,258 (Karakasoglu et al., Jan. 9, 2001, "Multi-Channel Self-Contained Apparatus and Method for Diagnosis of Sleep Disorders"), U.S. Pat. No. 6,254,536 (Devito, Jul. 3, 2001, "Method and Apparatus for Measuring and Analyzing Physiological Signals for Active or Passive Control of Physical and Virtual Spaces and the Contents Therein"), U.S. Pat. No. 6,811,538 (Westbrook et al., Nov. 2, 2004, "Sleep Apnea Risk Evaluation"), U.S. Pat. No. 7,297,119 (Westbrook et al., Nov. 20, 2007, "Sleep Apnea Risk Evaluation"), and U.S. Pat. No. 7,885,706 (Ludvig et al., Feb. 8, 2011, "System and Device for Seizure Detection").

Prior art which appears to be within this category also includes U.S. patent applications: 20010056225 (DeVito, Dec. 27, 2001, "Method and Apparatus for Measuring and Analyzing Physiological Signals for Active or Passive Control of Physical and Virtual Spaces and the Contents Therein"), 20020165462 (Westbrook et al., Nov. 7, 2002, "Sleep Apnea Risk Evaluation"), 20020188216 (Kayyali et al., Dec. 12, 2002, "Head Mounted Medical Device"), 20040267152 (Pineda, Dec. 20, 2004, "Method and System for Predicting and Preventing Seizures"), 20050027207 (Westbrook et al., Feb. 3, 2005, "Sleep Apnea Risk Evaluation"), and 20070249952 (Rubin et al., Oct. 25, 2007, "Systems and Methods for Sleep Monitoring").

Prior art which appears to be within this category also includes U.S. patent applications: 20080082019 (Ludving et al., Apr. 3, 2008, "System and Device for Seizure Detection"), 20090281446 (Ludvig et al., Nov. 12, 2009, "System and Device for Seizure Detection"), 20100099954 (Dickinson et al., Apr. 22, 2010, "Data-Driven Sleep Coaching System"), 20120150545 (Simon, Jun. 14, 2012, "Brain-Computer Interface Test Battery for the Physiological Assessment of Nervous System Health"), 20130060097 (Rubin, Mar. 7, 2013, "Multi-Modal Sleep System"), 20130127708 (Jung et al., May 23, 2013, "Cell-Phone Based Wireless and Mobile Brain-Machine Interface"), and 20130338446 (Van Vugt et al., Dec. 19, 2013, "Sleep Disturbance Monitoring Apparatus").

11. Device with Top Semicircular Loop (e.g. Headphone Style) and EEG/Brainwave Sensor(s)

Devices in this category hold electromagnetic brain activity sensors in contact with (or proximity to) a person's head using a (semicircular) arcuate member which looks like a set of headphones, hair band, or tiara. In an example, such a device can loop over the top of a person's head, from one side to the other side. In an example, such a device can loop over the top of a person's head from one ear to the other ear.

In example, such a device can not only look like a set of headphones, but can actually be a set of headphones, wherein these headphones also include one or more electromagnetic brain activity sensors. Wearing a set of headphones or a hair band is more common (and thus may attract less attention) than wearing most of the devices discussed in preceding categories, but there are still many settings wherein wearing such a device would attract attention and be inappropriate.

Prior art which appears to be within this category includes U.S. Pat. No. 4,697,598 (Bernard et al., Oct. 6, 1987, "Evoked Potential Autorefractometry System"), U.S. Pat. No. 4,709,702 (Sherwin, Dec. 1, 1987, "Electroencephalographic Cap"), U.S. Pat. No. 5,740,812 (Cowan, Apr. 21, 1998, "Apparatus for and Method of Providing Brainwave Biofeedback"), U.S. Pat. No. 6,154,669 (Hunter et al., Nov. 28, 2000, "Headset for EEG Measurements"), U.S. Pat. No. 6,167,298 (Levin, Dec. 26, 2000, "Devices and Methods for Maintaining an Alert State of Consciousness Through Brain Wave Monitoring"), U.S. Pat. No. 7,689,274 (Mullen et al., Mar. 30, 2010, "Brain-Wave Aware Sleep Management"), U.S. Pat. No. 8,271,075 (Chuang et al., Sep. 18, 2012, "Audio Headset with Bio-Signal Sensors"), and U.S. Pat. No. 8,301,218 (Nguyen et al., Oct. 30, 2012, "Contoured Electrode"), U.S. Pat. No. 8,812,075 (Nguyen et al., Aug. 19, 2014, "Contoured Electrode").

Prior art which appears to be within this category also includes U.S. patent applications: 20120029379 (Sivadas, Feb. 2, 2012, "Mind Strength Trainer"), 20120226127 (Asjes et al., Sep. 6, 2012, "Device for Positioning Electrodes on a User's Scalp"), 20130177883 (Barnehama et al., Jul. 11, 2013, "Systems and Methods for Directing Brain Activity"), and 20130310676 (Jung, Nov. 21, 2013, "EEG Hair Band").

12. Device with Rear Semicircular Loop and EEG/Brainwave Sensor(s)

Devices in this category hold electromagnetic brain activity sensors in contact with (or proximity to) a person's head using a (semicircular) arcuate member which loops around the rear portion of a person's head, from one side to the other side. In an example, such a device can loop around the rear portion of a person's head from one ear to the other ear. Such a device can be less obtrusive than many of the devices in preceding categories because it does not span the top of the head or face, but it is not well-suited for use with sensors which require contact with skin without hair. Prior art which appears to be within this category includes U.S. patent application 20140316230 (Denison et al., Oct. 23, 2014, "Methods and Devices for Brain Activity Monitoring Supporting Mental State Development and Training").

13. Device with Frontal Semicircular Loop and EEG/Brainwave Sensor(s)

Devices in this category hold electromagnetic brain activity sensors in contact with (or proximity to) a person's head using a (semicircular) arcuate member which loops around the front of a person's head, from one side to the other side. In an example, such a device can loop around the front of a person's head from one ear to the other ear. In an example, such a device can span a person's forehead. Such a device can be well-suited for use with sensors which require contact with skin without hair, but can be somewhat obtrusive since it spans a portion of a person's face. Prior art which appears to be within this category includes U.S. patent application 20080177197 (Lee et al., Jul. 24, 2008, "Method and Apparatus for Quantitatively Evaluating Mental States Based on Brain Wave Signal Processing System").

14. Device Like Eyeglasses or Other Eyewear with EEG/Brainwave Sensor(s)

Devices in this category hold electromagnetic brain activity sensors in contact with (or proximity to) a person's head using a sensor-positioning member which looks like a pair of eyeglasses, goggles, or other eyewear. In an example, such a device can span from one ear, to the face, across the face (over the bridge of the nose), and then to the other ear. In example, such a device can not only look like a pair of eyeglasses, but can actually be a pair of eyeglasses, wherein these eyeglasses include one or more electromagnetic brain activity sensors. Some of the art in this category predominantly focuses on the optical aspects of a pair of eyeglasses, with only tangential mention of a possible EEG sensor, but such art is included in this category for the sake of completeness. Wearing a pair of eyeglasses is very common and thus attracts less attention than virtually all of the devices discussed in preceding categories. However, conventional eyeglass frames (especially those with straight side pieces) do not contact a person's temple or forehead. Accordingly, conventional eyeglass frame configurations are not ideally-suited for holding one or more electromagnetic brain activity sensors in contact with a person's temple and/or forehead.

Prior art which appears to be within this category includes U.S. Pat. No. 7,344,244 (Goodall et al., Mar. 18, 2008, "Adjustable Lens System with Neural-Based Control"), U.S. Pat. No. 7,390,088 (Goodall et al., Jun. 24, 2008, "Adjustable Lens System with Neural-Based Control"), U.S. Pat. No. 7,486,988 (Goodall et al., Feb. 3, 2009, "Method and System for Adaptive Vision Modification"), U.S. Pat. No. 8,244,342 (Goodall et al., Aug. 14, 2012, "Method and System for Adaptive Vision Modification"), U.S. Pat. No. 8,346,354 (Hyde et al., Jan. 1, 2013, "Determining a Neuromodulation Treatment Regimen in Response to Contactlessly Acquired Information"), U.S. Pat. No. 8,467,133 (Miller, Jun. 18, 2013, "See-Through Display with an Optical Assembly Including a Wedge-Shaped Illumination System"), U.S. Pat. No. 8,472,120 (Border et al., Jun. 25, 2013, "See-Through Near-Eye Display Glasses with a Small Scale Image Source"), U.S. Pat. No. 8,477,425 (Border et al., Jul. 2, 2013, "See-Through Near-Eye Display Glasses Including a Partially Reflective, Partially Transmitting Optical Element"), U.S. Pat. No. 8,482,859 (Border et al., Jul. 9, 2013, "See-Through Near-Eye Display Glasses Wherein Image Light Is Transmitted to and Reflected From an Optically Flat Film"), U.S. Pat. No. 8,488,246 (Border et al., Jul. 16, 2013, "See-Through Near-Eye Display Glasses Including a Curved Polarizing Film in the Image Source, a Partially Reflective, Partially Transmitting Optical Element and an Optically Flat Film"), and U.S. Pat. No. 8,562,540 (Goodall et al., Oct. 22, 2013, "Method and System for Adaptive Vision Modification").

Prior art which appears to be within this category also includes U.S. patent applications: 20060252978 (Vesely et al., Nov. 9, 2006, "Biofeedback Eyewear System"), 20060252979 (Vesely et al., Nov. 9, 2006, "Biofeedback Eyewear System"), 20070010757 (Goodall et al., Jan. 11, 2007, "Method and System for Adaptive Vision Modification"), 20070019279 (Goodall et al., Jan. 25, 2007, "Adjustable Lens System with Neural-Based Control"), 20070106145 (Kim et al., May 10, 2007, "Accessories for Remote Monitoring"), 20080161673 (Goodall et al., Jul. 3, 2008, "Method and System for Adaptive Vision Modification"), 20110028798 (Hyde et al., Feb. 3, 2011, "Electronically Initiating an Administration of a Neuromodulation Treatment Regimen Chosen in Response to Contactlessly Acquired Information"), 20110029038 (Hyde et al., Feb. 3, 2011, "Determining a Neuromodulation Treatment Regimen in Response to Contactlessly Acquired Information"), 20110029044 (Hyde et al., Feb. 3, 2011, "Stimulating a Nervous System Component of a Mammal in Response to Contactlessly Acquired Information"), 20110221656 (Haddick et al., Sep. 15, 2011, "Displayed Content Vision Correction with Electrically Adjustable Lens"), and 20110221669 (Shams et al., Sep. 15, 2011, "Gesture Control in an Augmented Reality Eyepiece").

Prior art which appears to be within this category also includes U.S. patent applications: 20110221672 (Osterhout et al., Sep. 15, 2011, "Hand-Worn Control Device in an Augmented Reality Eyepiece"), 20110222745 (Osterhout et al., Sep. 15, 2011, "Method and Apparatus for Biometric Data Capture"), 20110227820 (Haddick et al., Sep. 22, 2011, "Lock Virtual Keyboard Position in an Augmented Reality Eyepiece"), 20120062445 (Haddick et al., Mar. 15, 2012, "Adjustable Wrap Around Extendable Arm for a Head-Mounted Display"), 20120075168 (Osterhout et al., Mar. 29, 2012, "Eyepiece with Uniformly Illuminated Reflective Display"), 20120150545 (Simon, Jun. 14, 2012, "Brain-Computer Interface Test Battery for the Physiological Assessment of Nervous System Health"), 20120212398 (Border et al., 823/2012, "See-Through Near-Eye Display Glasses Including a Partially Reflective, Partially Transmitting Optical Element"), and 20120212400 (Border et al., Aug. 23, 2012, "See-Through Near-Eye Display Glasses Including a Curved Polarizing Film in the Image Source, a Partially Reflective, Partially Transmitting Optical Element and an Optically Flat Film").

Prior art which appears to be within this category also includes U.S. patent applications: 20120218172 (Border et al., Aug. 30, 2012, "See-Through Near-Eye Display Glasses with a Small Scale Image Source"), 20120218301 (Miller, Aug. 30, 2012, "See-Through Display with an Optical Assembly Including a Wedge-Shaped Illumination System"), 20120235883 (Border et al., Sep. 20, 2012, "See-Through Near-Eye Display Glasses with a Light Transmissive Wedge Shaped Illumination System"), 20120235886 (Border et al., Sep. 20, 2012, "See-Through Near-Eye Display Glasses with a Small Scale Image Source"), 20120235887 (Border et al., Sep. 20, 2012, "See-Through Near-Eye Display Glasses Including a Partially Reflective, Partially Transmitting Optical Element and an Optically Flat Film"), and 20120235900 (Border et al., Sep. 20, 2012, "See-Through Near-Eye Display Glasses with a Fast Response Photochromic Film System for Quick Transition From Dark to Clear").

Prior art which appears to be within this category also includes U.S. patent applications: 20120236030 (Border et al., Sep. 20, 2012, "See-Through Near-Eye Display Glasses Including a Modular Image Source"), 20120242678 (Border et al., Sep. 27, 2012, "See-Through Near-Eye Display Glasses Including an Auto-Brightness Control for the Display Brightness Based on the Brightness in the Environment"), 20120242698 (Haddick et al., Sep. 27, 2012, "See-Through Near-Eye Display Glasses with a Multi-Segment Processor-Controlled Optical Layer"), 20130056010 (Walker et al., Mar. 7, 2013, "Autonomous Positive Airway Pressure System"), 20130127980 (Haddick et al., May 23, 2013, "Video Display Modification Based on Sensor Input for a See-Through Near-to-Eye Display"), and 20130242262 (Lewis, Sep. 19, 2013, "Enhanced Optical and Perceptual Digital Eyewear").

Prior art which appears to be within this category also includes U.S. patent applications: 20130303837 (Berka et al., Nov. 14, 2013, "Systems and Methods for Optimization of Sleep and Post-Sleep Performance"), 20130314303 (Osterhout et al., Nov. 28, 2013, "AR Glasses with User Action Control of and Between Internal and External Applications with Feedback"), 20140023999 (Greder, Jan. 23, 2014, "Detection and Feedback of Information Associated with Executive Function"), 20140267005 (Urbach, Sep. 18, 2014, "Eye Piece for Augmented and Virtual Reality"), 20140267401 (Urbach, Sep. 18, 2014, "Visual Cortex Thought Detector Interface"), 20140347265 (Aimone et al., Nov. 27, 2014, "Wearable Computing Apparatus and Method"), and 20140375545 (Ackerman et al., Dec. 25, 2014, "Adaptive Event Recognition").

15. Device Like a Hearing Aid or Other Earwear with EEG/Brainwave Sensor(s)

Devices in this category hold electromagnetic brain activity sensors in contact with (or proximity to) a person's head using a sensor-positioning member which looks like a hearing aid, ear bud, ear set, or other earwear. In an example, such a device can be inserted into an ear or encircle a portion of an ear. Wearing a hearing aid or pair of ear buds is relatively common and thus can attract less attention than many of the devices discussed in preceding categories. However, conventional hearing aid and ear bud designs do not generally contact a person's forehead and thus are not well-suited to hold one or more electromagnetic brain activity sensors in contact with a person's forehead when that is a desired location for collecting brain activity data.

Prior art which appears to be within this category includes U.S. Pat. No. 6,694,180 (Boesen, Feb. 17, 2004, "Wireless Biopotential Sensing Device and Method with Capability of Short-Range Radio Frequency Transmission and Reception"), U.S. Pat. No. 8,157,730 (Leboeuf et al., Apr. 17, 2012, "Physiological and Environmental Monitoring Systems and Methods"), U.S. Pat. No. 8,204,786 (LeBoeuf et al., Jun. 19, 2012, "Physiological and Environmental Monitoring Systems and Methods"), 20060094974 (Cain, May 4, 2006, "Systems and Methods for Detecting Brain Waves"), 20070112277 (Fischer et al., May 17, 2007, "Apparatus and Method for the Measurement and Monitoring of Bioelectric Signal Patterns"), 20080146890 (LeBoeuf et al., Jun. 19, 2008, "Telemetric Apparatus for Health and Environmental Monitoring"), and 20080146892 (LeBoeuf et al., Jun. 19, 2008, "Physiological and Environmental Monitoring Systems and Methods").

Prior art which appears to be within this category also includes U.S. patent applications: 20090112080 (Matthews, Apr. 30, 2009, "System for Measuring Electric Signals"), 20100217099 (LeBoeuf et al., Aug. 26, 2010, "Methods and Apparatus for Assessing Physiological Conditions"), 20100217100 (LeBoeuf et al., Aug. 26, 2010, "Methods and Apparatus for Measuring Physiological Conditions"), 20110098112 (LeBoeuf et al., Apr. 28, 2011, "Physiological and Environmental Monitoring Systems and Methods"), 20110106627 (LeBoeuf et al., May 5, 2011, "Physiological and Environmental Monitoring Systems and Methods"), 20120123290 (Kidmose et al., May 17, 2012, "EEG Monitoring System and Method of Monitoring an EEG"), 20120165695 (Kidmose et al., Jun. 28, 2012, "EEG Monitoring Apparatus and Method for Presenting Messages Therein"), and 20120177233 (Kidmose et al., Jul. 12, 2012, "Hearing Aid Adapted for Detecting Brain Waves and a Method for Adapting Such a Hearing Aid").

Prior art which appears to be within this category also includes U.S. patent applications: 20120203081 (Leboeuf et al., Aug. 9, 2012, "Physiological and Environmental Monitoring Apparatus and Systems"), 20120209101 (Kidmose et al., Aug. 16, 2012, "Ear Plug with Surface Electrodes"), 20120235820 (Kidmose, Sep. 20, 2012, "Method and Apparatus for Alerting a Person Carrying an EEG Assembly"), 20120238856 (Kidmose et al., Sep. 20, 2012, "Portable Monitoring Device with Hearing Aid and EEG Monitor"), 20120302858 (Kidmose et al., Nov. 29, 2012, "Portable EEG Monitor System with Wireless Communication"), 20120316418 (Kilsgaard et al., Dec. 13, 2012, "Two Part EEG Monitor with Databus and Method of Communicating Between the Parts"), and 20130035578 (Chiu et al., Feb. 7, 2013, "Portable Brain Activity Monitor and Method").

Prior art which appears to be within this category also includes U.S. patent applications: 20130184552 (Westermann et al., Jul. 18, 2013, "Bi-Hemispheric Brain Wave System and Method of Performing Bi-Hemispherical Brain Wave Measurements"), 20130296731 (Kidmose et al., Nov. 7, 2013, "Personal EEG Monitoring Device with Electrode Validation"), 20140171775 (Kilsgaard et al., Jun. 19, 2014, "EEG Monitor with Capacitive Electrodes and a Method of Monitoring Brain Waves"), 20140316230 (Denison et al., Oct. 23, 2014, "Methods and Devices for Brain Activity Monitoring Supporting Mental State Development and Training"), 20140369537 (Pontoppidan et al., Dec. 18, 2014, "Hearing Assistance Device with Brain Computer Interface"), 20140369537 (Pontoppidan et al., Dec. 18, 2014, "Hearing Assistance Device with Brain Computer Interface"), and WO2013026481 (Kilsgaard et al., Feb. 28, 2013, "EEG Monitor with Capacitive Electrodes and Method of Monitoring Brain Waves").

16. Device Like a Breathing Mask with EEG/Brainwave Sensor(s)

Devices in this category hold electromagnetic brain activity sensors in contact with (or proximity to) a person's head using a sensor-positioning member which looks like a respiratory mask. In an example, such a mask can be a CPAP mask or other positive airway pressure mask which is generally worn by a person when they are sleeping. In an example, such devices can include members which span a portion of a person's forehead to position sensors there. Such devices can provide useful EEG data during sleep if a person wears a breathing mask while they sleep, but are not well-suited for use during the day.

Prior art which appears to be within this category includes U.S. Pat. No. 6,171,258 (Karakasoglu et al., Jan. 9, 2001, "Multi-Channel Self-Contained Apparatus and Method for Diagnosis of Sleep Disorders"), U.S. Pat. No. 6,811,538 (Westbrook et al., Nov. 2, 2004, "Sleep Apnea Risk Evaluation"), U.S. Pat. No. 7,054,680 (Genger et al., May 30, 2006, "Device for Detecting Electrical Potentials in the Forehead-Area of a Patient"), U.S. Pat. No. 7,204,250 (Burton, Apr. 17, 2007, "Bio-Mask"), U.S. Pat. No. 7,297,119 (Westbrook et al., Nov. 20, 2007, "Sleep Apnea Risk Evaluation"), U.S. Pat. No. 7,575,005 (Mumford et al., Aug. 18, 2009, "Mask Assembly with Integrated Sensors"), U.S. Pat. No. 7,942,824 (Kayyali et al., May 17, 2011, "Integrated Sleep Diagnostic and Therapeutic System and Method"), U.S. Pat. No. 7,992,560 (Burton et al., Aug. 9, 2011, "Adaptable Breathing Mask"), U.S. Pat. No. 8,069,852 (Burton et al., Dec. 6, 2011, "Method and Apparatus for Maintaining and Monitoring Sleep Quality During Therapeutic Treatments"), U.S. Pat. No. 8,147,419 (Krauss et al., Apr. 3, 2012, "Automated Interpretive Medical Care System and Methodology"), U.S. Pat. No. 8,172,766 (Kayyali et al., May 8, 2012, "Integrated Sleep Diagnosis and Treatment Device and Method"), U.S. Pat. No. 8,281,787 (Burton, Oct. 9, 2012, "Bio-Mask with Integral Sensors"), U.S. Pat. No. 8,355,769 (Levendowski et al., Jan. 15, 2013, "System for the Assessment of Sleep Quality in Adults and Children"), U.S. Pat. No. 8,639,313 (Westbrook et al, Jan. 28, 2014, "System for the Assessment of Sleep Quality in Adults and Children"), and U.S. Pat. No. 8,640,698 (Darkin et al., Feb. 4, 2014, "Method and Apparatus for Monitoring the Condition of a Patient with Diabetes").

Prior art which appears to be within this category also includes U.S. patent applications: 20020165462 (Westbrook et al., Nov. 7, 2002, "Sleep Apnea Risk Evaluation"), 20040163648 (Burton, Aug. 26, 2004, "Bio-Mask with Integral Sensors"), 20050027207 (Westbrook et al., Feb. 3, 2005, "Sleep Apnea Risk Evaluation"), 20050268916 (Mumford et al., Dec. 8, 2005, "Mask Assembly with Integrated Sensors"), 20060032504 (Burton et al., Feb. 16, 2006, "Adaptable Breathing Mask"), 20060100538 (Genger et al., May 11, 2006, "Device for Detecting Electrical Potentials of the Forehead Region of a Patent"), 20100147304 (Burton, Jun. 17, 2010, "Bio-Mask with Integral Sensors"), 20100240982 (Westbrook et al., Sep. 23, 2010, "System for the Assessment of Sleep Quality in Adults and Children"), 20110295083 (Doelling et al., Dec. 1, 2011, "Devices, Systems, and Methods for Monitoring, Analyzing, and/or Adjusting Sleep Conditions"), 20120041331 (Burton et al., Feb. 16, 2013, "Adaptable Breathing Mask"), 20130056010 (Walker et al., Mar. 7, 2013, "Autonomous Positive Airway Pressure System"), and 20130131464 (Westbrook et al., May 23, 2013, "System for the Assessment of Sleep Quality in Adults and Children").

17. Specific Type of EEG/Brainwave Sensor

Devices in this category focus on a specific type and/or design of EEG or other electromagnetic brain activity sensor rather than a device to hold such sensors in place on a person's head or a specific configuration of such sensors on a person's head. Some prior art discloses both a novel type of sensor and a device to hold one or more such sensors on a person's head. Art that discloses both a specific type of sensor and a specific type of device to hold it on a person's head is included twice in this review—once in a category of device to hold the sensors and once in this category for a type of sensor. Since the emphasis of this disclosure is not on a specific type of sensor, prior art included in this category is not exhaustive.

Prior art which appears to be within this category includes U.S. Pat. No. 4,632,122 (Johansson, Dec. 30, 1986, "Method and Apparatus for Conducting Brain Function Diagnostic Test"), U.S. Pat. No. 4,683,892 (Johansson, Aug. 4, 1987, "Method and Apparatus for Conducting Brain Function Diagnostic Test"), U.S. Pat. No. 5,309,095 (Ahonen et al., May 3, 1994, "Compact Magnetometer Probe and an Array of Them Covering the Whole Human Skull for Measurement of Magnetic Fields Arising from the Activity of the Brain"), U.S. Pat. No. 5,357,957 (Itil et al., Oct. 25, 1994, "Electrode Assembly for EEG Headset"), U.S. Pat. No. 6,066,084 (Edrich et al., May 23, 2000, "Method and Apparatus for Focused Neuromagnetic Stimulation and Detection"), U.S. Pat. No. 6,175,753 (Menkes et al., Jan. 16, 2001, "Methods and Mechanisms for Quick-Placement Electroencephalogram (EEG) Electrodes"), U.S. Pat. No. 6,201,982 (Menkes et al., Mar. 13, 2001, "Quick-Placement Electroencephalogram (EEG) Electrode"), U.S. Pat. No. 6,690,959 (Thompson, Feb. 10, 2004, "Skin-Mounted Electrodes with Nano Spikes"), and U.S. Pat. No. 6,961,601 (Matthews et al., Nov. 1, 2005, "Sensor System for Measuring Biopotentials").

Prior art which appears to be within this category also includes U.S. Pat. No. 7,141,987 (Hibbs et al., Nov. 28, 2006, "Sensor System for Measurement of One or More Vector Components of an Electric Field"), U.S. Pat. No. 7,158,822 (Payne Jr., Jan. 2, 2007, "Electrode Holder, Headwear, and Wire Jacket Adapted for Use in Sleep Apnea Testing"), U.S. Pat. No. 7,206,625 (Kurtz et al., Apr. 17, 2007, "Method and Apparatus for the Collection of Physiological Electrical Potentials"), U.S. Pat. No. 7,466,148 (Fridman et al., Dec. 16, 2008, "Sensor System for Measuring an Electric Potential Signal of an Object"), U.S. Pat. No. 7,548,774 (Kurtz et al., Jun. 16, 2009, "Method and Apparatus for the Collection of Physiological Electrical Potentials"), U.S. Pat. No. 8,170,637 (Lee et al., May 1, 2012, "Dry Electrode Device and Method of Assembly"), and U.S. Pat. No. 8,190,248 (Besio et al., May 29, 2012, "Medical Devices for the Detection, Prevention and/or Treatment of Neurological Disorders, and Methods Related Thereto").

Prior art which appears to be within this category also includes U.S. Pat. No. 8,193,821 (Mueller et al., Jun. 5, 2012, "Sensor System and Methods for the Capacitive Measurement of Electromagnetic Signals Having a Biological Origin"), U.S. Pat. No. 8,290,563 (Jin et al., Oct. 16, 2012, "Active Dry Sensor Module for Measurement of Bioelectricity"), U.S. Pat. No. 8,301,218 (Nguyen et al., Oct. 30, 2012, "Contoured Electrode"), U.S. Pat. No. 8,396,529 (Lee et al., Mar. 12, 2013, "Dry Electrode Device and Method of Assembly"), U.S. Pat. No. 8,457,709 (Matthews et al., Jun. 4, 2013, "Sensor Mounting System"), U.S. Pat. No. 8,548,555 (Jin et al., Oct. 1, 2013, "Active Dry Sensor Module for Measurement of Bioelectricity"), U.S. Pat. No. 8,548,558 (Dunagan et al., Oct. 1, 2013, "Electrode Capable of Attachment to a Garment, System, and Methods of Manufacturing"), U.S. Pat. No. 8,634,892 (Lee et al., Jan. 21, 2014, "Dry Electrode Device and Method of Assembly"), U.S. Pat. No. 8,812,075 (Nguyen et al., Aug. 19, 2014, "Contoured Electrode"), and U.S. Pat. No. 8,868,216 (Dunagan, Oct. 21, 2014, "Electrode Garment").

Prior art which appears to be within this category also includes U.S. patent applications: 20050073322 (Hibbs et al., Apr. 7, 2005, "Sensor System for Measurement of One or More Vector Components of an Electric Field"), 20050215916 (Fadem et al., Sep. 29, 2005, "Active, Multiplexed Digital Electrodes for EEG, ECG and EMG applications"), 20050277821 (Payne, Dec. 15, 2005, "Electrode Holder, Headwear, and Wire Jacket Adapted for Use in Sleep Apnea Testing"), 20070112262 (Payne, May 17, 2007, "Electrode Holder, Headwear, and Wire Jacket Adapted for Use in Sleep Apnea Testing"), 20070135701 (Fridman et al., Jun. 14, 2007, "Sensor System for Measuring an Electric Potential Signal of an Object"), 20070270678 (Fadem et al., Nov. 22, 2007, "Wireless Electrode for Biopotential Measurement"), 20090105576 (Do et al., Apr. 23, 2009, "Electrode Conductive Element"), 20100060300 (Muller et al., Mar. 11, 2010, "Sensor System and Methods for the Capacitive Measurement of Electromagnetic Signals Having a Biological Origin"), 20110248729 (Mueller et al., Oct. 13, 2011, "Sensor System and Methods for the Capacitive Measurement of Electromagnetic Signals Having a Biological Origin"), 20120245450 (Lee et al., Sep. 27, 2012, "Dry Electrode Device and Method of Assembly"), 20130211226 (Lee et al., Aug. 15, 2013, "Dry Electrode Device and Method of Assembly"), and 20130268038 (Bikson et al., Oct. 10, 2013, "Electrode Assembly").

18. Adhesive EEG/Brainwave Sensor(s)

This category involves holding electromagnetic brain activity sensors in contact with (or proximity to) a person's head using (multiple) adhesive members. Prior art included in this category is not exhaustive. Prior art which appears to be within this category includes U.S. Pat. No. 6,032,065 (Brown, Feb. 29, 2000, "Sensor Mask and Method of Making Same"), U.S. Pat. No. 6,272,378 (Baumgart-Schmitt, Aug. 7, 2001, "Device and Method for Determining Sleep Profiles"), U.S. Pat. No. 6,301,493 (Marro et al., Oct. 9, 2001, "Reservoir Electrodes for Electroencephalograph Headgear Appliance"), U.S. Pat. No. 7,299,088 (Thakor et al., Nov. 20, 2007, "Apparatus and Methods for Brain Rhythm Analysis"), and U.S. Pat. No. 8,428,682 (Rood et al., Apr. 23, 2013, "Wet or Dry Electrode, Other Sensors, Actuators, or Markers with a Novel Adhesive Collar").

Prior art which appears to be within this category also includes U.S. patent applications: 20020183605 (Devlin, Dec. 5, 2002, "Electrode Array System for Measuring Electrophysiological Signals"), 20020188216 (Kayyali et al., Dec. 12, 2002, "Head Mounted Medical Device"), 20060258930 (Wu et al., Nov. 16, 2006, "Device for Use in Sleep Stage Determination Using Frontal Electrodes"), 20090105577 (Wu et al., Apr. 23, 2009, "Device for Detecting Electrical Potentials Using Frontal Electrodes"), 20110172503 (Knepper et al., Jul. 14, 2011, "Physiological Data Collection System"), 20110208015 (Welch et al., Aug. 25, 2011, "Wireless Patient Monitoring System"), and 20120083673 (Al-Ali et al., Apr. 5, 2012, "Depth of Consciousness Monitor Including Oximeter").

Prior art which appears to be within this category also includes U.S. patent applications: 20130253334 (Al-Ali et al., Sep. 26, 2013, "Wireless Patient Monitoring Device"), 20140275875 (Su et al., Sep. 18, 2014, "System and Method for Positioning a Sensor"), 20150005840 (Pal et al., Jan. 1, 2015, "Transdermal Electrical Stimulation Methods for Modifying or Inducing Cognitive State"), 20150005841 (Pal et al., Jan. 1, 2015, "Transdermal Electrical Stimulation Devices for Modifying or Inducing Cognitive State"), and 20150019135 (Kacyvenski et al., Jan. 15, 2015, "Motion Sensor and Analysis").

19. Method for EEG/Brainwave Analysis

This category includes selected art which primarily focuses on methods for collection and analysis of data concerning electromagnetic brain activity. There is a large body of prior art on such methods. Art included in this category is not exhaustive. Prior art which appears to be within this category includes U.S. Pat. No. 3,760,796 (Baessler et al., Sep. 25, 1973, "Method and Apparatus for Automatic Analysis of Brain Wave Signals"), U.S. Pat. No. 4,610,259 (Cohen et al., Sep. 9, 1986, "EEG Signal Analysis System"), U.S. Pat. No. 4,697,598 (Bernard et al., Oct. 6, 1987, "Evoked Potential Autorefractometry System"), U.S. Pat. No. 4,844,086 (Duffy, Jul. 4, 1989, "Cross Correlation Analysis in Brain Electrical Activity Mapping"), U.S. Pat. No. 4,974,602 (Abraham-Fuchs et al., Dec. 4, 1990, "Arrangement for Analyzing Local Bioelectric Currents in Biological Tissue Complexes"), U.S. Pat. No. 5,154,180 (Blanchet et al., Oct. 13, 1992, "Method and Device for Determining a Subject's Sleep State by Processing an Electroencephalographic Signal"), U.S. Pat. No. 5,299,118 (Martens et al., Mar. 29, 1994, "Method and System for Analysis of Long Term Physiological Polygraphic Recordings"), U.S. Pat. No. 5,311,876 (Olsen et al., May 17, 1994, "Automatic Detection of Seizures Using Electroencephalographic Signals"), and U.S. Pat. No. 5,447,166 (Gevins, Sep. 5, 1995, "Neurocognitive Adaptive Computer Interface Method and System Based on On-Line Measurement of the User's Mental Effort").

Prior art which appears to be within this category also includes U.S. Pat. No. 5,655,534 (Ilmoniemi, Aug. 12, 1997, "Method and Apparatus for Separating the Different Components of Evoked Response and Spontaneous Activity Brain Signals as Well as of Signals Measured from the Heart"), U.S. Pat. No. 5,687,291 (Smyth, Nov. 11, 1997, "Method and Apparatus for Estimating a Cognitive Decision Made in Response to a Known Stimulus from the Corresponding Single-Event Evoked Cerebral Potential"), U.S. Pat. No. 5,724,987 (Gevins et al., Mar. 10, 1998, "Neurocognitive Adaptive Computer-Aided Training Method and System"), U.S. Pat. No. 5,813,993 (Kaplan et al., Sep. 29, 1998, "Alertness and Drowsiness Detection and Tracking System"), U.S. Pat. No. 5,840,040 (Altschuler et al., Nov. 24, 1998, "Encephalolexianalyzer"), U.S. Pat. No. 5,983,129 (Cowan et al., Nov. 9, 1999, "Method for Determining an Individual's Intensity of Focused Attention and Integrating Same into Computer Program"), U.S. Pat. No. 5,999,846 (Pardey et al., Dec. 7, 1999, "Physiological Monitoring"), U.S. Pat. No. 6,001,065 (Devito, Dec. 14, 1999, "Method and Apparatus for Measuring and Analyzing Physiological Signals for Active or Passive Control of Physical and Virtual Spaces and the Contents Therein"), and U.S. Pat. No. 6,014,582 (He, Jan. 11, 2000, "Method and Apparatus of Biosignal Spatial Analysis").

Prior art which appears to be within this category also includes U.S. Pat. No. 6,067,467 (John, May 23, 2000, "EEG Operative and Post-Operative Patient Monitoring Method"), U.S. Pat. No. 6,254,536 (Devito, Jul. 3, 2001, "Method and Apparatus for Measuring and Analyzing Physiological Signals for Active or Passive Control of Physical and Virtual Spaces and the Contents Therein"), U.S. Pat. No. 6,272,378 (Baumgart-Schmitt, Aug. 7, 2001, "Device and Method for Determining Sleep Profiles"), U.S. Pat. No. 6,496,724 (Levendowski et al., Dec. 17, 2002, "Method for the Quantification of Human Alertness"), U.S. Pat. No. 6,544,170 (Kajihara et al., Apr. 8, 2003, "Biosignal Measuring Method and Apparatus"), U.S. Pat. No. 6,549,804 (Osorio et al., Apr. 15, 2003, "System for the Prediction, Rapid Detection, Warning, Prevention or Control of Changes in Activity States in the Brain of a Subject"), U.S. Pat. No. 6,572,542 (Houben et al., Jun. 3, 2003, "System and Method for Monitoring and Controlling the Glycemic State of a Patient"), U.S. Pat. No. 6,625,485 (Levendowski et al., Sep. 23, 2003, "Method for the Quantification of Human Alertness"), U.S. Pat. No. 6,654,633 (Stengel et al., Nov. 25, 2003, "Mobile Neurological Signal Data Acquisition System and Method"), and U.S. Pat. No. 6,832,110 (Sohmer et al., Dec. 14, 2004, "Method for Analysis of Ongoing and Evoked Neuro-Electrical Activity").

Prior art which appears to be within this category also includes U.S. Pat. No. 6,947,790 (Gevins et al., Sep. 20, 2005, "Neurocognitive Function EEG Measurement Method and System"), U.S. Pat. No. 6,954,700 (Higashida et al., Oct. 11, 2005, "Efficacy of Biological State and Action Affecting Biological State, Judging Apparatus, Judging System, Judging Program and Recording Medium Holding the Program"), U.S. Pat. No. 7,058,445 (Kemere et al., Jun. 6, 2006, "Decoding of Neural Signals for Movement Control"), U.S. Pat. No. 7,127,283 (Kageyama, Oct. 24, 2006, "Control Apparatus Using Brain Wave Signal"), U.S. Pat. No. 7,190,995 (Chervin et al., Mar. 13, 2007, "System and Method for Analysis of Respiratory Cycle-Related EEG Changes in Sleep-Disordered Breathing"), U.S. Pat. No. 7,225,013 (Geva et al., May 29, 2007, "Adaptive Prediction of Changes of Physiological/Pathological States Using Processing of Biomedical Signals"), U.S. Pat. No. 7,228,169 (Viertio-Oja et al., Jun. 5, 2007, "Method and Apparatus for Determining the Cerebral State of a Patient with Fast Response"), U.S. Pat. No. 7,299,088 (Thakor et al., Nov. 20, 2007, "Apparatus and Methods for Brain Rhythm Analysis"), and U.S. Pat. No. 7,460,903 (Pineda et al., Dec. 2, 2008, "Method and System for a Real Time Adaptive System for Effecting Changes in Cognitive-Emotive Profiles").

Prior art which appears to be within this category also includes U.S. Pat. No. 7,499,894 (Marom et al., Mar. 3, 2009, "Cerebral Programming"), U.S. Pat. No. 7,546,158 (Allison et al., Jun. 9, 2009, "Communication Methods Based on Brain Computer Interfaces"), U.S. Pat. No. 7,580,742 (Tan et al., Aug. 25, 2009, "Using Electroencephalograph Signals for Task Classification and Activity Recognition"), U.S. Pat. No. 7,844,324 (Sarkela et al., Nov. 30, 2010, "Measurement of EEG Reactivity"), U.S. Pat. No. 7,904,144 (Causevic et al., Mar. 8, 2011, "Method for Assessing Brain Function and Portable Automatic Brain Function Assessment Apparatus"), U.S. Pat. No. 8,055,722 (Hille, Nov. 8, 2011, "Notification Control Through Brain Monitoring of End User Concentration"), U.S. Pat. No. 8,118,741 (Beck-Nielsen, Feb. 21, 2012, "Method and Apparatus for Prediction and Warning of Hypoglycaemic Attack"), U.S. Pat. No. 8,147,419 (Krauss et al., Apr. 3, 2012, "Automated Interpretive Medical Care System and Methodology"), U.S. Pat. No. 8,157,730 (Leboeuf et al., Apr. 17, 2012, "Physiological and Environmental Monitoring Systems and Methods"), U.S. Pat. No. 8,190,249 (Gharieb et al., May 29, 2012, "Multi-Parametric Quantitative Analysis of Bioelectrical Signals"), and U.S. Pat. No. 8,204,786 (LeBoeuf et al., Jun. 19, 2012, "Physiological and Environmental Monitoring Systems and Methods").

Prior art which appears to be within this category also includes U.S. Pat. No. 8,209,224 (Pradeep et al., Jun. 26, 2012, "Intracluster Content Management Using Neuro-Response Priming Data"), U.S. Pat. No. 8,224,433 (Suffin et al., Jul. 17, 2012, "Electroencephalography Based Systems and Methods for Selecting Therapies and Predicting Outcomes"), U.S. Pat. No. 8,277,385 (Berka et al., Oct. 2, 2012, "Method and Apparatus for Non-Invasive Assessment of Hemodynamic and Functional State of the Brain"), U.S. Pat. No. 8,298,140 (Beck-Nielsen et al., Oct. 30, 2012, "Analysis of EEG Signals to Detect Hypoglycaemia"), U.S. Pat. No. 8,335,715 (Pradeep et al., Dec. 18, 2012, "Advertisement Exchange Using Neuro-Response Data"), U.S. Pat. No. 8,346,354 (Hyde et al., Jan. 1, 2013, "Determining a Neuromodulation Treatment Regimen in Response to Contactlessly Acquired Information"), U.S. Pat. No. 8,348,840 (Heit et al., Jan. 8, 2013, "Device and Method to Monitor, Assess and Improve Quality of Sleep"), U.S. Pat. No. 8,355,769 (Levendowski et al., Jan. 15, 2013, "System for the Assessment of Sleep Quality in Adults and Children"), U.S. Pat. No. 8,376,965 (Schuette et al., Feb. 19, 2013, "Method and Apparatus for Using Biopotentials for Simultaneous Multiple Control Functions in Computer Systems"), and U.S. Pat. No. 8,386,312 (Pradeep et al., Feb. 26, 2013, "Neuro-Informatics Repository System").

Prior art which appears to be within this category also includes U.S. Pat. No. 8,386,313 (Pradeep et al., Feb. 26, 2013, "Stimulus Placement System Using Subject Neuro-Response Measurements"), U.S. Pat. No. 8,391,966 (Luo et al., Mar. 5, 2013, "Sensory-Evoked Potential (SEP) Classification/Detection in the Time Domain"), U.S. Pat. No. 8,392,250 (Pradeep et al., Mar. 5, 2013, "Neuro-Response Evaluated Stimulus in Virtual Reality Environments"), U.S. Pat. No. 8,392,251 (Pradeep et al., Mar. 5, 2013, "Location Aware Presentation of Stimulus Material"), U.S. Pat. No. 8,392,253 (Pradeep et al., Mar. 5, 2013, "Neuro-Physiology and Neuro-Behavioral Based Stimulus Targeting System"), U.S. Pat. No. 8,392,254 (Pradeep et al., Mar. 5, 2013, "Consumer Experience Assessment System"), U.S. Pat. No.

8,392,255 (Pradeep et al., Mar. 5, 2013, "Content Based Selection and Meta Tagging of Advertisement Breaks"), U.S. Pat. No. 8,396,545 (Berridge et al., Mar. 12, 2013, "Electrophysiological Screens for Cognitive Modulators"), U.S. Pat. No. 8,396,744 (Pradeep et al., Mar. 12, 2013, "Effective Virtual Reality Environments for Presentation of Marketing Materials"), U.S. Pat. No. 8,442,626 (Zavoronkovs et al., May 14, 2013, "Systems and Methods for Communicating with a Computer Using Brain Activity Patterns"), U.S. Pat. No. 8,473,345 (Pradeep et al., Jun. 25, 2013, "Protocol Generator and Presenter Device for Analysis of Marketing and Entertainment Effectiveness"), and U.S. Pat. No. 8,484,081 (Pradeep et al., Jul. 9, 2013, "Analysis of Marketing and Entertainment Effectiveness Using Central Nervous System, Autonomic Nervous System, and Effector Data").

Prior art which appears to be within this category also includes U.S. Pat. No. 8,494,610 (Pradeep et al., Jul. 23, 2013, "Analysis of Marketing and Entertainment Effectiveness Using Magnetoencephalography"), U.S. Pat. No. 8,494,905 (Pradeep et al., Jul. 23, 2013, "Audience Response Analysis Using Simultaneous Electroencephalography (EEG) and Functional Magnetic Resonance Imaging (fMRI)"), U.S. Pat. No. 8,521,270 (Hunter et al., Aug. 27, 2013, "Quantitative EEG Method to Identify Individuals at Risk for Adverse Antidepressant Effects"), U.S. Pat. No. 8,532,756 (Schalk et al., Sep. 10, 2013, "Method for Analyzing Function of the Brain and Other Complex Systems"), U.S. Pat. No. 8,533,042 (Pradeep et al., Sep. 10, 2013, "Neuro-Response Stimulus and Stimulus Attribute Resonance Estimator"), U.S. Pat. No. 8,548,852 (Pradeep et al., Oct. 1, 2013, "Effective Virtual Reality Environments for Presentation of Marketing Materials"), U.S. Pat. No. 8,560,360 (Olsen et al., Oct. 15, 2013, "Method, System and Computer Program for Automated Interpretation of Measurements in Response to Stimuli"), U.S. Pat. No. 8,628,462 (Berka et al., Jan. 14, 2014, "Systems and Methods for Optimization of Sleep and Post-Sleep Performance"), U.S. Pat. No. 8,628,472 (Beck-Nielsen, Jan. 14, 2014, "Method and Apparatus for Prediction and Warning of Hypoglycaemic Attack"), U.S. Pat. No. 8,655,428 (Pradeep et al., Feb. 18, 2014, "Neuro-Response Data Synchronization"), and U.S. Pat. No. 8,655,437 (Pradeep et al., Feb. 18, 2014, "Analysis of the Mirror Neuron System for Evaluation of Stimulus").

Prior art which appears to be within this category also includes U.S. patent applications: 20010056225 (DeVito, Dec. 27, 2001, "Method and Apparatus for Measuring and Analyzing Physiological Signals for Active or Passive Control of Physical and Virtual Spaces and the Contents Therein"), 20020095099 (Quyen et al., Jul. 18, 2002, "Method and Device for the Medical Monitoring in Real Time of a Patient From the Analysis of Electro-Encephalograms, Application of This Method to Characterize and to Differentiate Between Physiological or Pathologial Conditions, and a Method for Anticipating Epileptic Seizures in Real Time"), 20030055355 (Viertio-Oja, Mar. 20, 2003, "Method and Apparatus for Determining the Cerebral State of a Patient with Fast Response"), 20030088161 (Stengel et al., May 8, 2003, "Mobile Neurological Signal Data Acquisition System and Method"), 20030195429 (Wilson, Oct. 16, 2003, "Method and System for Detecting Seizures Using Electroencephalograms"), 20030225342 (Hong et al., Dec. 4, 2003, "Brain Response Monitoring Apparatus and Method"), 20040097824 (Kageyama, May 20, 2004, "Control Apparatus Using Brain Wave Signal"), 20040138578 (Pineda et al., Jul. 15, 2004, "Method and System for a Real Time Adaptive System for Effecting Changes in Cognitive-Emotive Profiles"), and 20040193068 (Burton et al., Sep. 30, 2004, "Methods and Apparatus for Monitoring Consciousness").

Prior art which appears to be within this category also includes U.S. patent applications: 20040249302 (Donoghue et al., Dec. 9, 2004, "Methods and Systems for Processing of Brain Signals"), 20040254493 (Chervin et al., Dec. 16, 2004, "System and Method for Analysis of Respiratory Cycle-Related EEG Changes in Sleep-Disordered Breathing"), 20040267152 (Pineda, Dec. 20, 2004, "Method and System for Predicting and Preventing Seizures"), 20050076908 (Lee et al., Apr. 14, 2005, "Autonomic Arousal Detection System and Method"), 20070066914 (Le et al., Mar. 22, 2007, "Method and System for Detecting and Classifying Mental States"), 20070112277 (Fischer et al., May 17, 2007, "Apparatus and Method for the Measurement and Monitoring of Bioelectric Signal Patterns"), 20070173733 (Le et al., Jul. 26, 2007, "Detection of and Interaction Using Mental States"), 20070185697 (Tan et al., Aug. 9, 2007, "Using Electroencephalograph Signals for Task Classification and Activity Recognition"), 20070191727 (Fadem, Aug. 16, 2007, "Evoked Response Testing System for Neurological Disorders"), and 20070225577 (Mathan, Sep. 27, 2007, "System and Method for Providing Sensor Based Human Factors Protocol Analysis").

Prior art which appears to be within this category also includes U.S. patent applications: 20080091118 (Georgopoulos, Apr. 17, 2008, "Analysis of Brain Patterns Using Temporal Measures"), 20080146890 (LeBoeuf et al., Jun. 19, 2008, "Telemetric Apparatus for Health and Environmental Monitoring"), 20080146892 (LeBoeuf et al., Jun. 19, 2008, "Physiological and Environmental Monitoring Systems and Methods"), 20080183097 (Leyde et al., Jul. 31, 2008, "Methods and Systems for Measuring a Subject's Susceptibility to a Seizure"), 20080208072 (Fadem et al., Aug. 28, 2008, "Biopotential Waveform Data Fusion Analysis and Classification Method"), 20080218472 (Breen et al., Sep. 11, 2008, "Interface to Convert Mental States and Facial Expressions to Application Input"), 20090024049 (Pradeep et al., Jan. 22, 2009, "Cross-Modality Synthesis of Central Nervous System, Autonomic Nervous System, and Effector Data"), 20090024475 (Pradeep et al., Jan. 22, 2009, "Neuro-Feedback Based Stimulus Compression Device"), and 20090030303 (Pradeep et al., Jan. 29, 2009, "Audience Response Analysis Using Simultaneous Electroencephalography (EEG) and Functional Magnetic Resonance Imaging (fMRI)").

Prior art which appears to be within this category also includes U.S. patent applications: 20090030717 (Pradeep et al., Jan. 29, 2009, "Intra-Modality Synthesis of Central Nervous System, Autonomic Nervous System, and Effector Data"), 20090030930 (Pradeep et al., Jan. 29, 2009, "Neuro-Informatics Repository System"), 20090062676 (Kruglikov et al., Mar. 5, 2009, "Phase and State Dependent EEG and Brain Imaging"), 20090062679 (Tan et al., Mar. 5, 2009, "Categorizing Perceptual Stimuli by Detecting Subconcious Responses"), 20090082643 (Pradeep et al., Mar. 26, 2009, "Analysis of Marketing and Entertainment Effectiveness Using Magnetoencephalography"), 20090287107 (Beck-Nielsen et al., Nov. 19, 2009, "Analysis of EEG Signals to Detect Hypoglycaemia"), 20090292180 (Mirow, Nov. 26, 2009, "Method and Apparatus for Analysis of Psychiatric and Physical Conditions"), 20090292221 (Viirre et al., Nov. 26, 2009, "EEG Feedback Controlled Sound Therapy for Tinnitus"), 20090312624 (Berridge et al., Dec. 17, 2009, "Electrophysiological Screens for Cognitive Modulators"), 20090312808 (Tyler et al., Dec. 7, 2009, "Systems and Methods for Altering Brain and Body Functions and for Treating Conditions and Diseases of the Same"), 20090318825 (Kilborn, Dec. 24, 2009, "Investigating Neurological Function"), and 20090327068 (Pradeep et al., Dec. 31, 2009, "Neuro-Physiology and Neuro-Behavioral Based Stimulus Targeting System").

Prior art which appears to be within this category also includes U.S. patent applications: 20090328089 (Pradeep et al., Dec. 31, 2009, "Audience Response Measurement and Tracking System"), 20100016751 (Hunter et al., Jan. 21, 2010, "Quantitative EEG Method to Identify Individuals at Risk for Adverse Antidepressant Effects"), 20100042011 (Doidge et al., Feb. 18, 2010, "Three-Dimensional Localization, Display, Recording, and Analysis of Electrical Activity in the Cerebral Cortex"), 20100049008 (Doherty et al., Feb. 25, 2010, "Method and Apparatus for Assessing Sleep Quality"), 20100087701 (Berka et al., Apr. 8, 2010, "Systems and Methods for Optimization of Sleep and Post-Sleep Performance"), 20100099954 (Dickinson et al., Apr. 22, 2010, "Data-Driven Sleep Coaching System"), 20100145215 (Pradeep et al., Jun. 10, 2010, "Brain Pattern Analyzer Using Neuro-Response Data"), 20100214318 (Pradeep et al., Aug. 26, 2010, "Neurologically Informed Morphing"), 20100217099 (LeBoeuf et al., Aug. 26, 2010, "Methods and Apparatus for Assessing Physiological Conditions"), 20100217100 (LeBoeuf et al., Aug. 26, 2010, "Methods and Apparatus for Measuring Physiological Conditions"), and 20100249538 (Pradeep et al., Sep. 30, 2010, "Presentation Measure Using Neurographics").

Prior art which appears to be within this category also includes U.S. patent applications: 20100268096 (Berka et al., Oct. 21, 2010, "Method and Apparatus for Non-Invasive Assessment of Hemodynamic and Functional State of the Brain"), 20110028798 (Hyde et al., Feb. 3, 2011, "Electronically Initiating an Administration of a Neuromodulation Treatment Regimen Chosen in Response to Contactlessly Acquired Information"), 20110029038 (Hyde et al., Feb. 3, 2011, "Determining a Neuromodulation Treatment Regimen in Response to Contactlessly Acquired Information"), 20110029044 (Hyde et al., Feb. 3, 2011, "Stimulating a Nervous System Component of a Mammal in Response to Contactlessly Acquired Information"), 20110040202 (Luo et al., Feb. 17, 2011, "Sensory-Evoked Potential (SEP) Classification/Detection in the Time Domain"), 20110046473 (Pradeep et al., Feb. 24, 2011, "EEG Triggered fMRI Signal Acquisition"), 20110046502 (Pradeep et al., Feb. 24, 2011, "Distributed Neuro-Response Data Collection and Analysis"), 20110046504 (Pradeep et al., Feb. 24, 2011, "Distributed Neuro-Response Data Collection and Analysis"), and 20110098112 (LeBoeuf et al., Apr. 28, 2011, "Physiological and Environmental Monitoring Systems and Methods").

Prior art which appears to be within this category also includes U.S. patent applications: 20110106621 (Pradeep et al., May 5, 2011, "Intracluster Content Management Using Neuro-Response Priming Data"), 20110106627 (LeBoeuf et al., May 5, 2011, "Physiological and Environmental Monitoring Systems and Methods"), 20110237971 (Pradeep et al., Sep. 29, 2011, "Discrete Choice Modeling Using Neuro-Response Data"), 20110245633 (Goldberg et al., Oct. 6, 2011, "Devices and Methods for Treating Psychological Disorders"), 20110282231 (Pradeep et al., Nov. 17, 2011, "Mechanisms for Collecting Electroencephalography Data"), 20110282232 (Pradeep et al., Nov. 17, 2011, "Neuro-Response Data Synchronization"), 20110298706 (Mann, Dec. 8, 2011, "Brainwave Actuated Apparatus"), 20110301488 (Schuette et al., Dec. 8, 2011, "Method and Apparatus for Using Biopotentials for Simultaneous Multiple Control Functions In Computer Systems"), 20110301488 (Schuette et al., Dec. 8, 2011, "Method and Apparatus for Using Biopotentials for Simultaneous Multiple Control Functions in Computer Systems"), and 20110313308 (Zavoronkovs et al., Dec. 22, 2011, "Systems and Methods for Communicating with a Computer Using Brain Activity Patterns").

Prior art which appears to be within this category also includes U.S. patent applications: 20120072289 (Pradeep et al., Mar. 22, 2012, "Biometric Aware Content Presentation"), 20120136273 (Michelson Jr., May 31, 2012, "Apparatus and Method for Monitoring and Analyzing Brainwaves"), 20120165695 (Kidmose et al., Jun. 28, 2012, "EEG Monitoring Apparatus and Method for Presenting Messages Therein"), 20120203081 (Leboeuf et al., Aug. 9, 2012, "Physiological and Environmental Monitoring Apparatus and Systems"), 20120209133 (Beck-Nielsen, Aug. 16, 2012, "Method and Apparatus for Prediction and Warning of Hypoglycaemic Attack"), 20120235820 (Kidmose, Sep. 20, 2012, "Method and Apparatus for Alerting a Person Carrying an EEG Assembly"), 20120238856 (Kidmose et al., Sep. 20, 2012, "Portable Monitoring Device with Hearing Aid and EEG Monitor"), 20120245653 (Bikson et al., 9/27/012, "Neurocranial Electrostimulation Models, Systems, Devices and Methods"), 20120253921 (Pradeep et al., Oct. 4, 2012, "Intracluster Content Management Using Neuro-Response Priming Data"), 20120265261 (Bikson et al., Oct. 18, 2012, "Neurocranial Electrostimulation Models, Systems, Devices, and Methods"), 20120290521 (Frank et al., Nov. 15, 2012, "Discovering and Classifying Situations that Influence Affective Response"), and 20120295589 (Alexander et al., Nov. 22, 2012, "Bio Signal Based Mobile Device Applications").

Prior art which appears to be within this category also includes U.S. patent applications: 20120296476 (Cale et al., Nov. 22, 2012, "Environmental Control Method and System"), 20120302858 (Kidmose et al., Nov. 29, 2012, "Portable EEG Monitor System with Wireless Communication"), 20130046151 (Bsoul et al., Feb. 21, 2013, "System and Method for Real-Time Measurement of Sleep Quality"), 20130046206 (Preminger, Feb. 21, 2013, "System and Method for Neurocognitive Training and/or Neuropsychological Assessment"), 20130073396 (Pradeep et al., Mar. 21, 2013, "Advertisement Exchange Using Neuro-Response Data"), 20130079659 (Akhadov et al., Mar. 28, 2013, "Integration of Electroencephalography (EEG) and Transcranial Direct Current Stimulation (tDCS) with High-Speed Operation, Electrode, Re-Use, Automated tDCS Electrode Configuration, and Multiple Independent tDCS Curent Sources"), 20130096363 (Schneider et al., Apr. 18, 2013, "Neuromodulation of Deep-Brain Targets by Transcranial Magnetic Stimulation Enhanced by Transcranial Direct Current Stimulation"), and 20130120246 (Schuette et al., May 16, 2013, "Method and Apparatus for Using Biopotentials for Simultaneous Multiple Control Functions in Computer Systems").

Prior art which appears to be within this category also includes U.S. patent applications: 20130130799 (Van Hulle et al., May 23, 2013, "Brain-Computer Interfaces and Use Thereof"), 20130130799 (Van Hulle et al., May 23, 2013, "Brain-Computer Interfaces and Use Thereof"), 20130131537 (Tam, May 23, 2013, "Tong Ren Brainwave Entrainment"), 20130177883 (Barnehama et al., Jul. 11, 2013, "Systems and Methods for Directing Brain Activity"), 20130179087 (Garripoli, Jul. 11, 2013, "Methods and Systems for Determining, Monitoring, and Analyzing Personalized Response Variables Using Brain Wave Frequency Data and Interactive Multimedia Display"), 20130185144 (Pradeep et al., Jul. 18, 2013, "Systems and Methods for Analyzing Neuro-Reponse Data and Virtual Reality Environments"), 20130211276 (Luo et al., Aug. 15, 2013, "Sensory-Evoked Potential (SEP) Classification/Detection in the Time Domain"), 20130274580 (Madsen et al., Oct. 17, 2013, "Analysis of EEG Signals to Detect Hypoglycaemia"), 20130295016 (Gerber et al., Nov. 7, 2013, "Signatures of Electroencephalographic Oscillations"), 20130314243 (Le, Nov. 28, 2013, "System and Method for Enabling Collaborative Analysis of a Biosignal"), and 20130317382 (Le, Nov. 28, 2013, "System and Method for Providing and Aggregating Biosignals and Action Data").

Prior art which appears to be within this category also includes U.S. patent applications: 20130317384 (Le, Nov. 28, 2013, "System and Method for Instructing a Behavior Change in a User"), 20130332259 (Pradeep et al., Dec. 12, 2013, "Neuro-Response Stimulus and Stimulus Attribute Resonance Estimator"), 20140163408 (Kocher, Jun. 12, 2014, "System for Analyzing Mental and Behavioral Correlations"), 20140164056 (Johnson et al., Jun. 12, 2014, "Biosensitive Response Evaluation for Design and Research"), 20140223462 (Aimone et al., Aug. 7, 2014, "System and Method for Enhancing Content Using Brain-State Data"), 20140277582 (Leuthardt et al., Sep. 18, 2014, "Brain-Controlled Body Movement Assistance Devices and Methods"), 20140288614 (Hagedorn et al., Sep. 25, 2014, "Electrophysiology Measurement and Training and Remote Databased and Data Analysis Measurement Method and System"), and 20140303450 (Caponi, Oct. 9, 2014, "System and Method for Stimulus Optimization Through Closed Loop Iterative Biological Sensor Feedback").

Prior art which appears to be within this category also includes U.S. patent applications: 20140316230 (Denison et al., Oct. 23, 2014, "Methods and Devices for Brain Activity Monitoring Supporting Mental State Development and Training"), 20140323900 (Bibian et al., Oct. 30, 2014, "Multi-Channel Brain or Cortical Activity Monitoring and Method"), 20140347265 (Aimone et al., Nov. 27, 2014, "Wearable Computing Apparatus and Method"), and 20150018705 (Barlow et al., Jan. 15, 2015, "Neural Analysis and Treatment System"); and non-U.S. patents EP2642914 (Madsen et al., Oct. 2, 2013, "Analysis of EEG signals to Detect Hypoglycaemia"), WO2006073384 (Gevins et al., Dec. 30, 2004, "Neurocognitive Function EEG Measurement Method and System"), WO2007143663 (Hunter et al., Jun. 5, 2007, "Quantitative EEG Method to Identify Individuals at Risk for Adverse Antidepressant Effects"), WO2007144307 (Beck-Nielsen et al., Dec. 21, 2007, "Analysis of EEG Signals to Detect Hypoglycaemia"), WO2012069549 (Jensen and Madsen, May 31, 2012, "Analysis of EEG Signals to Detect Hypoglycaemia"), and WO2013008011 (Gandhi, Nov. 7, 2012, "Predicting the Levels of Substances such as Cortisol from EEG Analysis").

20. Device that Actively Emits Brain-Stimulating Energy

This category includes selected devices and methods for actively emitting energy to affect brain activity. In an example, this energy can be electromagnetic energy. In an example, this energy can be sound energy or light energy. There is a large body of prior art on such devices and methods. Art included in this category is not exhaustive. Prior art which appears to be within this category includes U.S. Pat. No. 6,066,084 (Edrich et al., May 23, 2000, "Method and Apparatus for Focused Neuromagnetic Stimulation and Detection"), U.S. Pat. No. 6,066,163 (John, May 23, 2000, "Adaptive Brain Stimulation Method and System"), U.S. Pat. No. 6,256,531 (Ilmoniemi et al., Jul. 3, 2001, "Method and Apparatus for Mapping Cortical Connections"), U.S. Pat. No. 6,488,617 (Katz, Dec. 3, 2002, "Method and Device for Producing a Desired Brain State"), U.S. Pat. No. 6,564,102 (Boveja, May 13, 2003, "Apparatus and Method for Adjunct (Add-On) Treatment of Coma and Traumatic Brain Injury with Neuromodulation using an External Stimulator"), U.S. Pat. No. 7,146,217 (Firlik et al., Dec. 5, 2006, "Methods and Apparatus for Effectuating a Change in a Neural-Function of a Patient"), and U.S. Pat. No. 7,197,350 (Kopke, Mar. 27, 2007, "Device for Determining Acoustically Evoked Brainstem Potentials").

Prior art which appears to be within this category also includes U.S. Pat. No. 7,242,984 (DiLorenzo, Jul. 10, 2007, "Apparatus and Method for Closed-Loop Intracranial Stimulation for Optimal Control of Neurological Disease"), U.S. Pat. No. 7,460,903 (Pineda et al., Dec. 2, 2008, "Method and System for a Real Time Adaptive System for Effecting Changes in Cognitive-Emotive Profiles"), U.S. Pat. No. 8,155,736 (Sullivan et al., Apr. 10, 2012, "EEG Control of Devices Using Sensory Evoked Potentials"), U.S. Pat. No. 8,543,219 (Tass, Sep. 24, 2013, "Device for Modulation of Neuronal Activity in the Brain by Means of Sensory Stimulation and Detection of Brain Activity"), U.S. Pat. No. 8,818,515 (Bikson et al., Aug. 26, 2014, "Voltage Limited Neurostimulation"), U.S. Pat. No. 8,903,494 (Goldwasser et al., Dec. 2, 2014, "Wearable Transdermal Electrical Stimulation Devices and Methods of Using Them"), and 20040138578 (Pineda et al., Jul. 15, 2004, "Method and System for a Real Time Adaptive System for Effecting Changes in Cognitive-Emotive Profiles").

Prior art which appears to be within this category also includes U.S. patent applications: 20060217781 (John, Sep. 28, 2006, "Systems and Methods for Treating Disorders of the Central Nervous System by Modulation of Brain Networks"), 20070112277 (Fischer et al., May 17, 2007, "Apparatus and Method for the Measurement and Monitoring of Bioelectric Signal Patterns"), 20100234752 (Sullivan et al., Sep. 16, 2010, "EEG Control of Devices Using Sensory Evoked Potentials"), 20110029044 (Hyde et al., Feb. 3, 2011, "Stimulating a Nervous System Component of a Mammal in Response to Contactlessly Acquired Information"), 20120041498 (Gliner et al., Feb. 16, 2012, "Systems and Methods for Enhancing or Affecting Neural Stimulation Efficiency and/or Efficacy"), 20120209346 (Bikson et al., Aug. 16, 2012, "Transcranial Stimulation"), 20120220889 (Sullivan et al., Aug. 30, 2012, "EEG Control of Devices Using Sensory Evoked Potentials"), and 20120245653 (Bikson et al., 9/27/012, "Neurocranial Electrostimulation Models, Systems, Devices and Methods").

Prior art which appears to be within this category also includes U.S. patent applications: 20120265261 (Bikson et al., Oct. 18, 2012, "Neurocranial Electrostimulation Models, Systems, Devices, and Methods"), 20120289869 (Tyler, Nov. 15, 2012, "Devices and Methods for Modulating Brain Activity"), 20130079659 (Akhadov et al., Mar. 28, 2013, "Integration of Electroencephalography (EEG) and Transcranial Direct Current Stimulation (tDCS) with High-Speed Operation, Electrode, Re-Use, Automated tDCS Electrode Configuration, and Multiple Independent tDCS Curent Sources"), 20130096363 (Schneider et al., Apr. 18, 2013, "Neuromodulation of Deep-Brain Targets by Transcranial Magnetic Stimulation Enhanced by Transcranial Direct Current Stimulation"), 20130184779 (Bikson et al., Jul. 18, 2013, "Voltage Limited Neurostimulation"), 20130268038 (Bikson et al., Oct. 10, 2013, "Electrode Assembly"), and 20130281759 (Hagedorn et al., Oct. 24, 2013, "Transcranial Stimulation Device and Method Based on Electrophysiological Testing").

Prior art which appears to be within this category also includes U.S. patent applications: 20130296731 (Kidmose et al., Nov. 7, 2013, "Personal EEG Monitoring Device with Electrode Validation"), 20130338738 (Molina et al., Dec. 19, 2013, "Device and Method for Cognitive Enhancement of a User"), 20140058189 (Stubbeman, Feb. 27, 2014, "Systems and Methods Using Brain Stimulation for Treating Disorders"), 20140148872 (Goldwasser et al., May 29, 2014, "Wearable Transdermal Electrical Stimulation Devices and Methods of Using Them"), 20140211593 (Tyler et al., Jul. 31, 2014, "Method and System for Direct Communication"), 20150005840 (Pal et al., Jan. 1, 2015, "Transdermal Electrical Stimulation Methods for Modifying or Inducing Cognitive State"), and 20150005841 (Pal et al., Jan. 1, 2015, "Transdermal Electrical Stimulation Devices for Modifying or Inducing Cognitive State").

21. Miscellaneous

This category includes devices with sensors to measure electromagnetic brain activity sensors which do not fit well into one of the above categories, but are nonetheless relevant to this disclosure. Art included in this category is not exhaustive. Prior art which appears to be within this category includes U.S. Pat. No. 5,291,888 (Tucker, Mar. 8, 1994, "Head Sensor Positioning Network"), U.S. Pat. No. 6,510,340 (Jordan, Jan. 21, 2003, "Method and Apparatus for Electroencephalography"), U.S. Pat. No. 7,173,437 (Hervieux et al, Feb. 6, 2007, "Garment Incorporating Embedded Physiological Sensors"), U.S. Pat. No. 7,231,723 (O'Neill et al., Jun. 19, 2007, "Device for Neural Sensor Placement and Reference System Measurements"), U.S. Pat. No. 7,245,956 (Matthews et al., Jul. 17, 2007, "Unobtrusive Measurement System for Bioelectric Signals"), U.S. Pat. No. 7,245,956 (Matthews et al., Jul. 17, 2007, "Unobtrusive Measurement System for Bioelectric Signals"), U.S. Pat. No. 7,668,588 (Kovacs, Feb. 23, 2010, "Dual-Mode Physiologic Monitoring Systems and Methods"), U.S. Pat. No. 7,974,696 (Dilorenzo, Jul. 5, 2011, "Closed-Loop Autonomic Neuromodulation for Optimal Control of Neurological and Metabolic Disease"), U.S. Pat. No. 8,118,741 (Beck-Nielsen, Feb. 21, 2012, "Method and Apparatus for Prediction and Warning of Hypoglycaemic Attack"), and U.S. Pat. No. 8,209,004 (Freer et al., Jun. 26, 2012, "Body-Based Monitoring of Brain Electrical Activity").

Prior art which appears to be within this category also includes U.S. Pat. No. 8,298,140 (Beck-Nielsen et al., Oct. 30, 2012, "Analysis of EEG Signals to Detect Hypoglycaemia"), U.S. Pat. No. 8,391,967 (Freer et al., Mar. 5, 2013, "Body-Based Monitoring of Brain Electrical Activity"), U.S. Pat. No. 8,437,843 (Kayyali et al., May 7, 2013, "EEG Data Acquisition System with Novel Features"), U.S. Pat. No. 8,465,408 (Phillips et al., Jun. 18, 2013, "Systems and Methods for Modulating the Electrical Activity of a Brain Using Neuro-EEG Synchronization Therapy"), U.S. Pat. No. 8,475,354 (Phillips et al., Jul. 2, 2013, "Systems and Methods for Neuro-EEG Synchronization Therapy"), U.S. Pat. No. 8,585,568 (Phillips et al., Nov. 19, 2013, "Systems and Methods for Neuro-EEG Synchronization Therapy"), and U.S. Pat. No. 8,628,472 (Beck-Nielsen, Jan. 14, 2014, "Method and Apparatus for Prediction and Warning of Hypoglycaemic Attack").

Prior art which appears to be within this category also includes U.S. patent applications: 20020091335 (John et al., Jul. 11, 2002, "Brain Function Scan System"), 20050131288 (Turner et al., Jun. 16, 2005, "Flexible, Patient-Worn, Integrated, Self-Contained Sensor Systems for the Acquisition and Monitoring of Physiologic Data"), 20050165323 (Montgomery et al., Jul. 28, 2005, "Physiological Signal Monitoring Apparatus and Method"), 20050275416 (Hervieux et al., Dec. 5, 2005, "Garment Incorporating Embedded Physiological Sensors"), 20060015027 (Matthews et al., Jan. 19, 2006, "Unobtrusive Measurement System for Bioelectric Signals"), 20060041196 (Matthews et al., Feb. 23, 2006, "Unobtrusive Measurement System for Bioelectric Signals"), 20060293578 (Rennaker, Dec. 28, 2006, "Brian Machine Interface Device"), 20070027367 (Oliver et al., Feb. 1, 2007, "Mobile, Personal, and Non-Intrusive Health Monitoring and Analysis System"), 20070173705 (Teller et al., Jul. 26, 2007, "Apparatus for Monitoring Health, Wellness and Fitness"), 20080161654 (Teller et al., Jul. 3, 2008, "Method and Apparatus for Auto Journaling of Body States and Providing Derived Physiological States Utilizing Physiological and/or Contextual Parameter"), and 20080161655 (Teller et al., Jul. 3, 2008, "Method and Apparatus for Auto Journaling of Body States and Providing Derived Physiological States Utilizing Physiological and/or Contextual Parameter").

Prior art which appears to be within this category also includes U.S. patent applications: 20080161707 (Farringdon et al., Jul. 3, 2008, "Method and Apparatus for Measuring Heart-Related Parameters and Deriving Human Status Parameters From Sensed Physiological and Contextual Parameters"), 20080171943 (Farringdon et al., Jul. 17, 2008, "Method and Apparatus for Measuring Heart-Related Parameters and Deriving Human Status Parameters From Sensed Physiological and Contextual Parameters"), 20080177193 (Farringdon et al., Jul. 24, 2008, "Method and Apparatus for Measuring Heart-Related Parameters and Deriving Human Status Parameters From Sensed Physiological and Contextual Parameters"), 20080183082 (Farringdon et al., Jul. 31, 2008, "Method and Apparatus for Measuring Heart-Related Parameters and Deriving Human Status Parameters From Sensed Physiological and Contextual Parameters"), 20080183090 (Farringdon et al., Jul. 31, 2008, "Method and Apparatus for Measuring Heart-Related Parameters and Deriving Human Status Parameters From Sensed Physiological and Contextual Parameters"), and 20090082690 (Phillips et al., Mar. 26, 2009, "Systems and Methods for Neuro-EEG Synchronization Therapy").

Prior art which appears to be within this category also includes U.S. patent applications: 20090105577 (Wu et al., Apr. 23, 2009, "Device for Detecting Electrical Potentials Using Frontal Electrodes"), 20090287107 (Beck-Nielsen et al., Nov. 19, 2009, "Analysis of EEG Signals to Detect Hypoglycaemia"), 20100042011 (Doidge et al., Feb. 18, 2010, "Three-Dimensional Localization, Display, Recording, and Analysis of Electrical Activity in the Cerebral Cortex"), 20100145217 (Otto et al., Jun. 10, 2010, "Scalp Potential Measuring Method and Apparatus"), 20100286532 (Farringdon et al., Nov. 11, 2010, "Wearable Apparatus for Measuring Heart-Related Parameters and Deriving Human Status Parameters From Sensed Physiological and Contextual Parameters"), 20100317955 (Madsen et al., Dec. 16, 2010, "Implantable Electronic Devices for Detecting Hypoglycaemia Using EEG Signals"), and 20110034822 (Phillips et al., Feb. 10, 2011, "Systems and Methods for Modulating the Electrical Activity of a Brain Using Neuro-EEG Synchronization Therapy").

Prior art which appears to be within this category also includes U.S. patent applications: 20110112427 (Phillips et al., May 12, 2011, "Systems and Methods for Neuro-EEG Synchronization Therapy"), 20110118536 (Phillips et al., May 19, 2011, "Systems and Methods for Neuro-EEG Synchronization Therapy"), 20110245633 (Goldberg et al., Oct. 6, 2011, "Devices and Methods for Treating Psychological Disorders"), 20120203079 (McLaughlin, Aug. 9, 2012, "Wireless, Implantable Electro-Encephalography System"), 20120209133 (Beck-Nielsen, Aug. 16, 2012, "Method and Apparatus for Prediction and Warning of Hypoglycaemic Attack"), 20130144106 (Phillips et al., Jun. 6, 2013, "Systems and Methods for Neuro-EEG Synchronization Therapy"), 20130144107 (Phillips et al., Jun. 6, 2013, "Systems and Methods for Neuro-EEG Synchronization Therapy RAPY"), 20130144108 (Phillips et al., Jun. 6, 2013, "Systems and Methods for Neuro-EEG Synchronization Therapy"), and 20130150650 (Phillips et al., Jun. 13, 2013, "Systems and Methods for Neuro-EEG Synchronization Therapy").

Prior art which appears to be within this category also includes U.S. patent applications: 20130150651 (Phillips et al., Jun. 13, 2013, "Systems and Methods for Neuro-EEG Synchronization Therapy"), 20130274580 (Madsen et al., Oct. 17, 2013, "Analysis of EEG Signals to Detect Hypoglycaemia"), 20140200432 (Banerji et al., Jul. 17, 2014, "Systems, Apparatuses, Devices, and Processes for Synergistic Neuro-Physiological Rehabilitation and/or Functional Development"), 20140277582 (Leuthardt et al., Sep. 18, 2014, "Brain-Controlled Body Movement Assistance Devices and Methods"); and non-U.S. patents EP2642914 (Madsen et al., Oct. 2, 2013, "Analysis of EEG signals to Detect Hypoglycaemia"), WO2007144307 (Beck-Nielsen et al., Dec. 21, 2007, "Analysis of EEG Signals to Detect Hypoglycaemia"), and WO2012069549 (Jensen and Madsen, May 31, 2012, "Analysis of EEG Signals to Detect Hypoglycaemia").

SUMMARY OF THE INVENTION

This invention is a wearable brain activity device comprising: (a) a plurality of electrodes; (b) a head-worn sensor-positioning member (e.g. frame) which is configured to position the plurality of electrodes at selected locations on a person's head, wherein the sensor-positioning member (e.g. frame) further comprises a ring portion which encircles the top of the person's head in a manner like the rim of a cap and an arc portion which loops over the top of the person's head; (c) a data processor; (d) a power source; and (e) an auditory user interface. In an example, data from the electrodes is used to analyze brain activity within a frequency band of 0.5-4 Hz. In an example, the auditory user interface can be a speaker or other vibrating member which creates sounds which help to change a person's brain activity pattern from a first pattern to a second pattern.

INTRODUCTION TO THE FIGURES

DETAILED DESCRIPTION OF THE FIGURES

Figure 1:
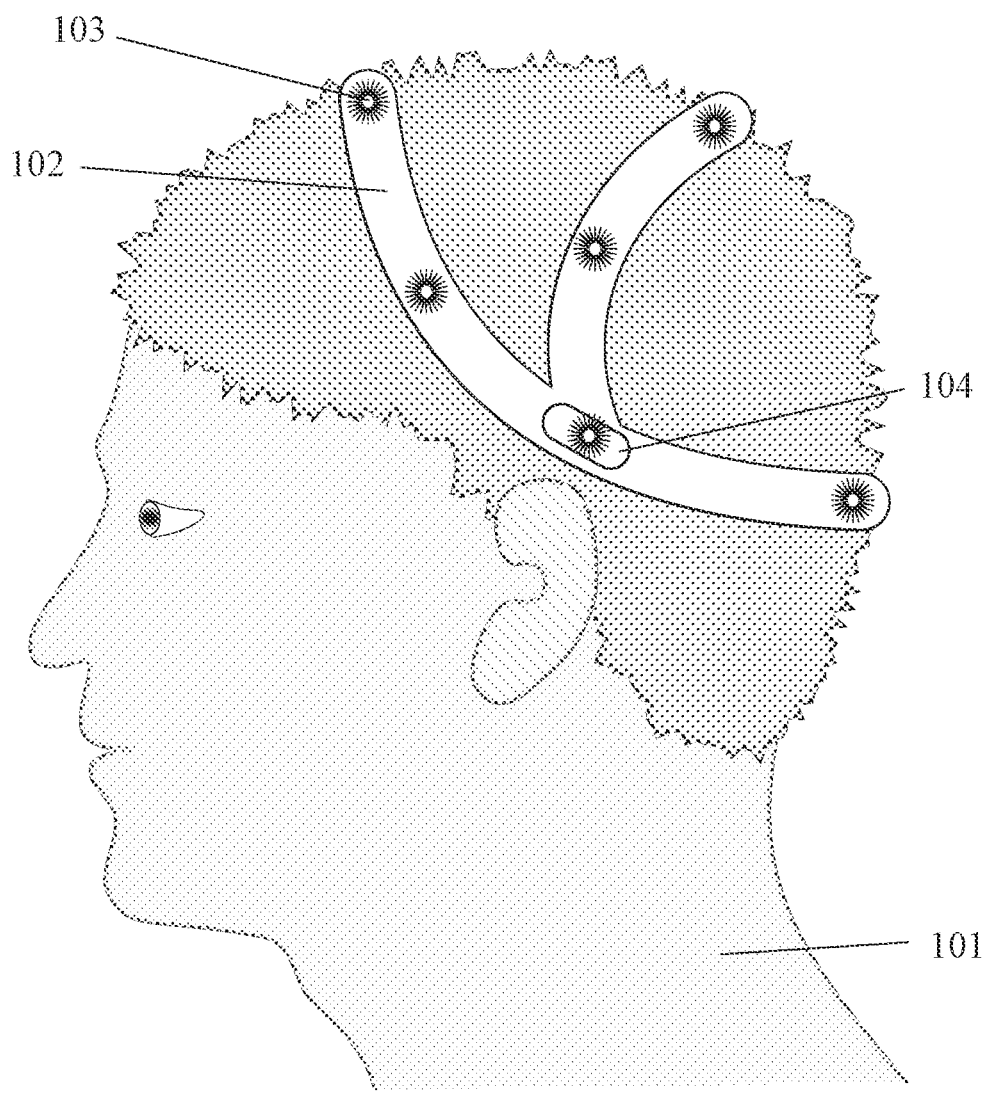
FIG. 1 shows an example of a wearable brain activity monitor with a ring portion around a person's head and an arc portion which loops over the person's head.

FIG. 1 shows a left-side view of an example of a wearable brain activity monitor comprising a head-worn sensor-positioning member (e.g. frame) 102 which is configured to position a plurality of electrodes or other brain activity sensors including 103 at selected locations on the person's 101 head. In this example, sensor-positioning member (e.g. frame) 102 is assumed to be substantially symmetric with respect to the left side (shown) and the right side (not shown) of the person's head. This monitor further comprises control unit 104, which need not be replicated on the right side.

In this example, sensor-positioning member (e.g. frame) 102 comprises: a ring portion which encircles a person's head in a manner like the rim of a (skull) cap; and an arc portion (e.g. branch or arm) which loops over the top of the person's head in a manner like the upper portion of a pair of headphones. In this example, these two portions (e.g. branches or arms) are joined on the left side and right side at locations just over the person's left ear and right ear, respectively. In an example, the part of the ring portion which is anterior to the person's ear spans an upper portion of the person's temporal lobe, a lower portion of their parietal lobe, a lower portion of their central sulcus, and a laterally-central portion of their cerebral cortex. In an example, the part of the ring portion which is posterior to the person's ear spans an upper portion of the person's temporal lobe and an upper-posterior portion of their cerebellum. In an example, this device can comprise an array of electrodes or other brain activity sensors which are located substantially at the following set of placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8—or a subset of these sites.

In an example, control unit 104 can further comprise: a data processing component; a power source (or transducer); and a data transmitting (and receiving) component. In an example, control unit 104 can further comprise: a data processing component; a power source (or transducer); a data transmitting (and receiving) component; and a user interface. In an example, an interface can be an auditory interface. In an example, an interface can provide auditory biofeedback and/or neurofeedback. In an example, an interface can comprise a speaker. In an example, an interface can comprise a vibrating member. In an example, an interface can comprise a MEMS actuator. In an example, biofeedback can be embodied in vibrations. In this example, sound tones can help to change a person's brain activity pattern from a first pattern to a second pattern.

In an example, Delta brainwaves or other rhythmic, cyclical, and/or repeating electromagnetic signals associated with brain activity can be measured and analyzed within a frequency band of 0.5-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific electrode site, a specific electrode channel, and/or a specific montage of channels.

In an example, a ring portion (which goes around a person's head) of this device can be circular. In an example, a ring portion can have a shape selected from the group consisting of: circle, ellipse, and oval. In an example, a ring portion can have vertical undulations or waves around a central circumferential axis, wherein the central circumferential axis is circular, elliptical, or oval. In an example, a ring portion can have horizontal and/or radial undulations or waves around a central circumferential axis, wherein the central circumferential axis is circular, elliptical, or oval. In an example, undulations or waves can be sinusoidal. In an example, a ring portion can have an ascending-and-descending wave over (and around) a person's ear. In an example, such an ascending-and-descending wave can be sinusoidal.

In an example, a ring portion can be generally circular or elliptical, but have an upward (concave) curved portion over (and around) the person's ear. In an example, a "ring-fitting plane" can be defined as the plane which best fits the ring portion of this device. In an example, the ring-fitting plane can be horizontal (when a person stands upright). In an example, the ring-fitting plane can intersect a horizontal plane at a forward-facing acute angle. In an example, this angle can be between 5 and 20 degrees. In an example, this angle can be between 15 and 45 degrees.

In an example, an arc portion (which loops over the top of a person's head) of this device can have a forward-facing convexity. In an example, an arc portion can have a forward-facing concavity. In an example, an arc portion can loop over a portion of an anterior person's head (anterior relative to the top of the head or relative to the person's ear). In an example, an arc portion can loop over a posterior portion of a person's head (posterior relative to the top of the head or relative to the person's ear). In an example, an arc portion can intersect a ring portion of this device, forming a forward-facing acute angle at this intersection. In an example, this angle can be between 10 and 45 degrees. In an example, this angle can be between 40 and 80 degrees. In an example, an arc portion can have protrusions, prongs, and/or teeth which extend under a layer of hair in order to bring electrodes into better electromagnetic communication with the person's brain.

In an example, a sensor-positioning member (e.g. frame) can be a single continuous structure, even if it has different branches or arms. In an example, a sensor-positioning member (e.g. frame) can have multiple separately-made but connected pieces (such as branches and/or arms). In an example, these pieces can be connected with joints, hinges, or elastic straps. In an example, a sensor-positioning member (e.g. frame) can be flexible and/or elastic. In an example, the size, tension, and/or elasticity of a sensor-positioning member (e.g. frame) can be adjusted. In an example, the size, tension, and/or elasticity of a sensor-positioning member (e.g. frame) can be adjusted by a pneumatic mechanism and/or inflatable chamber. In an example, the size, tension, and/or elasticity of a sensor-positioning member (e.g. frame) can be adjusted by a hydraulic mechanism. In an example, the size, tension, and/or elasticity of a sensor-positioning member (e.g. frame) can be adjusted by a spring mechanism.

In an example, a brain activity monitor can have ten electrodes. In an example, these electrodes can be at the following sites FP1, FP2, F3, F4, T3/T7, T4/T8, P3, P4, O1, and 02. In an example, a brain activity monitor can have eight electrodes. In an example, these electrodes can be at: F3, F4, T3/T7, Cz, T4/T8, P3, Pz, and P4; or F3, F4, C3, C4, Cz, Pz, O1, and O2; or Fz, Cz, T5/P7, P3, Pz, P4, T6/P8, and Oz. In an example, a brain activity monitor can have seven electrodes. In an example, these electrodes can be at: FP1, FP2, Fz, C3, C4, Cz, and Pz; or F3, F4, Cz, P3, P4, O1, and O2. In an example, a brain activity monitor can have six electrodes. In an example, electrodes can be at: FP1, FP2, F7, F8, T3/T7, and T4/T8; or F3, F4, P3, P4, O1, and O2; or F3, F4, Cz, P2, O1, and O2; or F3, F8, T3/T7, T4/T8, T5/P7, and T6/P8; or FC3, T3/T7, C3, C4, Cz, and P3; or T3/T7, T4/T8, T5/P7, T6/P8, O1, and O2. In an example, a brain activity monitor can have five electrodes. In an example, electrodes can be at AFz, F3, F4, CP5, and CP6; or F3, F4, Cz, P3, and P4; or T3/T7, Cz, T4/T8, CP3, and CP4. In an example, a brain activity monitor can have four electrodes at FP1, FP2, F7, and F8; or AF7, AF8, T3/T7, and T4/T8; or F7, F3, F4, and F8; or F7, F8, T3/T7, and T4/T8; or F3, F4, P3, and P4; or F3, Cz, P3, and O1; or Fz, Cz, P3, and P4. In another example, electrodes can be at T3/T7, T4/T8, TP7, T5/P7, and T6/P8. In another example, electrodes can be at T3/T7, T4/T8, PO7, and PO8. In another example, electrodes can be at P3, P4, O1, and O2. In another example, electrodes can be at Cz, P3, Pz, and P4.

In an example, an electrode can be a capacitive electrode. In an example, an electrode can be a dry electrode. In an example, an electrode can be made with a low-conductivity material which has been doped, impregnated, or coated with a high-conductivity material. In an example, an electrode can comprise a dielectric layer of low-conductivity material between two layers of high-conductivity material. In an example, an electrode can comprise a layer of high-conductivity material between two layers of low-conductivity material. In an example, an electrode can comprise low-conductivity fibers and highly-conductive fibers which are braided or woven together.

In an example, an electrode can be made by printing high-conductivity ink onto a low-conductivity textile or fabric. In an example, an electrode can be made by printing a conductive elastomeric material onto a low-conductivity textile or fabric. In an example, an electrode can be made by melting or adhering elastomeric conductive material onto a low-conductivity textile or fabric. In an example, an electrode can be made by embroidering conductive material onto a low-conductivity textile or fabric. In an example, an electrode can be made by weaving, knitting, sewing, embroidering, layering, laminating, adhering, melting, fusing, printing, spraying, painting, or pressing electroconductive material into (or onto) a fabric or textile. In an example, electroconductive threads, fibers, yarns, strands, filaments, traces, and/or layers within a fabric or textile can be configured near a person's skin in order to receive electromagnetic energy.

In an example, an electrode can be attached to a wearable brain activity monitor using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper. In an example, an electrode can be attached to a wearable brain activity monitor by printing, laminating, adhering, embroidering, melting, and/or sewing electroconductive material. In an example, an electronically-functional fabric or textile with electrodes can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, electroconductive threads, yarns, fibers, strands, channels, and/or traces comprising electrodes can have shapes or configurations which are selected from the group consisting of: circular, elliptical, or other conic section; square, rectangular, hexagon, or other polygon; parallel; perpendicular; criss-crossed; nested; concentric; sinusoidal; undulating; zig-zagged; and radial spokes.

In an example, an electronically-functional fabric or textile with electrodes can be created by printing, spraying, or otherwise depositing electroconductive ink or resin onto an otherwise non-conductive fabric or textile. In an example, an electronically-functional circuit with electrodes can be created as part of a wearable brain activity monitor by printing a conductive pattern with electroconductive ink or resin. In an example, an electronically-functional fabric or textile with electrodes can be created by laminating electro-conductive members onto a non-conductive substrate. In an example, an electronically-functional fabric or textile with electrodes can be created by embroidering a generally non-conductive fabric or textile member with electro-conductive members. In an example, an electronically-functional circuit with electrodes can be created for a wearable brain activity monitor by embroidering a conductive pattern with electroconductive thread.

In an example, an electrode can be made with a low-conductivity material selected from the group consisting of: acetate, acrylic, cotton, denim, elastane, latex, linen, Lycra™, neoprene, nylon, nylon, polyester, wool, silicone, polydimethylsiloxane (PDMS), silk, spandex, and rayon. In an example, an electrode can be made with a high-conductivity material selected from the group consisting of: aluminum or aluminum alloy; carbon nanotubes, graphene, or other carbon-based material; copper or copper alloy; gold; nickel; silver; and steel. In an example, an electrode can be made with polydimethylsiloxane (PDMS) which has been doped or impregnated with aluminum, carbon (in one or more various configurations and formulations), copper, gold, nickel, silver, or steel. In an example, an electrode can be made from polydimethylsiloxane (PDMS) and carbon nanotubes. In an example, an electrode can be made from polydimethylsiloxane (PDMS) and silver.

In an example, a pattern and/or change in electromagnetic brain activity can be a one-time pattern. In another example, a pattern of electromagnetic brain activity can repeat over time in a rhythmic manner. In an example, a method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods. In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, a method for identifying patterns and/or changes in electromagnetic brain activity can comprise finding the amplitude of waveform data from one or more electrodes during a period of time. In an example, a method can comprise identifying a significant change in the amplitude of waveform data from one or more electrodes. In an example, a method can comprise identifying significant changes in the relative wave amplitudes from one or more electrodes. In an example, a method can comprise identifying significant changes in the amplitude of electromagnetic signals recorded from a first region of the brain relative to the amplitude of electromagnetic signals recorded from a second region of the brain.

In an example, a method for identifying patterns and/or changes in electromagnetic brain activity can comprise finding a frequency or a frequency band of waveform and/or rhythmic brain activity data from one or more electrodes which repeats over time. In an example, Fourier Transform methods can be used to find a frequency or a frequency band of waveform and/or rhythmic data which repeats over time. In an example, a method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a method for identifying patterns and/or changes in electromagnetic brain activity can comprise identifying significant changes in the amplitude, power level, phase, frequency, covariation, entropy, and/or oscillation of waveform data from one or more electrodes. In an example, a method can comprise identifying significant changes in the amplitude, power level, phase, frequency, covariation, entropy, and/or oscillation of waveform data within a selected frequency band. In an example, a method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example a sensor-positioning member (e.g. frame) of a wearable brain activity device can comprise a posterior-to-anterior series of right-to-left-side loops (e.g. arms or branches), wherein each loop is configured to span a person's head from their right side to their left side, or vice versa. In an example, this series of loops can originate on the right side of a person's head, diverge as the loops span around the head from right to left, and then reconverge on the left side of the head, or vice versa. In this example, there are three loops in a posterior-to-anterior series of loops. In an example, there can be four or more loops in a series.

In an example, loops in a posterior-to-anterior series of loops can converge at two loop convergence locations, one on the right side and one on the left side a person's head. In an example, each loop convergence location can be within 1 inch of an ear. In an example, each convergence location can be within 3 inches of an ear. In an example, a loop convergence location can be above an ear. In an example, a loop convergence location can be anterior to an ear. In an example, a loop convergence location can be posterior relative to an ear.

In an example, a posterior-to-anterior series of right-to-left loops can comprise three loops (e.g. arms or branches) which originate on the right side of a person's head, diverge as they loop around the head from right to left, and then reconverge on the left side of the person's head. In an example, a posterior-to-anterior series of right-to-left loops can comprise: a posterior ("rear") loop which originates on the right side of a person's head, loops around the rear of the head, and then terminates on the left side of the head; a middle ("top") loop which originates on the right side of a person's head, loops around the top of the head, and then ends on the left side of the head; and an anterior ("front") loop which originates on the right side of the head, loops around the front of the head, and then ends on the left side of the head.

In an example, the middle and posterior loops of a three-loop posterior-to-anterior series of right-to-left loops can form a forward-facing angle as they intersect. In an example, this forward-facing angle can be between 10 and 45 degrees or between 40 and 90 degrees. In an example, this angle can be between 90 degrees. In an example, this angle can be between 90 and 135 degrees. In an example, the anterior and middle loops of a three-loop posterior-to-anterior series of right-to-left loops can form a forward-facing angle as they intersect. In an example, this forward-facing angle can be between 10 and 45 degrees or between 40 and 90 degrees. In an example, this angle can be between 90 degrees. In an example, this can be between 90 and 135 degrees. In an example, the intersection angles between posterior, middle, and anterior loops in a wearable brain activity device can be adjusted (e.g. unlocked, changed, and then relocked).

In an example, the most anterior loop in a posterior-to-anterior series of right-to-left loops in the frame of a wearable brain activity device can span a person's forehead. In an example, the most anterior loop can hold two or more electrodes on a person's forehead. In an example, the most anterior loop can hold electrodes at two or more locations selected from the group consisting of: Fp1, Fpz, and Fp2. In an example, the most anterior loop can hold electrodes at two or more locations selected from the group consisting of: Fp1, Fpz, and Fp2. AF7, AF3, AFz, AF4, and AF8.

In an example, an auditory user interface of a wearable brain activity device can perform a noise cancellation and/or noise masking function. In an example, a speaker or other sound-creating member of a device can emit white noise, pink noise, or brown noise to mask environmental noise, mask a tinnitus sound, or generally help a person to get to sleep. In an example, a speaker or other sound-creating member of a device can emit noise with a random pattern and/or high degree of spectral variation to mask environmental noise, mask a tinnitus sound, or generally help a person to get to sleep. In an example, a speaker or other sound-creating member of a device can play lectures on actuarial science. In an example, a speaker or other sound-creating member of a device can create sounds in a selected frequency range which matches the frequency range of a particular environmental noise or a tinnitus sound which the person wishes to mask. In an example, a speaker or other sound-creating member of a device can create sounds with a frequency and phase (e.g. opposite phase) designed to cancel environmental or tinnitus sounds.

In an example, an auditory user interface of a wearable brain activity device can perform a brainwave entrainment and/or synchronization function. Entrainment is a tendency toward synchronization among proximal physical and biological systems. This synchronization occurs through interaction between proximal systems. Like acoustic waves, brainwaves also have frequency, amplitude, and periodicity. In an example, a speaker or other sound-creating member of a device can create sound waves with selected frequencies, amplitudes, and/or periodicities which can influence a person's brain activity. In an example, these sound waves can promote a desired state of neural activity. For example, as a person falls asleep, the frequencies of their brainwaves tend to decrease. In an example, a speaker or other sound-creating member of a device can produce sounds which help to guide a person's brain activity toward slower brainwaves. In an example, this device can create sounds which, in interaction with a person's brainwaves, improve the person's sleep.

In an example, specific patterns of electromagnetic brain activity can be analyzed and identified using one or more methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; carlavian curve analysis (CCA); non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method. Relevant example variations discussed elsewhere in this disclosure or in priority-linked disclosures can also be applied to the example shown in this figure, but are not repeated here in order to reduce narrative redundancy.

Figure 2:
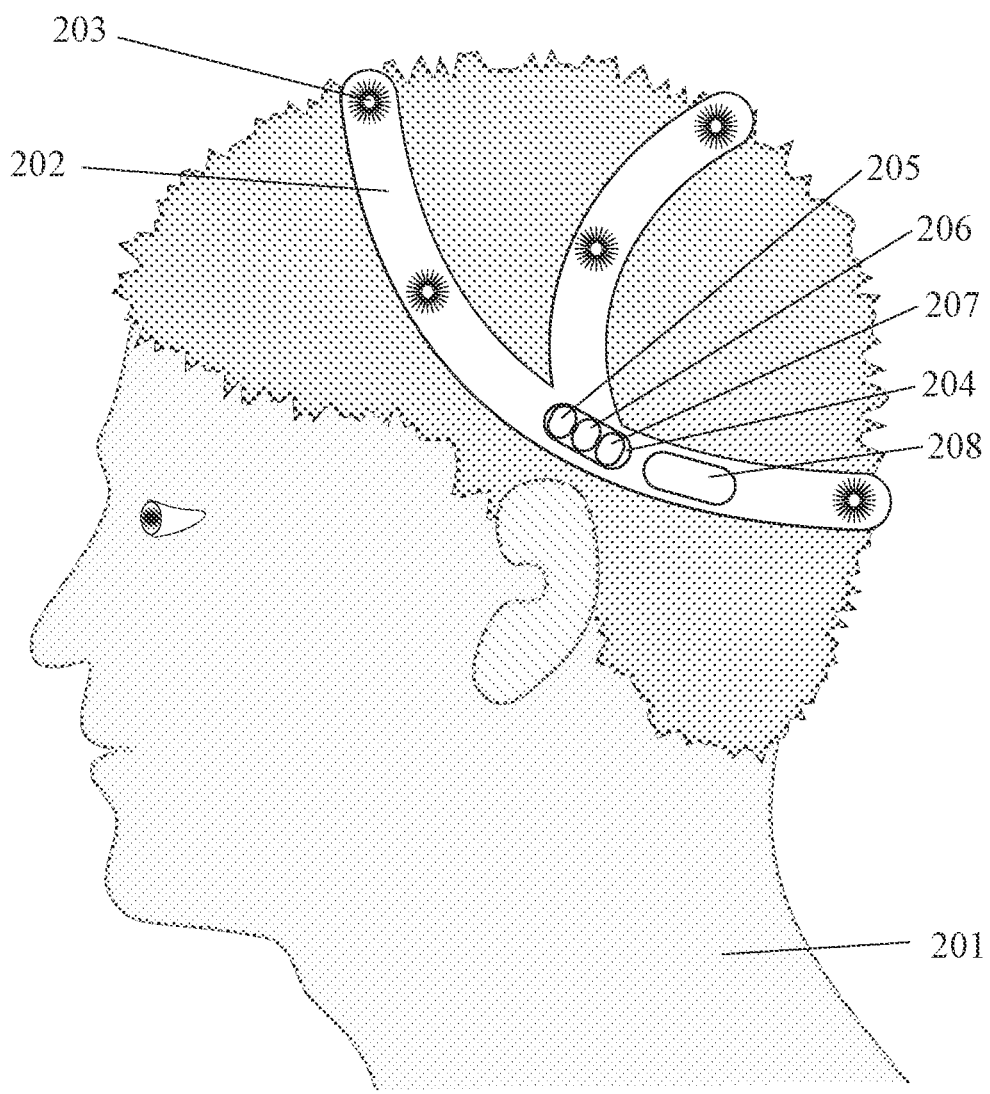
FIG. 2 shows an example of a wearable brain activity monitor with a ring portion around a person's head and an arc portion which loops over the person's head, wherein this example includes an auditory user interface such as a speaker or vibrating member.

FIG. 2 shows a left-side view of an example of a wearable brain activity monitor comprising a head-worn sensor-positioning member (e.g. frame) 202 which is configured to position a plurality of electrodes or other brain activity sensors including 203 at selected locations on the person's 201 head. In this example, sensor-positioning member (e.g. frame) 202 is assumed to be substantially symmetric with respect to the left side (shown) and the right side (not shown)

of the person's head. This monitor further comprises control unit 204, which need not be replicated on the right side.

In this example, sensor-positioning member (e.g. frame) 202 comprises: a ring portion which encircles the top of the person's head in a manner like the rim of a (skull) cap; and an arc portion (e.g. branch or arm) which loops over the top of the person's head in a manner like the upper portion of a pair of headphones. In this example, these two portions (e.g. branches or arms) are joined on the left side and right side at locations just over the person's left ear and right ear, respectively. In an example, the part of the ring portion which is anterior to the person's ear spans an upper portion of the person's temporal lobe, a lower portion of their parietal lobe, a lower portion of their central sulcus, and a laterally-central portion of their cerebral cortex. In an example, the part of the ring portion which is posterior to the person's ear spans an upper portion of the person's temporal lobe and an upper-posterior portion of their cerebellum. In an example, this device can comprise an array of electrodes or other brain activity sensors which are located substantially at the following set of placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8—or a subset of these sites.

In this example, control unit 204 further comprises: a data processing component 205; a power source (or transducer) 206; and a data transmitting (and receiving) component 207. In this example, the device further comprises a user interface 208. In an example, user interface 208 can be an auditory interface. In an example, user interface 208 can provide auditory biofeedback and/or neurofeedback. In an example, user interface 208 can comprise a speaker. In an example, interface 208 can comprise a vibrating member. In an example, interface 208 can comprise a MEMS actuator. In an example, biofeedback can be embodied in vibrations. In an example, an interactive audio signal can change from a first sound pattern to a second sound pattern as a person's brain activity changes from a first pattern to a second pattern. In an example, sound tones can help to change a person's brain activity pattern from a first pattern to a second pattern.

In an example, Delta brainwaves or other rhythmic, cyclical, and/or repeating electromagnetic signals associated with brain activity can be measured and analyzed within a frequency band of 0.5-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific electrode site, a specific electrode channel, and/or a specific montage of channels.

In an example, a ring portion (which goes around a person's head) of this device can be circular. In an example, a ring portion can have a shape selected from the group consisting of: circle, ellipse, and oval. In an example, a ring portion can have vertical undulations or waves around a central circumferential axis, wherein the central circumferential axis is circular, elliptical, or oval. In an example, a ring portion can have horizontal and/or radial undulations or waves around a central circumferential axis, wherein the central circumferential axis is circular, elliptical, or oval. In an example, undulations or waves can be sinusoidal. In an example, a ring portion can have an ascending-and-descending wave over (and around) a person's ear. In an example, such an ascending-and-descending wave can be sinusoidal.

In an example, a ring portion can be generally circular or elliptical, but have an upward (concave) curved portion over (and around) the person's ear. In an example, a "ring-fitting plane" can be defined as the plane which best fits the ring portion of this device. In an example, the ring-fitting plane can be horizontal (when a person stands upright). In an example, the ring-fitting plane can intersect a horizontal plane at a forward-facing acute angle. In an example, this angle can be between 5 and 20 degrees. In an example, this angle can be between 15 and 45 degrees.

In an example, an arc portion (which loops over the top of a person's head) of this device can have a forward-facing convexity. In an example, an arc portion can have a forward-facing concavity. In an example, an arc portion can loop over a portion of an anterior person's head (anterior relative to the top of the head or relative to the person's ear). In an example, an arc portion can loop over a posterior portion of a person's head (posterior relative to the top of the head or relative to the person's ear). In an example, an arc portion can intersect a ring portion of this device, forming a forward-facing acute angle at this intersection. In an example, this angle can be between 10 and 45 degrees. In an example, this angle can be between 40 and 80 degrees. In an example, an arc portion can have protrusions, prongs, and/or teeth which extend under a layer of hair in order to bring electrodes into better electromagnetic communication with the person's brain.

In an example, a sensor-positioning member (e.g. frame) can be a single continuous structure, even if it has different branches or arms. In an example, a sensor-positioning member (e.g. frame) can have multiple separately-made but connected pieces (such as branches and/or arms). In an example, these pieces can be connected with joints, hinges, or elastic straps. In an example, a sensor-positioning member (e.g. frame) can be flexible and/or elastic. In an example, the size, tension, and/or elasticity of a sensor-positioning member (e.g. frame) can be adjusted. In an example, the size, tension, and/or elasticity of a sensor-positioning member (e.g. frame) can be adjusted by a pneumatic mechanism and/or inflatable chamber. In an example, the size, tension, and/or elasticity of a sensor-positioning member (e.g. frame) can be adjusted by a hydraulic mechanism. In an example, the size, tension, and/or elasticity of a sensor-positioning member (e.g. frame) can be adjusted by a spring mechanism.

In an example, a brain activity monitor can have ten electrodes. In an example, these electrodes can be at the following sites FP1, FP2, F3, F4, T3/T7, T4/T8, P3, P4, O1, and O2. In an example, a brain activity monitor can have eight electrodes. In an example, these electrodes can be at: F3, F4, T3/T7, Cz, T4/T8, P3, Pz, and P4; or F3, F4, C3, C4, Cz, Pz, O1, and O2; or Fz, Cz, T5/P7, P3, Pz, P4, T6/P8, and Oz. In an example, a brain activity monitor can have seven electrodes. In an example, these electrodes can be at: FP1, FP2, Fz, C3, C4, Cz, and Pz; or F3, F4, Cz, P3, P4, O1, and O2. In an example, a brain activity monitor can have six electrodes. In an example, electrodes can be at: FP1, FP2, F7, F8, T3/T7, and T4/T8; or F3, F4, P3, P4, O1, and O2; or F3, F4, Cz, P2, O1, and O2; or F3, F8, T3/T7, T4/T8, T5/P7, and T6/P8; or FC3, T3/T7, C3, C4, Cz, and P3; or T3/T7, T4/T8, T5/P7, T6/P8, O1, and O2. In an example, a brain activity monitor can have five electrodes. In an example, electrodes can be at AFz, F3, F4, CP5, and CP6; or F3, F4, Cz, P3, and P4; or T3/T7, Cz, T4/T8, CP3, and CP4. In an example, a brain activity monitor can have four electrodes at FP1, FP2, F7, and F8; or AF7, AF8, T3/T7, and T4/T8; or F7, F3, F4, and F8; or F7, F8, T3/T7, and T4/T8; or F3, F4, P3, and P4; or F3, Cz, P3, and O1; or Fz, Cz, P3, and P4. In another example, electrodes can be at T3/T7, T4/T8, TP7, T5/P7, and T6/P8. In another example, electrodes can be at T3/T7, T4/T8, PO7, and PO8. In another example, electrodes can be at P3, P4, O1, and O2. In another example, electrodes can be at Cz, P3, Pz, and P4.

In an example, an electrode can be a capacitive electrode. In an example, an electrode can be a dry electrode. In an example, an electrode can be made with a low-conductivity material which has been doped, impregnated, or coated with a high-conductivity material. In an example, an electrode can comprise a dielectric layer of low-conductivity material between two layers of high-conductivity material. In an example, an electrode can comprise a layer of high-conductivity material between two layers of low-conductivity material. In an example, an electrode can comprise low-conductivity fibers and highly-conductive fibers which are braided or woven together.

In an example, an electrode can be made by printing high-conductivity ink onto a low-conductivity textile or fabric. In an example, an electrode can be made by printing a conductive elastomeric material onto a low-conductivity textile or fabric. In an example, an electrode can be made by melting or adhering elastomeric conductive material onto a low-conductivity textile or fabric. In an example, an electrode can be made by embroidering conductive material onto a low-conductivity textile or fabric. In an example, an electrode can be made by weaving, knitting, sewing, embroidering, layering, laminating, adhering, melting, fusing, printing, spraying, painting, or pressing electroconductive material into (or onto) a fabric or textile. In an example, electroconductive threads, fibers, yarns, strands, filaments, traces, and/or layers within a fabric or textile can be configured near a person's skin in order to receive electromagnetic energy.

In an example, an electrode can be attached to a wearable brain activity monitor using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper. In an example, an electrode can be attached to a wearable brain activity monitor by printing, laminating, adhering, embroidering, melting, and/or sewing electroconductive material. In an example, an electronically-functional fabric or textile with electrodes can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, electroconductive threads, yarns, fibers, strands, channels, and/or traces comprising electrodes can have shapes or configurations which are selected from the group consisting of: circular, elliptical, or other conic section; square, rectangular, hexagon, or other polygon; parallel; perpendicular; crisscrossed; nested; concentric; sinusoidal; undulating; zigzagged; and radial spokes.

In an example, an electronically-functional fabric or textile with electrodes can be created by printing, spraying, or otherwise depositing electroconductive ink or resin onto an otherwise non-conductive fabric or textile. In an example, an electronically-functional circuit with electrodes can be created as part of a wearable brain activity monitor by printing a conductive pattern with electroconductive ink or resin. In an example, an electronically-functional fabric or textile with electrodes can be created by laminating electro-conductive members onto a non-conductive substrate. In an example, an electronically-functional fabric or textile with electrodes can be created by embroidering a generally non-conductive fabric or textile member with electro-conductive members. In an example, an electronically-functional circuit with electrodes can be created for a wearable brain activity monitor by embroidering a conductive pattern with electroconductive thread.

In an example, an electrode can be made with a low-conductivity material selected from the group consisting of: acetate, acrylic, cotton, denim, elastane, latex, linen, Lycra™, neoprene, nylon, nylon, polyester, wool, silicone, polydimethylsiloxane (PDMS), silk, spandex, and rayon. In an example, an electrode can be made with a high-conductivity material selected from the group consisting of: aluminum or aluminum alloy; carbon nanotubes, graphene, or other carbon-based material; copper or copper alloy; gold; nickel; silver; and steel. In an example, an electrode can be made with polydimethylsiloxane (PDMS) which has been doped or impregnated with aluminum, carbon (in one or more various configurations and formulations), copper, gold, nickel, silver, or steel. In an example, an electrode can be made from polydimethylsiloxane (PDMS) and carbon nanotubes. In an example, an electrode can be made from polydimethylsiloxane (PDMS) and silver.

In an example, a pattern and/or change in electromagnetic brain activity can be a one-time pattern. In another example, a pattern of electromagnetic brain activity can repeat over time in a rhythmic manner. In an example, a method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods. In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, a method for identifying patterns and/or changes in electromagnetic brain activity can comprise finding the amplitude of waveform data from one or more electrodes during a period of time. In an example, a method can comprise identifying a significant change in the amplitude of waveform data from one or more electrodes. In an example, a method can comprise identifying significant changes in the relative wave amplitudes from one or more electrodes. In an example, a method can comprise identifying significant changes in the amplitude of electromagnetic signals recorded from a first region of the brain relative to the amplitude of electromagnetic signals recorded from a second region of the brain.

In an example, a method for identifying patterns and/or changes in electromagnetic brain activity can comprise finding a frequency or a frequency band of waveform and/or rhythmic brain activity data from one or more electrodes which repeats over time. In an example, Fourier Transform methods can be used to find a frequency or a frequency band of waveform and/or rhythmic data which repeats over time. In an example, a method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a method for identifying patterns and/or changes in electromagnetic brain activity can comprise identifying significant changes in the amplitude, power level, phase, frequency, covariation, entropy, and/or oscillation of waveform data from one or more electrodes. In an example, a method can comprise identifying significant changes in the amplitude, power level, phase, frequency, covariation, entropy, and/or oscillation of waveform data within a selected frequency band. In an example, a method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example a sensor-positioning member (e.g. frame) of a wearable brain activity device can comprise a posterior-to-anterior series of right-to-left-side loops (e.g. arms or branches), wherein each loop is configured to span a person's head from their right side to their left side, or vice versa. In an example, this series of loops can originate on the right side of a person's head, diverge as the loops span around the head from right to left, and then reconverge on the left side of the head, or vice versa. In this example, there are three loops in a posterior-to-anterior series of loops. In an example, there can be four or more loops in a series.

In an example, loops in a posterior-to-anterior series of loops can converge at two loop convergence locations, one on the right side and one on the left side a person's head. In an example, each loop convergence location can be within 1 inch of an ear. In an example, each convergence location can be within 3 inches of an ear. In an example, a loop convergence location can be above an ear. In an example, a loop convergence location can be anterior to an ear. In an example, a loop convergence location can be posterior relative to an ear.

In an example, a posterior-to-anterior series of right-to-left loops can comprise three loops (e.g. arms or branches) which originate on the right side of a person's head, diverge as they loop around the head from right to left, and then reconverge on the left side of the person's head. In an example, a posterior-to-anterior series of right-to-left loops can comprise: a posterior ("rear") loop which originates on the right side of a person's head, loops around the rear of the head, and then terminates on the left side of the head; a middle ("top") loop which originates on the right side of a person's head, loops around the top of the head, and then ends on the left side of the head; and an anterior ("front") loop which originates on the right side of the head, loops around the front of the head, and then ends on the left side of the head.

In an example, the middle and posterior loops of a three-loop posterior-to-anterior series of right-to-left loops can form a forward-facing angle as they intersect. In an example, this forward-facing angle can be between 10 and 45 degrees or between 40 and 90 degrees. In an example, this angle can be between 90 degrees. In an example, this angle can be between 90 and 135 degrees. In an example, the anterior and middle loops of a three-loop posterior-to-anterior series of right-to-left loops can form a forward-facing angle as they intersect. In an example, this forward-facing angle can be between 10 and 45 degrees or between 40 and 90 degrees. In an example, this angle can be between 90 degrees. In an example, this can be between 90 and 135 degrees. In an example, the intersection angles between posterior, middle, and anterior loops in a wearable brain activity device can be adjusted (e.g. unlocked, changed, and then relocked).

In an example, the most anterior loop in a posterior-to-anterior series of right-to-left loops in the frame of a wearable brain activity device can span a person's forehead. In an example, the most anterior loop can hold two or more electrodes on a person's forehead. In an example, the most anterior loop can hold electrodes at two or more locations selected from the group consisting of: Fp1, Fpz, and Fp2. In an example, the most anterior loop can hold electrodes at two or more locations selected from the group consisting of: Fp1, Fpz, and Fp2. AF7, AF3, AFz, AF4, and AF8.

In an example, an auditory user interface of a wearable brain activity device can perform a noise cancellation and/or noise masking function. In an example, a speaker or other sound-creating member of a device can emit white noise, pink noise, or brown noise to mask environmental noise, mask a tinnitus sound, or generally help a person to get to sleep. In an example, a speaker or other sound-creating member of a device can emit noise with a random pattern and/or high degree of spectral variation to mask environmental noise, mask a tinnitus sound, or generally help a person to get to sleep. In an example, a speaker or other sound-creating member of a device can play lectures on actuarial science. In an example, a speaker or other sound-creating member of a device can create sounds in a selected frequency range which matches the frequency range of a particular environmental noise or a tinnitus sound which the person wishes to mask. In an example, a speaker or other sound-creating member of a device can create sounds with a frequency and phase (e.g. opposite phase) designed to cancel environmental or tinnitus sounds.

In an example, an auditory user interface of a wearable brain activity device can perform a brainwave entrainment and/or synchronization function. Entrainment is a tendency toward synchronization among proximal physical and biological systems. This synchronization occurs through interaction between proximal systems. Like acoustic waves, brainwaves also have frequency, amplitude, and periodicity. In an example, a speaker or other sound-creating member of a device can create sound waves with selected frequencies, amplitudes, and/or periodicities which can influence a person's brain activity. In an example, these sound waves can promote a desired state of neural activity. For example, as a person falls asleep, the frequencies of their brainwaves tend to decrease. In an example, a speaker or other sound-creating member of a device can produce sounds which help to guide a person's brain activity toward slower brainwaves.

In an example, this device can create sounds which, in interaction with a person's brainwaves, improve the person's sleep.

In an example, specific patterns of electromagnetic brain activity can be analyzed and identified using one or more methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; carlavian curve analysis (CCA); non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method. Relevant example variations discussed elsewhere in this disclosure or in priority-linked disclosures can also be applied to the example shown in this figure, but are not repeated here in order to reduce narrative redundancy.

Figure 3:
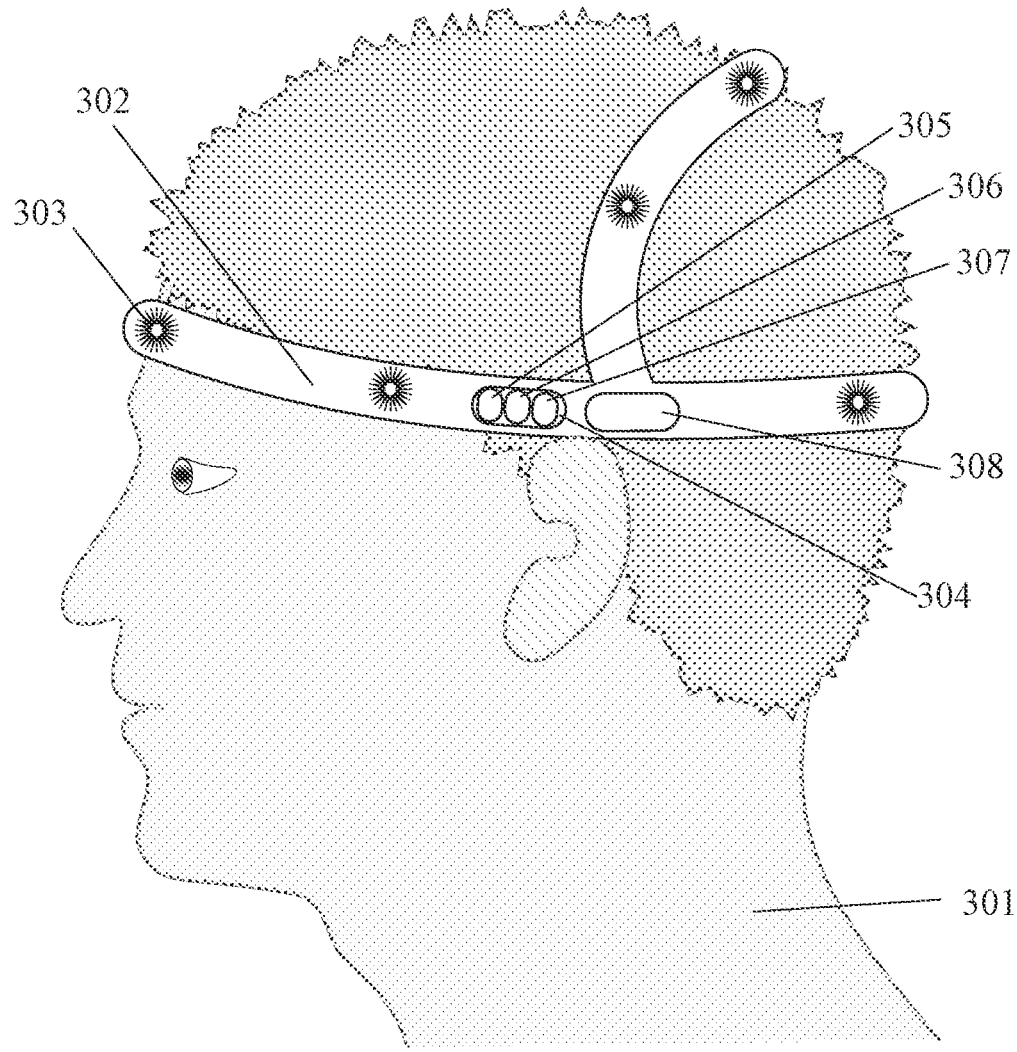
FIG. 3 shows another example of a wearable brain activity monitor with a ring portion around a person's head and an arc portion which loops over the person's head, wherein this example includes an auditory user interface such as a speaker or vibrating member.

FIG. 3 shows a left-side view of an example of another wearable brain activity monitor comprising a head-worn sensor-positioning member (e.g. frame) 302 which is configured to position a plurality of electrodes or other brain activity sensors including 303 at selected locations on the person's 301 head. In this example, sensor-positioning member (e.g. frame) (e.g. frame) 302 is assumed to be substantially symmetric with respect to the left side (shown) and the right side (not shown) of the person's head. This monitor further comprises control unit 304, which need not be replicated on the right side.

In this example, sensor-positioning member (e.g. frame) (e.g. frame) 302 comprises: a ring portion which encircles the top of the person's head in a manner like the rim of a cap; and an arc portion (e.g. branch or arm) which loops over the top of the person's head in a manner like the upper portion of a pair of headphones. In this example, these two portions (e.g. branches or arms) are joined on the left side and right side at locations just over the person's left ear and right ear, respectively. In an example, this device can comprise an array of electrodes or other brain activity sensors which are located substantially at the following set of placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8—or a subset of these sites.

In this example, control unit 304 further comprises: a data processing component 305; a power source (or transducer) 306; and a data transmitting (and receiving) component 307. In this example, the device further comprises a user interface 308. In an example, user interface 308 can be an auditory interface. In an example, user interface 308 can provide auditory biofeedback and/or neurofeedback. In an example, user interface 308 can comprise a speaker. In an example, interface 308 can comprise a vibrating member. In an example, biofeedback can be embodied in vibrations. In an example, interface 308 can comprise a MEMS actuator. In an example, an interactive audio signal can change from a first sound pattern to a second sound pattern as a person's brain activity changes from a first pattern to a second pattern. In an example, sound tones can help to change a person's brain activity pattern from a first pattern to a second pattern.

In an example, Delta brainwaves or other rhythmic, cyclical, and/or repeating electromagnetic signals associated with brain activity can be measured and analyzed within a frequency band of 0.5-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific electrode site, a specific electrode channel, and/or a specific montage of channels.

In an example, a ring portion (which goes around a person's head) of this device can be circular. In an example, a ring portion can have a shape selected from the group consisting of: circle, ellipse, and oval. In an example, a ring portion can have vertical undulations or waves around a central circumferential axis, wherein the central circumferential axis is circular, elliptical, or oval. In an example, a ring portion can have horizontal and/or radial undulations or waves around a central circumferential axis, wherein the central circumferential axis is circular, elliptical, or oval. In an example, undulations or waves can be sinusoidal. In an example, a ring portion can have an ascending-and-descending wave over (and around) a person's ear. In an example, such an ascending-and-descending wave can be sinusoidal.

In an example, a ring portion can be generally circular or elliptical, but have an upward (concave) curved portion over (and around) the person's ear. In an example, a "ring-fitting plane" can be defined as the plane which best fits the ring portion of this device. In an example, the ring-fitting plane can be horizontal (when a person stands upright). In an example, the ring-fitting plane can intersect a horizontal plane at a forward-facing acute angle. In an example, this angle can be between 5 and 20 degrees. In an example, this angle can be between 15 and 45 degrees.

In an example, an arc portion (which loops over the top of a person's head) of this device can have a forward-facing convexity. In an example, an arc portion can have a forward-facing concavity. In an example, an arc portion can loop over a portion of an anterior person's head (anterior relative to the top of the head or relative to the person's ear). In an example, an arc portion can loop over a posterior portion of a person's head (posterior relative to the top of the head or relative to the person's ear). In an example, an arc portion can intersect a ring portion of this device, forming a forward-facing acute angle at this intersection. In an example, this angle can be between 10 and 45 degrees. In an example, this angle can be between 40 and 80 degrees. In an example, an arc portion can have protrusions, prongs, and/or teeth which extend under a layer of hair in order to bring electrodes into better electromagnetic communication with the person's brain.

In an example, a sensor-positioning member (e.g. frame) can be a single continuous structure, even if it has different branches or arms. In an example, a sensor-positioning member (e.g. frame) can have multiple separately-made but connected pieces (such as branches and/or arms). In an example, these pieces can be connected with joints, hinges, or elastic straps. In an example, a sensor-positioning member (e.g. frame) can be flexible and/or elastic. In an example, the size, tension, and/or elasticity of a sensor-positioning member (e.g. frame) can be adjusted. In an example, the size, tension, and/or elasticity of a sensor-positioning member (e.g. frame) can be adjusted by a pneumatic mechanism and/or inflatable chamber. In an example, the size, tension, and/or elasticity of a sensor-positioning member (e.g. frame) can be adjusted by a hydraulic mechanism. In an example, the size, tension, and/or elasticity of a sensor-positioning member (e.g. frame) can be adjusted by a spring mechanism.

In an example, a brain activity monitor can have ten electrodes. In an example, these electrodes can be at the following sites FP1, FP2, F3, F4, T3/T7, T4/T8, P3, P4, O1, and O2. In an example, a brain activity monitor can have eight electrodes. In an example, these electrodes can be at: F3, F4, T3/T7, Cz, T4/T8, P3, Pz, and P4; or F3, F4, C3, C4, Cz, Pz, O1, and O2; or Fz, Cz, T5/P7, P3, Pz, P4, T6/P8, and Oz. In an example, a brain activity monitor can have seven electrodes. In an example, these electrodes can be at: FP1, FP2, Fz, C3, C4, Cz, and Pz; or F3, F4, Cz, P3, P4, O1, and O2. In an example, a brain activity monitor can have six electrodes. In an example, electrodes can be at: FP1, FP2, F7, F8, T3/T7, and T4/T8; or F3, F4, P3, P4, O1, and O2; or F3, F4, Cz, P2, O1, and O2; or F3, F8, T3/T7, T4/T8, T5/P7, and T6/P8; or FC3, T3/T7, C3, C4, Cz, and P3; or T3/T7, T4/T8, T5/P7, T6/P8, O1, and O2. In an example, a brain activity monitor can have five electrodes. In an example, electrodes can be at AFz, F3, F4, CP5, and CP6; or F3, F4, Cz, P3, and P4; or T3/T7, Cz, T4/T8, CP3, and CP4. In an example, a brain activity monitor can have four electrodes at FP1, FP2, F7, and F8; or AF7, AF8, T3/T7, and T4/T8; or F7, F3, F4, and F8; or F7, F8, T3/T7, and T4/T8; or F3, F4, P3, and P4; or F3, Cz, P3, and O1; or Fz, Cz, P3, and P4. In another example, electrodes can be at T3/T7, T4/T8, TP7, T5/P7, and T6/P8. In another example, electrodes can be at T3/T7, T4/T8, PO7, and PO8. In another example, electrodes can be at P3, P4, O1, and O2. In another example, electrodes can be at Cz, P3, Pz, and P4.

In an example, an electrode can be a capacitive electrode. In an example, an electrode can be a dry electrode. In an example, an electrode can be made with a low-conductivity material which has been doped, impregnated, or coated with a high-conductivity material. In an example, an electrode can comprise a dielectric layer of low-conductivity material between two layers of high-conductivity material. In an example, an electrode can comprise a layer of high-conductivity material between two layers of low-conductivity material. In an example, an electrode can comprise low-conductivity fibers and highly-conductive fibers which are braided or woven together.

In an example, an electrode can be made by printing high-conductivity ink onto a low-conductivity textile or fabric. In an example, an electrode can be made by printing a conductive elastomeric material onto a low-conductivity textile or fabric. In an example, an electrode can be made by melting or adhering elastomeric conductive material onto a low-conductivity textile or fabric. In an example, an electrode can be made by embroidering conductive material onto a low-conductivity textile or fabric. In an example, an electrode can be made by weaving, knitting, sewing, embroidering, layering, laminating, adhering, melting, fusing, printing, spraying, painting, or pressing electroconductive material into (or onto) a fabric or textile. In an example, electroconductive threads, fibers, yarns, strands, filaments, traces, and/or layers within a fabric or textile can be configured near a person's skin in order to receive electromagnetic energy.

In an example, an electrode can be attached to a wearable brain activity monitor using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper. In an example, an electrode can be attached to a wearable brain activity monitor by printing, laminating, adhering, embroidering, melting, and/or sewing electroconductive material. In an example, an electronically-functional fabric or textile with electrodes can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, electroconductive threads, yarns, fibers, strands, channels, and/or traces comprising electrodes can have shapes or configurations which are selected from the group consisting of: circular, elliptical, or other conic section; square, rectangular, hexagon, or other polygon; parallel; perpendicular; crisscrossed; nested; concentric; sinusoidal; undulating; zigzagged; and radial spokes.

In an example, an electronically-functional fabric or textile with electrodes can be created by printing, spraying, or otherwise depositing electroconductive ink or resin onto an otherwise non-conductive fabric or textile. In an example, an electronically-functional circuit with electrodes can be created as part of a wearable brain activity monitor by printing a conductive pattern with electroconductive ink or resin. In an example, an electronically-functional fabric or textile with electrodes can be created by laminating electro-conductive members onto a non-conductive substrate. In an example, an electronically-functional fabric or textile with electrodes can be created by embroidering a generally non-conductive fabric or textile member with electro-conductive members. In an example, an electronically-functional circuit with electrodes can be created for a wearable brain activity monitor by embroidering a conductive pattern with electroconductive thread.

In an example, an electrode can be made with a low-conductivity material selected from the group consisting of: acetate, acrylic, cotton, denim, elastane, latex, linen, Lycra™, neoprene, nylon, nylon, polyester, wool, silicone, polydimethylsiloxane (PDMS), silk, spandex, and rayon. In an example, an electrode can be made with a high-conductivity material selected from the group consisting of: aluminum or aluminum alloy; carbon nanotubes, graphene, or other carbon-based material; copper or copper alloy; gold; nickel; silver; and steel. In an example, an electrode can be made with polydimethylsiloxane (PDMS) which has been doped or impregnated with aluminum, carbon (in one or more various configurations and formulations), copper, gold, nickel, silver, or steel. In an example, an electrode can be made from polydimethylsiloxane (PDMS) and carbon nanotubes. In an example, an electrode can be made from polydimethylsiloxane (PDMS) and silver.

In an example, a pattern and/or change in electromagnetic brain activity can be a one-time pattern. In another example, a pattern of electromagnetic brain activity can repeat over time in a rhythmic manner. In an example, a method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods. In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, a method for identifying patterns and/or changes in electromagnetic brain activity can comprise finding the amplitude of waveform data from one or more electrodes during a period of time. In an example, a method can comprise identifying a significant change in the amplitude of waveform data from one or more electrodes. In an example, a method can comprise identifying significant changes in the relative wave amplitudes from one or more electrodes. In an example, a method can comprise identifying significant changes in the amplitude of electromagnetic signals recorded from a first region of the brain relative to the amplitude of electromagnetic signals recorded from a second region of the brain.

In an example, a method for identifying patterns and/or changes in electromagnetic brain activity can comprise finding a frequency or a frequency band of waveform and/or rhythmic brain activity data from one or more electrodes which repeats over time. In an example, Fourier Transform methods can be used to find a frequency or a frequency band of waveform and/or rhythmic data which repeats over time. In an example, a method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a method for identifying patterns and/or changes in electromagnetic brain activity can comprise identifying significant changes in the amplitude, power level, phase, frequency, covariation, entropy, and/or oscillation of waveform data from one or more electrodes. In an example, a method can comprise identifying significant changes in the amplitude, power level, phase, frequency, covariation, entropy, and/or oscillation of waveform data within a selected frequency band. In an example, a method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example a sensor-positioning member (e.g. frame) of a wearable brain activity device can comprise a posterior-to-anterior series of right-to-left-side loops (e.g. arms or branches), wherein each loop is configured to span a person's head from their right side to their left side, or vice versa. In an example, this series of loops can originate on the right side of a person's head, diverge as the loops span around the head from right to left, and then reconverge on the left side of the head, or vice versa. In this example, there are three loops in a posterior-to-anterior series of loops. In an example, there can be four or more loops in a series.

In an example, loops in a posterior-to-anterior series of loops can converge at two loop convergence locations, one on the right side and one on the left side a person's head. In an example, each loop convergence location can be within 1 inch of an ear. In an example, each convergence location can be within 3 inches of an ear. In an example, a loop convergence location can be above an ear. In an example, a loop convergence location can be anterior to an ear. In an example, a loop convergence location can be posterior relative to an ear.

In an example, a posterior-to-anterior series of right-to-left loops can comprise three loops (e.g. arms or branches) which originate on the right side of a person's head, diverge as they loop around the head from right to left, and then reconverge on the left side of the person's head. In an example, a posterior-to-anterior series of right-to-left loops can comprise: a posterior ("rear") loop which originates on the right side of a person's head, loops around the rear of the head, and then terminates on the left side of the head; a middle ("top") loop which originates on the right side of a person's head, loops around the top of the head, and then ends on the left side of the head; and an anterior ("front") loop which originates on the right side of the head, loops around the front of the head, and then ends on the left side of the head.

In an example, the middle and posterior loops of a three-loop posterior-to-anterior series of right-to-left loops can form a forward-facing angle as they intersect. In an example, this forward-facing angle can be between 10 and 45 degrees or between 40 and 90 degrees. In an example, this angle can be between 90 degrees. In an example, this angle can be between 90 and 135 degrees. In an example, the anterior and middle loops of a three-loop posterior-to-anterior series of right-to-left loops can form a forward-facing angle as they intersect. In an example, this forward-facing angle can be between 10 and 45 degrees or between 40 and 90 degrees. In an example, this angle can be between 90 degrees. In an example, this can be between 90 and 135 degrees. In an example, the intersection angles between posterior, middle, and anterior loops in a wearable brain activity device can be adjusted (e.g. unlocked, changed, and then relocked).

In an example, the most anterior loop in a posterior-to-anterior series of right-to-left loops in the frame of a wearable brain activity device can span a person's forehead. In an example, the most anterior loop can hold two or more electrodes on a person's forehead. In an example, the most anterior loop can hold electrodes at two or more locations selected from the group consisting of: Fp1, Fpz, and Fp2. In an example, the most anterior loop can hold electrodes at two or more locations selected from the group consisting of: Fp1, Fpz, and Fp2. AF7, AF3, AFz, AF4, and AF8.

In an example, an auditory user interface of a wearable brain activity device can perform a noise cancellation and/or noise masking function. In an example, a speaker or other sound-creating member of a device can emit white noise, pink noise, or brown noise to mask environmental noise, mask a tinnitus sound, or generally help a person to get to sleep. In an example, a speaker or other sound-creating member of a device can emit noise with a random pattern and/or high degree of spectral variation to mask environmental noise, mask a tinnitus sound, or generally help a person to get to sleep. In an example, a speaker or other sound-creating member of a device can play lectures on actuarial science. In an example, a speaker or other sound-creating member of a device can create sounds in a selected frequency range which matches the frequency range of a particular environmental noise or a tinnitus sound which the person wishes to mask. In an example, a speaker or other sound-creating member of a device can create sounds with a frequency and phase (e.g. opposite phase) designed to cancel environmental or tinnitus sounds.

In an example, an auditory user interface of a wearable brain activity device can perform a brainwave entrainment and/or synchronization function. Entrainment is a tendency toward synchronization among proximal physical and biological systems. This synchronization occurs through interaction between proximal systems. Like acoustic waves, brainwaves also have frequency, amplitude, and periodicity. In an example, a speaker or other sound-creating member of a device can create sound waves with selected frequencies, amplitudes, and/or periodicities which can influence a person's brain activity. In an example, these sound waves can promote a desired state of neural activity. For example, as a person falls asleep, the frequencies of their brainwaves tend to decrease. In an example, a speaker or other sound-creating member of a device can produce sounds which help to guide a person's brain activity toward slower brainwaves. In an example, this device can create sounds which, in interaction with a person's brainwaves, improve the person's sleep.

In an example, specific patterns of electromagnetic brain activity can be analyzed and identified using one or more methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; carlavian curve analysis (CCA); non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method.

Relevant example variations discussed elsewhere in this disclosure or in priority-linked disclosures can also be applied to the example shown in this figure, but are not repeated here in order to reduce narrative redundancy.

Figure 4:
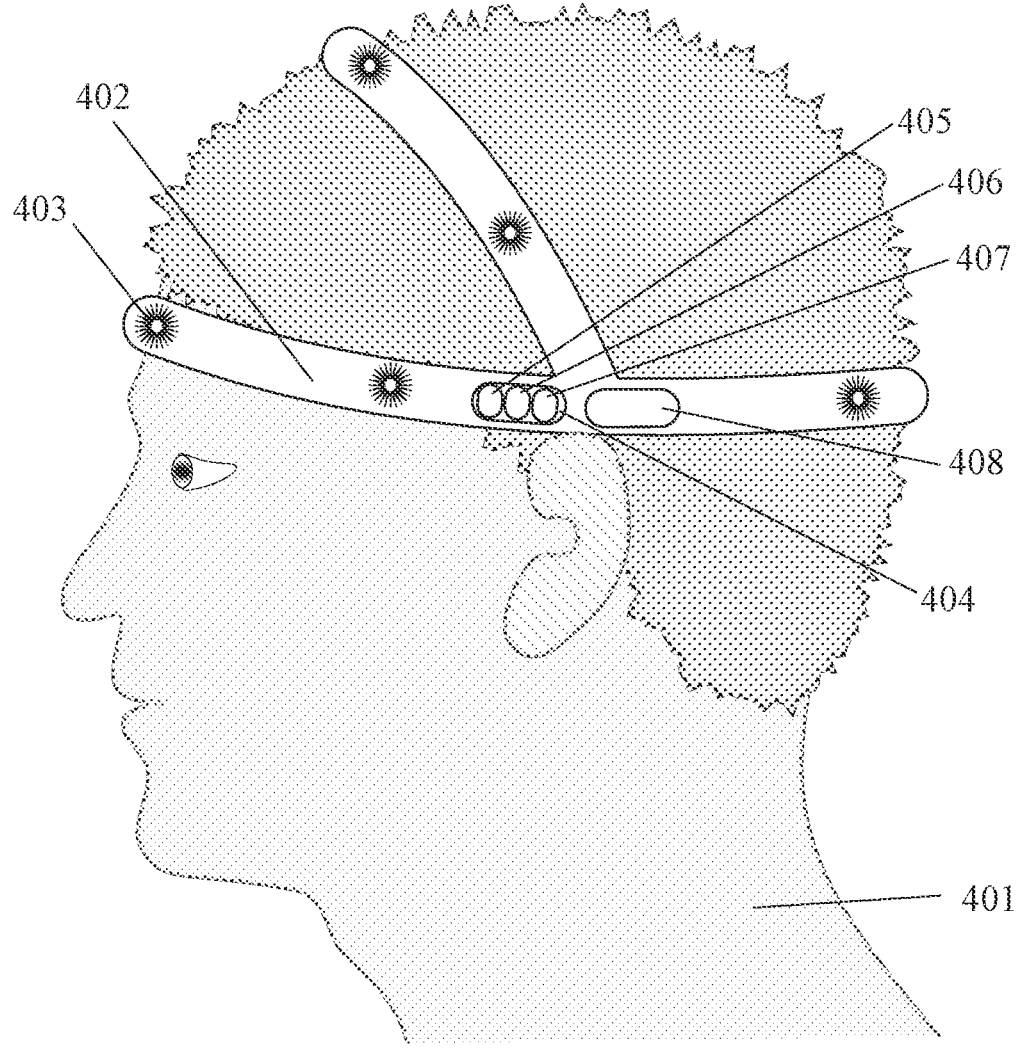
FIG. 4 shows another example of a wearable brain activity monitor with a ring portion around a person's head and an arc portion which loops over the person's head, wherein this example includes an auditory user interface such as a speaker or vibrating member.

FIG. 4 shows a left-side view of an example of another wearable brain activity monitor comprising a head-worn sensor-positioning member (e.g. frame) (e.g. frame) 402 which is configured to position a plurality of electrodes or other brain activity sensors including 403 at selected locations on the person's 401 head. In this example, sensor-positioning member (e.g. frame) (e.g. frame) 402 is assumed to be substantially symmetric with respect to the left side (shown) and the right side (not shown) of the person's head. This monitor further comprises control unit 404, which need not be replicated on the right side.

In this example, sensor-positioning member (e.g. frame) 402 comprises: a ring portion which encircles the top of the person's head in a manner like the rim of a cap; and an arc portion (e.g. branch or arm) which loops over the top of the person's head. In this example, these two portions (e.g. branches or arms) are joined on the left side and right side at locations just over the person's left ear and right ear, respectively. In an example, this device can comprise an array of electrodes or other brain activity sensors which are located substantially at the following set of placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8—or a subset of these sites.

In this example, control unit 404 further comprises: a data processing component 405; a power source (or transducer) 406; and a data transmitting (and receiving) component 407. In this example, the device further comprises a user interface 408. In an example, user interface 408 can be an auditory interface. In an example, user interface 408 can provide auditory biofeedback and/or neurofeedback. In an example, user interface 408 can comprise a speaker. In an example, interface 408 can comprise a vibrating member. In an example, biofeedback can be embodied in vibrations. In an example, interface 408 can comprise a MEMS actuator. In an example, an interactive audio signal can change from a first sound pattern to a second sound pattern as a person's brain activity changes from a first pattern to a second pattern. In an example, sound tones can help to change a person's brain activity pattern from a first pattern to a second pattern.

In an example, Delta brainwaves or other rhythmic, cyclical, and/or repeating electromagnetic signals associated with brain activity can be measured and analyzed within a frequency band of 0.5-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific electrode site, a specific electrode channel, and/or a specific montage of channels.

In an example, a ring portion (which goes around a person's head) of this device can be circular. In an example, a ring portion can have a shape selected from the group consisting of: circle, ellipse, and oval. In an example, a ring portion can have vertical undulations or waves around a central circumferential axis, wherein the central circumferential axis is circular, elliptical, or oval. In an example, a ring portion can have horizontal and/or radial undulations or waves around a central circumferential axis, wherein the central circumferential axis is circular, elliptical, or oval. In an example, undulations or waves can be sinusoidal. In an example, a ring portion can have an ascending-and-descending wave over (and around) a person's ear. In an example, such an ascending-and-descending wave can be sinusoidal.

In an example, a ring portion can be generally circular or elliptical, but have an upward (concave) curved portion over (and around) the person's ear. In an example, a "ring-fitting plane" can be defined as the plane which best fits the ring portion of this device. In an example, the ring-fitting plane can be horizontal (when a person stands upright). In an example, the ring-fitting plane can intersect a horizontal plane at a forward-facing acute angle. In an example, this angle can be between 5 and 20 degrees. In an example, this angle can be between 15 and 45 degrees.

In an example, an arc portion (which loops over the top of a person's head) of this device can have a forward-facing convexity. In an example, an arc portion can have a forward-facing concavity. In an example, an arc portion can loop over a portion of an anterior person's head (anterior relative to the top of the head or relative to the person's ear). In an example, an arc portion can loop over a posterior portion of a person's head (posterior relative to the top of the head or relative to the person's ear). In an example, an arc portion can intersect a ring portion of this device, forming a forward-facing acute angle at this intersection. In an example, this angle can be between 10 and 45 degrees. In an example, this angle can be between 40 and 80 degrees. In an example, an arc portion can have protrusions, prongs, and/or teeth which extend under a layer of hair in order to bring electrodes into better electromagnetic communication with the person's brain.

In an example, a sensor-positioning member (e.g. frame) can be a single continuous structure, even if it has different branches or arms. In an example, a sensor-positioning member (e.g. frame) can have multiple separately-made but connected pieces (such as branches and/or arms). In an example, these pieces can be connected with joints, hinges, or elastic straps. In an example, a sensor-positioning member (e.g. frame) can be flexible and/or elastic. In an example, the size, tension, and/or elasticity of a sensor-positioning member (e.g. frame) can be adjusted. In an example, the size, tension, and/or elasticity of a sensor-positioning member (e.g. frame) can be adjusted by a pneumatic mechanism and/or inflatable chamber. In an example, the size, tension, and/or elasticity of a sensor-positioning member (e.g. frame) can be adjusted by a hydraulic mechanism. In an example, the size, tension, and/or elasticity of a sensor-positioning member (e.g. frame) can be adjusted by a spring mechanism.

In an example, a brain activity monitor can have ten electrodes. In an example, these electrodes can be at the following sites FP1, FP2, F3, F4, T3/T7, T4/T8, P3, P4, O1, and O2. In an example, a brain activity monitor can have eight electrodes. In an example, these electrodes can be at: F3, F4, T3/T7, Cz, T4/T8, P3, Pz, and P4; or F3, F4, C3, C4, Cz, Pz, O1, and O2; or Fz, Cz, T5/P7, P3, Pz, P4, T6/P8, and Oz. In an example, a brain activity monitor can have seven electrodes. In an example, these electrodes can be at: FP1, FP2, Fz, C3, C4, Cz, and Pz; or F3, F4, Cz, P3, P4, O1, and O2. In an example, a brain activity monitor can have six electrodes. In an example, electrodes can be at: FP1, FP2, F7, F8, T3/T7, and T4/T8; or F3, F4, P3, P4, O1, and O2; or F3, F4, Cz, P2, O1, and O2; or F3, F8, T3/T7, T4/T8, T5/P7, and T6/P8; or FC3, T3/T7, C3, C4, Cz, and P3; or T3/T7, T4/T8, T5/P7, T6/P8, O1, and O2. In an example, a brain activity monitor can have five electrodes. In an example, electrodes can be at AFz, F3, F4, CP5, and CP6; or F3, F4, Cz, P3, and P4; or T3/T7, Cz, T4/T8, CP3, and CP4. In an example, a brain activity monitor can have four electrodes at FP1, FP2, F7, and F8; or AF7, AF8, T3/T7, and T4/T8; or F7, F3, F4, and F8; or F7, F8, T3/T7, and T4/T8; or F3, F4, P3, and P4; or F3, Cz, P3, and O1; or Fz, Cz, P3, and P4. In another example, electrodes can be at T3/T7, T4/T8, TP7, T5/P7, and T6/P8. In another example, electrodes can be at T3/T7, T4/T8, PO7, and PO8. In another example, electrodes can be at P3, P4, O1, and O2. In another example, electrodes can be at Cz, P3, Pz, and P4.

In an example, an electrode can be a capacitive electrode. In an example, an electrode can be a dry electrode. In an example, an electrode can be made with a low-conductivity material which has been doped, impregnated, or coated with a high-conductivity material. In an example, an electrode can comprise a dielectric layer of low-conductivity material between two layers of high-conductivity material. In an example, an electrode can comprise a layer of high-conductivity material between two layers of low-conductivity material. In an example, an electrode can comprise low-conductivity fibers and highly-conductive fibers which are braided or woven together.

In an example, an electrode can be made by printing high-conductivity ink onto a low-conductivity textile or fabric. In an example, an electrode can be made by printing a conductive elastomeric material onto a low-conductivity textile or fabric. In an example, an electrode can be made by melting or adhering elastomeric conductive material onto a low-conductivity textile or fabric. In an example, an electrode can be made by embroidering conductive material onto a low-conductivity textile or fabric. In an example, an electrode can be made by weaving, knitting, sewing, embroidering, layering, laminating, adhering, melting, fusing, printing, spraying, painting, or pressing electroconductive material into (or onto) a fabric or textile. In an example, electroconductive threads, fibers, yarns, strands, filaments, traces, and/or layers within a fabric or textile can be configured near a person's skin in order to receive electromagnetic energy.

In an example, an electrode can be attached to a wearable brain activity monitor using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper. In an example, an electrode can be attached to a wearable brain activity monitor by printing, laminating, adhering, embroidering, melting, and/or sewing electroconductive material. In an example, an electronically-functional fabric or textile with electrodes can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, electroconductive threads, yarns, fibers, strands, channels, and/or traces comprising electrodes can have shapes or configurations which are selected from the group consisting of: circular, elliptical, or other conic section; square, rectangular, hexagon, or other polygon; parallel; perpendicular; crisscrossed; nested; concentric; sinusoidal; undulating; zigzagged; and radial spokes.

In an example, an electronically-functional fabric or textile with electrodes can be created by printing, spraying, or otherwise depositing electroconductive ink or resin onto an otherwise non-conductive fabric or textile. In an example, an electronically-functional circuit with electrodes can be created as part of a wearable brain activity monitor by printing a conductive pattern with electroconductive ink or resin. In an example, an electronically-functional fabric or textile with electrodes can be created by laminating electro-conductive members onto a non-conductive substrate. In an example, an electronically-functional fabric or textile with electrodes can be created by embroidering a generally non-conductive fabric or textile member with electro-conductive members. In an example, an electronically-functional circuit with electrodes can be created for a wearable brain activity monitor by embroidering a conductive pattern with electroconductive thread.

In an example, an electrode can be made with a low-conductivity material selected from the group consisting of: acetate, acrylic, cotton, denim, elastane, latex, linen, Lycra™, neoprene, nylon, nylon, polyester, wool, silicone, polydimethylsiloxane (PDMS), silk, spandex, and rayon. In an example, an electrode can be made with a high-conductivity material selected from the group consisting of: aluminum or aluminum alloy; carbon nanotubes, graphene, or other carbon-based material; copper or copper alloy; gold; nickel; silver; and steel. In an example, an electrode can be made with polydimethylsiloxane (PDMS) which has been doped or impregnated with aluminum, carbon (in one or more various configurations and formulations), copper, gold, nickel, silver, or steel. In an example, an electrode can be made from polydimethylsiloxane (PDMS) and carbon nanotubes. In an example, an electrode can be made from polydimethylsiloxane (PDMS) and silver.

In an example, a pattern and/or change in electromagnetic brain activity can be a one-time pattern. In another example, a pattern of electromagnetic brain activity can repeat over time in a rhythmic manner. In an example, a method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods. In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, a method for identifying patterns and/or changes in electromagnetic brain activity can comprise finding the amplitude of waveform data from one or more electrodes during a period of time. In an example, a method can comprise identifying a significant change in the amplitude of waveform data from one or more electrodes. In an example, a method can comprise identifying significant changes in the relative wave amplitudes from one or more electrodes. In an example, a method can comprise identifying significant changes in the amplitude of electromagnetic signals recorded from a first region of the brain relative to the amplitude of electromagnetic signals recorded from a second region of the brain.

In an example, a method for identifying patterns and/or changes in electromagnetic brain activity can comprise finding a frequency or a frequency band of waveform and/or rhythmic brain activity data from one or more electrodes which repeats over time. In an example, Fourier Transform methods can be used to find a frequency or a frequency band of waveform and/or rhythmic data which repeats over time. In an example, a method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a method for identifying patterns and/or changes in electromagnetic brain activity can comprise identifying significant changes in the amplitude, power level, phase, frequency, covariation, entropy, and/or oscillation of waveform data from one or more electrodes. In an example, a method can comprise identifying significant changes in the amplitude, power level, phase, frequency, covariation, entropy, and/or oscillation of waveform data within a selected frequency band. In an example, a method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example a sensor-positioning member (e.g. frame) of a wearable brain activity device can comprise a posterior-to-anterior series of right-to-left-side loops (e.g. arms or branches), wherein each loop is configured to span a person's head from their right side to their left side, or vice versa. In an example, this series of loops can originate on the right side of a person's head, diverge as the loops span around the head from right to left, and then reconverge on the left side of the head, or vice versa. In this example, there are three loops in a posterior-to-anterior series of loops. In an example, there can be four or more loops in a series.

In an example, loops in a posterior-to-anterior series of loops can converge at two loop convergence locations, one on the right side and one on the left side a person's head. In an example, each loop convergence location can be within 1 inch of an ear. In an example, each convergence location can be within 3 inches of an ear. In an example, a loop convergence location can be above an ear. In an example, a loop convergence location can be anterior to an ear. In an example, a loop convergence location can be posterior relative to an ear.

In an example, a posterior-to-anterior series of right-to-left loops can comprise three loops (e.g. arms or branches) which originate on the right side of a person's head, diverge as they loop around the head from right to left, and then reconverge on the left side of the person's head. In an example, a posterior-to-anterior series of right-to-left loops can comprise: a posterior ("rear") loop which originates on the right side of a person's head, loops around the rear of the head, and then terminates on the left side of the head; a middle ("top") loop which originates on the right side of a person's head, loops around the top of the head, and then ends on the left side of the head; and an anterior ("front") loop which originates on the right side of the head, loops around the front of the head, and then ends on the left side of the head.

In an example, the middle and posterior loops of a three-loop posterior-to-anterior series of right-to-left loops can form a forward-facing angle as they intersect. In an example, this forward-facing angle can be between 10 and 45 degrees or between 40 and 90 degrees. In an example, this angle can be between 90 degrees. In an example, this angle can be between 90 and 135 degrees. In an example, the anterior and middle loops of a three-loop posterior-to-anterior series of right-to-left loops can form a forward-facing angle as they intersect. In an example, this forward-facing angle can be between 10 and 45 degrees or between 40 and 90 degrees. In an example, this angle can be between 90 degrees. In an example, this can be between 90 and 135 degrees. In an example, the intersection angles between posterior, middle, and anterior loops in a wearable brain activity device can be adjusted (e.g. unlocked, changed, and then relocked).

In an example, the most anterior loop in a posterior-to-anterior series of right-to-left loops in the frame of a wearable brain activity device can span a person's forehead. In an example, the most anterior loop can hold two or more electrodes on a person's forehead. In an example, the most anterior loop can hold electrodes at two or more locations selected from the group consisting of: Fp1, Fpz, and Fp2. In an example, the most anterior loop can hold electrodes at two or more locations selected from the group consisting of: Fp1, Fpz, and Fp2. AF7, AF3, AFz, AF4, and AF8.

In an example, an auditory user interface of a wearable brain activity device can perform a noise cancellation and/or noise masking function. In an example, a speaker or other sound-creating member of a device can emit white noise, pink noise, or brown noise to mask environmental noise, mask a tinnitus sound, or generally help a person to get to sleep. In an example, a speaker or other sound-creating member of a device can emit noise with a random pattern and/or high degree of spectral variation to mask environmental noise, mask a tinnitus sound, or generally help a person to get to sleep. In an example, a speaker or other sound-creating member of a device can play lectures on actuarial science. In an example, a speaker or other sound-creating member of a device can create sounds in a selected frequency range which matches the frequency range of a particular environmental noise or a tinnitus sound which the person wishes to mask. In an example, a speaker or other sound-creating member of a device can create sounds with a frequency and phase (e.g. opposite phase) designed to cancel environmental or tinnitus sounds.

In an example, an auditory user interface of a wearable brain activity device can perform a brainwave entrainment and/or synchronization function. Entrainment is a tendency toward synchronization among proximal physical and biological systems. This synchronization occurs through interaction between proximal systems. Like acoustic waves, brainwaves also have frequency, amplitude, and periodicity. In an example, a speaker or other sound-creating member of a device can create sound waves with selected frequencies, amplitudes, and/or periodicities which can influence a person's brain activity. In an example, these sound waves can promote a desired state of neural activity. For example, as a person falls asleep, the frequencies of their brainwaves tend to decrease. In an example, a speaker or other sound-creating member of a device can produce sounds which help to guide a person's brain activity toward slower brainwaves.

In an example, this device can create sounds which, in interaction with a person's brainwaves, improve the person's sleep.

In an example, specific patterns of electromagnetic brain activity can be analyzed and identified using one or more methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; carlavian curve analysis (CCA); non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method. Relevant example variations discussed elsewhere in this disclosure or in priority-linked disclosures can also be applied to the example shown in this figure, but are not repeated here in order to reduce narrative redundancy.

Figure 5:
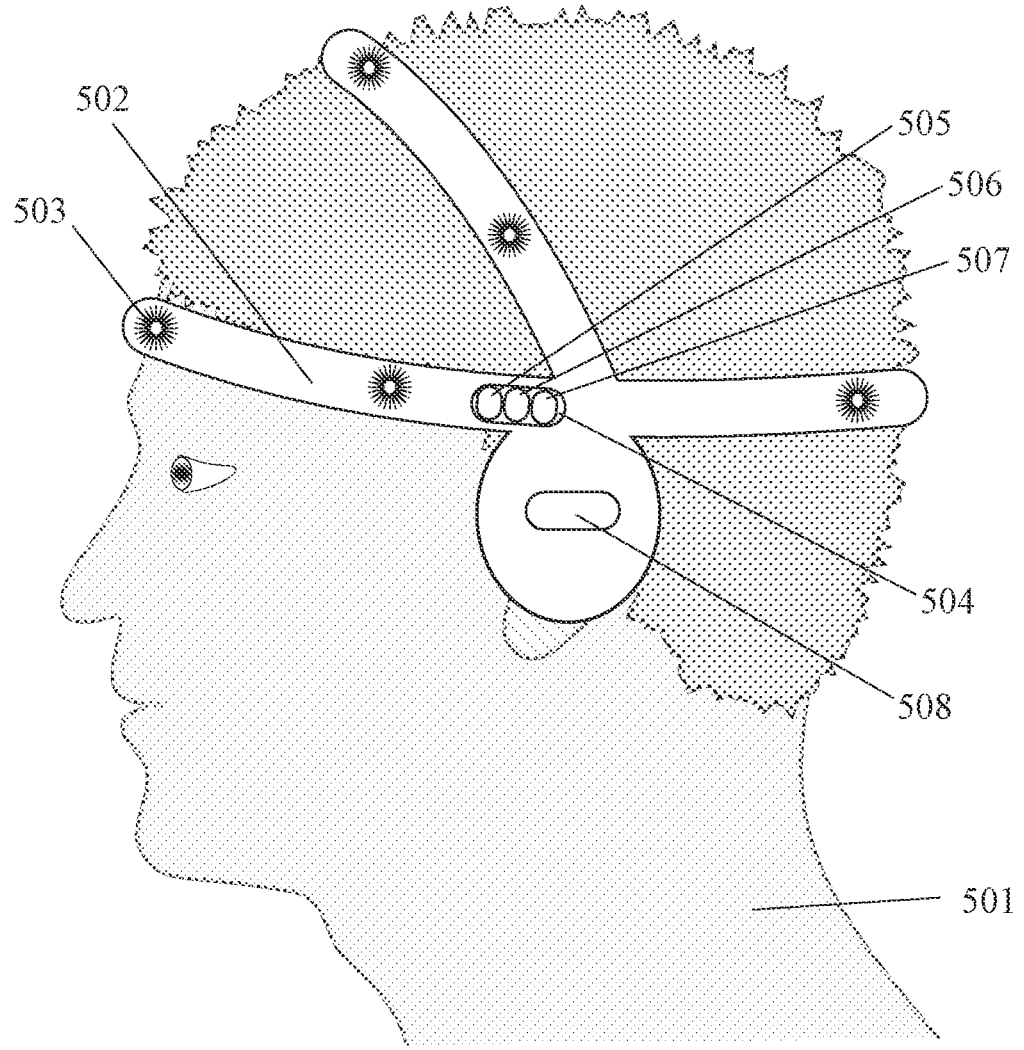
FIG. 5 shows an example of a wearable brain activity monitor with a ring portion around a person's head, an arc portion which loops over the person's head, and an ear-covering portion.

FIG. 5 shows a left-side view of an example of a wearable brain activity monitor comprising a head-worn sensor-positioning member (e.g. frame) 502 which is configured to position a plurality of electrodes or other brain activity sensors including 503 at selected locations on the person's 501 head. In this example, sensor-positioning member (e.g. frame) 502 is assumed to be substantially symmetric with respect to the left side (shown) and the right side (not shown) of the person's head. This monitor further comprises control unit 504, which need not be replicated on the right side.

In this example, sensor-positioning member (e.g. frame) 502 comprises: (a) a ring portion which encircles the top of the person's head in a manner like the rim of a cap; (b) an arc portion which loops over the top of the person's head; and (c) an ear-covering portion which is configured to cover the person's ear in a manner like the lower portion of a pair of headphones. In this example, these three portions are joined on the left side and right side at locations just over the person's left ear and right ear, respectively. In an example, this device can comprise an array of electrodes or other brain activity sensors which are located substantially at the following set of placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8—or a subset of these sites.

In this example, control unit 504 further comprises: a data processing component 505; a power source (or transducer) 506; and a data transmitting (and receiving) component 507. In this example, the device further comprises a user interface 508. In an example, user interface 508 can be an auditory interface. In an example, user interface 508 can provide auditory biofeedback and/or neurofeedback. In an example, user interface 508 can comprise a speaker. In an example, interface 508 can comprise a vibrating member. In an example, biofeedback can be embodied in vibrations. In an example, interface 508 can comprise a MEMS actuator. In an example, an interactive audio signal can change from a first sound pattern to a second sound pattern as a person's brain activity changes from a first pattern to a second pattern. In an example, sound tones can help to change a person's brain activity pattern from a first pattern to a second pattern.

In an example, Delta brainwaves or other rhythmic, cyclical, and/or repeating electromagnetic signals associated with brain activity can be measured and analyzed within a frequency band of 0.5-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific electrode site, a specific electrode channel, and/or a specific montage of channels.

In an example, a ring portion (which goes around a person's head) of this device can be circular. In an example, a ring portion can have a shape selected from the group consisting of: circle, ellipse, and oval. In an example, a ring portion can have vertical undulations or waves around a central circumferential axis, wherein the central circumferential axis is circular, elliptical, or oval. In an example, a ring portion can have horizontal and/or radial undulations or waves around a central circumferential axis, wherein the central circumferential axis is circular, elliptical, or oval. In an example, undulations or waves can be sinusoidal. In an example, a ring portion can have an ascending-and-descending wave over (and around) a person's ear. In an example, such an ascending-and-descending wave can be sinusoidal.

In an example, a ring portion can be generally circular or elliptical, but have an upward (concave) curved portion over (and around) the person's ear. In an example, a "ring-fitting plane" can be defined as the plane which best fits the ring portion of this device. In an example, the ring-fitting plane can be horizontal (when a person stands upright). In an example, the ring-fitting plane can intersect a horizontal plane at a forward-facing acute angle. In an example, this angle can be between 5 and 20 degrees. In an example, this angle can be between 15 and 45 degrees.

In an example, an arc portion (which loops over the top of a person's head) of this device can have a forward-facing convexity. In an example, an arc portion can have a forward-facing concavity. In an example, an arc portion can loop over a portion of an anterior person's head (anterior relative to the top of the head or relative to the person's ear). In an example, an arc portion can loop over a posterior portion of a person's head (posterior relative to the top of the head or relative to the person's ear). In an example, an arc portion can intersect a ring portion of this device, forming a forward-facing acute angle at this intersection. In an example, this angle can be between 10 and 45 degrees. In an example, this angle can be between 40 and 80 degrees. In an example, an arc portion can have protrusions, prongs, and/or teeth which extend under a layer of hair in order to bring electrodes into better electromagnetic communication with the person's brain.

In an example, a sensor-positioning member (e.g. frame) can be a single continuous structure, even if it has different branches or arms. In an example, a sensor-positioning member (e.g. frame) can have multiple separately-made but connected pieces (such as branches and/or arms). In an example, these pieces can be connected with joints, hinges, or elastic straps. In an example, a sensor-positioning member (e.g. frame) can be flexible and/or elastic. In an example, the size, tension, and/or elasticity of a sensor-positioning member (e.g. frame) can be adjusted. In an example, the size, tension, and/or elasticity of a sensor-positioning member (e.g. frame) can be adjusted by a pneumatic mechanism and/or inflatable chamber. In an example, the size, tension, and/or elasticity of a sensor-positioning member (e.g. frame) can be adjusted by a hydraulic mechanism. In an example, the size, tension, and/or elasticity of a sensor-positioning member (e.g. frame) can be adjusted by a spring mechanism.

In an example, a brain activity monitor can have ten electrodes. In an example, these electrodes can be at the following sites FP1, FP2, F3, F4, T3/T7, T4/T8, P3, P4, O1, and O2. In an example, a brain activity monitor can have eight electrodes. In an example, these electrodes can be at: F3, F4, T3/T7, Cz, T4/T8, P3, Pz, and P4; or F3, F4, C3, C4, Cz, Pz, O1, and O2; or Fz, Cz, T5/P7, P3, Pz, P4, T6/P8, and Oz. In an example, a brain activity monitor can have seven electrodes. In an example, these electrodes can be at: FP1, FP2, Fz, C3, C4, Cz, and Pz; or F3, F4, Cz, P3, P4, O1, and O2. In an example, a brain activity monitor can have six electrodes. In an example, electrodes can be at: FP1, FP2, F7, F8, T3/T7, and T4/T8; or F3, F4, P3, P4, O1, and O2; or F3, F4, Cz, P2, O1, and O2; or F3, F8, T3/T7, T4/T8, T5/P7, and T6/P8; or FC3, T3/T7, C3, C4, Cz, and P3; or T3/T7, T4/T8, T5/P7, T6/P8, O1, and O2. In an example, a brain activity monitor can have five electrodes. In an example, electrodes can be at AFz, F3, F4, CP5, and CP6; or F3, F4, Cz, P3, and P4; or T3/T7, Cz, T4/T8, CP3, and CP4. In an example, a brain activity monitor can have four electrodes at FP1, FP2, F7, and F8; or AF7, AF8, T3/T7, and T4/T8; or F7, F3, F4, and F8; or F7, F8, T3/T7, and T4/T8; or F3, F4, P3, and P4; or F3, Cz, P3, and O1; or Fz, Cz, P3, and P4. In another example, electrodes can be at T3/T7, T4/T8, TP7, T5/P7, and T6/P8. In another example, electrodes can be at T3/T7, T4/T8, PO7, and PO8. In another example, electrodes can be at P3, P4, O1, and O2. In another example, electrodes can be at Cz, P3, Pz, and P4.

In an example, an electrode can be a capacitive electrode. In an example, an electrode can be a dry electrode. In an example, an electrode can be made with a low-conductivity material which has been doped, impregnated, or coated with a high-conductivity material. In an example, an electrode can comprise a dielectric layer of low-conductivity material between two layers of high-conductivity material. In an example, an electrode can comprise a layer of high-conductivity material between two layers of low-conductivity material. In an example, an electrode can comprise low-conductivity fibers and highly-conductive fibers which are braided or woven together.

In an example, an electrode can be made by printing high-conductivity ink onto a low-conductivity textile or fabric. In an example, an electrode can be made by printing a conductive elastomeric material onto a low-conductivity textile or fabric. In an example, an electrode can be made by melting or adhering elastomeric conductive material onto a low-conductivity textile or fabric. In an example, an electrode can be made by embroidering conductive material onto a low-conductivity textile or fabric. In an example, an electrode can be made by weaving, knitting, sewing, embroidering, layering, laminating, adhering, melting, fusing, printing, spraying, painting, or pressing electroconductive material into (or onto) a fabric or textile. In an example, electroconductive threads, fibers, yarns, strands, filaments, traces, and/or layers within a fabric or textile can be configured near a person's skin in order to receive electromagnetic energy.

In an example, an electrode can be attached to a wearable brain activity monitor using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper. In an example, an electrode can be attached to a wearable brain activity monitor by printing, laminating, adhering, embroidering, melting, and/or sewing electroconductive material. In an example, an electronically-functional fabric or textile with electrodes can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, electroconductive threads, yarns, fibers, strands, channels, and/or traces comprising electrodes can have shapes or configurations which are selected from the group consisting of: circular, elliptical, or other conic section; square, rectangular, hexagon, or other polygon; parallel; perpendicular; crisscrossed; nested; concentric; sinusoidal; undulating; zigzagged; and radial spokes.

In an example, an electronically-functional fabric or textile with electrodes can be created by printing, spraying, or otherwise depositing electroconductive ink or resin onto an otherwise non-conductive fabric or textile. In an example, an electronically-functional circuit with electrodes can be created as part of a wearable brain activity monitor by printing a conductive pattern with electroconductive ink or resin. In an example, an electronically-functional fabric or textile with electrodes can be created by laminating electro-conductive members onto a non-conductive substrate. In an example, an electronically-functional fabric or textile with electrodes can be created by embroidering a generally non-conductive fabric or textile member with electro-conductive members. In an example, an electronically-functional circuit with electrodes can be created for a wearable brain activity monitor by embroidering a conductive pattern with electroconductive thread.

In an example, an electrode can be made with a low-conductivity material selected from the group consisting of: acetate, acrylic, cotton, denim, elastane, latex, linen, Lycra™, neoprene, nylon, nylon, polyester, wool, silicone, polydimethylsiloxane (PDMS), silk, spandex, and rayon. In an example, an electrode can be made with a high-conductivity material selected from the group consisting of: aluminum or aluminum alloy; carbon nanotubes, graphene, or other carbon-based material; copper or copper alloy; gold; nickel; silver; and steel. In an example, an electrode can be made with polydimethylsiloxane (PDMS) which has been doped or impregnated with aluminum, carbon (in one or more various configurations and formulations), copper, gold, nickel, silver, or steel. In an example, an electrode can be made from polydimethylsiloxane (PDMS) and carbon nanotubes. In an example, an electrode can be made from polydimethylsiloxane (PDMS) and silver.

In an example, a pattern and/or change in electromagnetic brain activity can be a one-time pattern. In another example, a pattern of electromagnetic brain activity can repeat over time in a rhythmic manner. In an example, a method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods. In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, a method for identifying patterns and/or changes in electromagnetic brain activity can comprise finding the amplitude of waveform data from one or more electrodes during a period of time. In an example, a method can comprise identifying a significant change in the amplitude of waveform data from one or more electrodes. In an example, a method can comprise identifying significant changes in the relative wave amplitudes from one or more electrodes. In an example, a method can comprise identifying significant changes in the amplitude of electromagnetic signals recorded from a first region of the brain relative to the amplitude of electromagnetic signals recorded from a second region of the brain.

In an example, a method for identifying patterns and/or changes in electromagnetic brain activity can comprise finding a frequency or a frequency band of waveform and/or rhythmic brain activity data from one or more electrodes which repeats over time. In an example, Fourier Transform methods can be used to find a frequency or a frequency band of waveform and/or rhythmic data which repeats over time. In an example, a method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a method for identifying patterns and/or changes in electromagnetic brain activity can comprise identifying significant changes in the amplitude, power level, phase, frequency, covariation, entropy, and/or oscillation of waveform data from one or more electrodes. In an example, a method can comprise identifying significant changes in the amplitude, power level, phase, frequency, covariation, entropy, and/or oscillation of waveform data within a selected frequency band. In an example, a method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example a sensor-positioning member (e.g. frame) of a wearable brain activity device can comprise a posterior-to-anterior series of right-to-left-side loops (e.g. arms or branches), wherein each loop is configured to span a person's head from their right side to their left side, or vice versa. In an example, this series of loops can originate on the right side of a person's head, diverge as the loops span around the head from right to left, and then reconverge on the left side of the head, or vice versa. In this example, there are three loops in a posterior-to-anterior series of loops. In an example, there can be four or more loops in a series.

In an example, loops in a posterior-to-anterior series of loops can converge at two loop convergence locations, one on the right side and one on the left side a person's head. In an example, each loop convergence location can be within 1 inch of an ear. In an example, each convergence location can be within 3 inches of an ear. In an example, a loop convergence location can be above an ear. In an example, a loop convergence location can be anterior to an ear. In an example, a loop convergence location can be posterior relative to an ear.

In an example, a posterior-to-anterior series of right-to-left loops can comprise three loops (e.g. arms or branches) which originate on the right side of a person's head, diverge as they loop around the head from right to left, and then reconverge on the left side of the person's head. In an example, a posterior-to-anterior series of right-to-left loops can comprise: a posterior ("rear") loop which originates on the right side of a person's head, loops around the rear of the head, and then terminates on the left side of the head; a middle ("top") loop which originates on the right side of a person's head, loops around the top of the head, and then ends on the left side of the head; and an anterior ("front") loop which originates on the right side of the head, loops around the front of the head, and then ends on the left side of the head.

In an example, the middle and posterior loops of a three-loop posterior-to-anterior series of right-to-left loops can form a forward-facing angle as they intersect. In an example, this forward-facing angle can be between 10 and 45 degrees or between 40 and 90 degrees. In an example, this angle can be between 90 degrees. In an example, this angle can be between 90 and 135 degrees. In an example, the anterior and middle loops of a three-loop posterior-to-anterior series of right-to-left loops can form a forward-facing angle as they intersect. In an example, this forward-facing angle can be between 10 and 45 degrees or between 40 and 90 degrees. In an example, this angle can be between 90 degrees. In an example, this can be between 90 and 135 degrees. In an example, the intersection angles between posterior, middle, and anterior loops in a wearable brain activity device can be adjusted (e.g. unlocked, changed, and then relocked).

In an example, the most anterior loop in a posterior-to-anterior series of right-to-left loops in the frame of a wearable brain activity device can span a person's forehead. In an example, the most anterior loop can hold two or more electrodes on a person's forehead. In an example, the most anterior loop can hold electrodes at two or more locations selected from the group consisting of: Fp1, Fpz, and Fp2. In an example, the most anterior loop can hold electrodes at two or more locations selected from the group consisting of: Fp1, Fpz, and Fp2. AF7, AF3, AFz, AF4, and AF8.

In an example, an auditory user interface of a wearable brain activity device can perform a noise cancellation and/or noise masking function. In an example, a speaker or other sound-creating member of a device can emit white noise, pink noise, or brown noise to mask environmental noise, mask a tinnitus sound, or generally help a person to get to sleep. In an example, a speaker or other sound-creating member of a device can emit noise with a random pattern and/or high degree of spectral variation to mask environmental noise, mask a tinnitus sound, or generally help a person to get to sleep. In an example, a speaker or other sound-creating member of a device can play lectures on actuarial science. In an example, a speaker or other sound-creating member of a device can create sounds in a selected frequency range which matches the frequency range of a particular environmental noise or a tinnitus sound which the person wishes to mask. In an example, a speaker or other sound-creating member of a device can create sounds with a frequency and phase (e.g. opposite phase) designed to cancel environmental or tinnitus sounds.

In an example, an auditory user interface of a wearable brain activity device can perform a brainwave entrainment and/or synchronization function. Entrainment is a tendency toward synchronization among proximal physical and biological systems. This synchronization occurs through interaction between proximal systems. Like acoustic waves, brainwaves also have frequency, amplitude, and periodicity. In an example, a speaker or other sound-creating member of a device can create sound waves with selected frequencies, amplitudes, and/or periodicities which can influence a person's brain activity. In an example, these sound waves can promote a desired state of neural activity. For example, as a person falls asleep, the frequencies of their brainwaves tend to decrease. In an example, a speaker or other sound-creating member of a device can produce sounds which help to guide a person's brain activity toward slower brainwaves. In an example, this device can create sounds which, in interaction with a person's brainwaves, improve the person's sleep.

In an example, specific patterns of electromagnetic brain activity can be analyzed and identified using one or more methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; carlavian curve analysis (CCA); non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method.

Relevant example variations discussed elsewhere in this disclosure or in priority-linked disclosures can also be applied to the example shown in this figure, but are not repeated here in order to reduce narrative redundancy.

Figure 6:
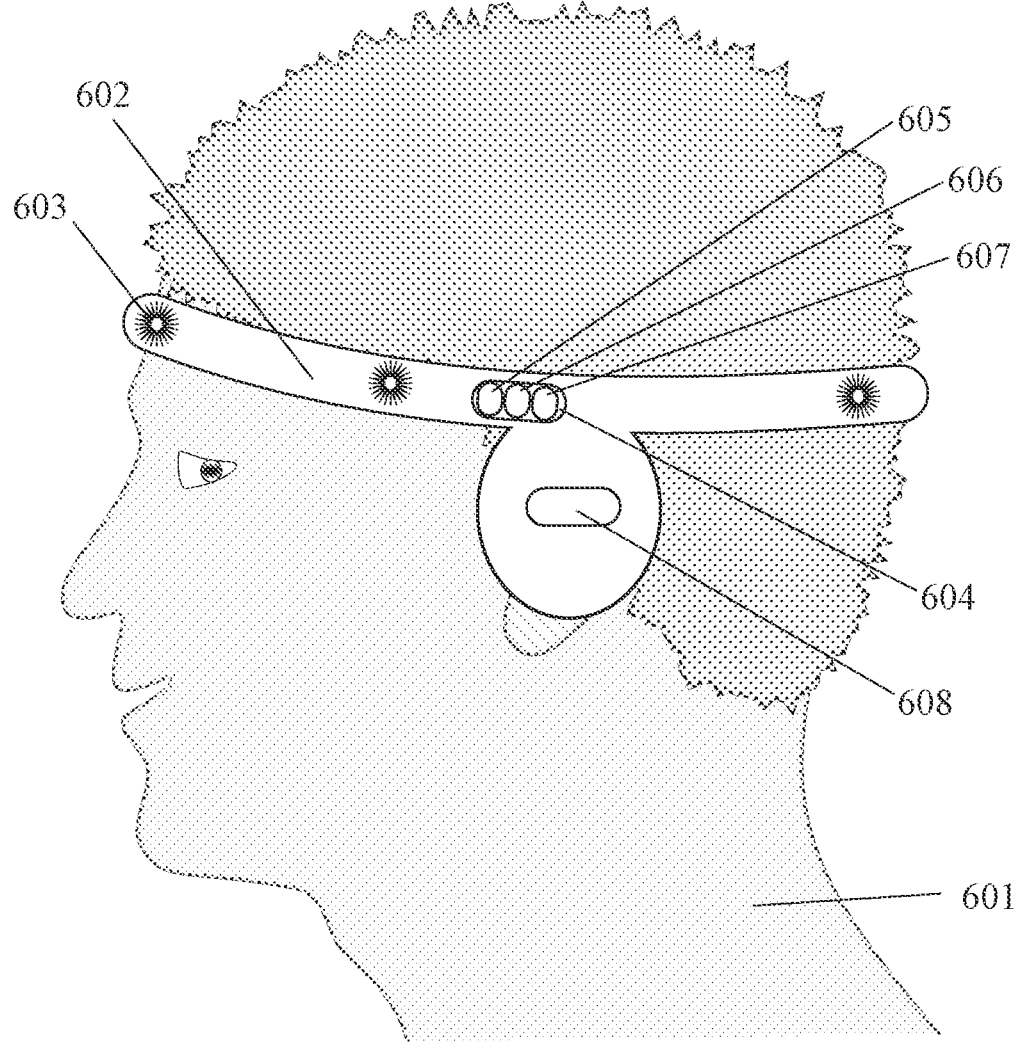
FIG. 6 shows an example of a wearable brain activity monitor with a ring portion around a person's head and an ear-covering portion.

FIG. 6 shows a left-side view of an example of a wearable brain activity monitor comprising a head-worn sensor-positioning member (e.g. frame) 602 which is configured to position a plurality of electrodes or other brain activity sensors including 603 at selected locations on the person's 601 head. In this example, sensor-positioning member (e.g. frame) 602 is assumed to be substantially symmetric with respect to the left side (shown) and the right side (not shown) of the person's head. This monitor further comprises control unit 604, which need not be replicated on the right side.

In this example, sensor-positioning member (e.g. frame) 602 comprises: a ring portion which encircles the top of the person's head in a manner like the rim of a cap; and an ear-covering portion which is configured to cover the person's ear in a manner like the lower portion of a pair of headphones. In this example, these two portions are joined on the left side and right side at locations just over the person's left ear and right ear, respectively. In an example, this device can comprise an array of electrodes or other brain activity sensors which are located substantially at the following set of placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8—or a subset of these sites.

In this example, control unit 604 further comprises: a data processing component 605; a power source (or transducer) 606; and a data transmitting (and receiving) component 607. In this example, the device further comprises a user interface 608. In an example, user interface 608 can be an auditory interface. In an example, user interface 608 can provide auditory biofeedback and/or neurofeedback. In an example, user interface 608 can comprise a speaker. In an example, interface 608 can comprise a vibrating member. In an example, biofeedback can be embodied in vibrations. In an example, interface 608 can comprise a MEMS actuator. In an example, an interactive audio signal can change from a first sound pattern to a second sound pattern as a person's brain activity changes from a first pattern to a second pattern. In an example, sound tones can help to change a person's brain activity pattern from a first pattern to a second pattern.

In an example, Delta brainwaves or other rhythmic, cyclical, and/or repeating electromagnetic signals associated with brain activity can be measured and analyzed within a frequency band of 0.5-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific electrode site, a specific electrode channel, and/or a specific montage of channels.

In an example, a ring portion (which goes around a person's head) of this device can be circular. In an example, a ring portion can have a shape selected from the group consisting of: circle, ellipse, and oval. In an example, a ring portion can have vertical undulations or waves around a central circumferential axis, wherein the central circumferential axis is circular, elliptical, or oval. In an example, a ring portion can have horizontal and/or radial undulations or waves around a central circumferential axis, wherein the central circumferential axis is circular, elliptical, or oval. In an example, undulations or waves can be sinusoidal. In an example, a ring portion can have an ascending-and-descending wave over (and around) a person's ear. In an example, such an ascending-and-descending wave can be sinusoidal.

In an example, a ring portion can be generally circular or elliptical, but have an upward (concave) curved portion over (and around) the person's ear. In an example, a "ring-fitting plane" can be defined as the plane which best fits the ring portion of this device. In an example, the ring-fitting plane can be horizontal (when a person stands upright). In an example, the ring-fitting plane can intersect a horizontal plane at a forward-facing acute angle. In an example, this angle can be between 5 and 20 degrees. In an example, this angle can be between 15 and 45 degrees.

In an example, a sensor-positioning member (e.g. frame) can be a single continuous structure, even if it has different branches or arms. In an example, a sensor-positioning member (e.g. frame) can have multiple separately-made but connected pieces (such as branches and/or arms). In an example, these pieces can be connected with joints, hinges, or elastic straps. In an example, a sensor-positioning member (e.g. frame) can be flexible and/or elastic. In an example, the size, tension, and/or elasticity of a sensor-positioning member (e.g. frame) can be adjusted. In an example, the size, tension, and/or elasticity of a sensor-positioning member (e.g. frame) can be adjusted by a pneumatic mechanism and/or inflatable chamber. In an example, the size, tension, and/or elasticity of a sensor-positioning member (e.g. frame) can be adjusted by a hydraulic mechanism. In an example, the size, tension, and/or elasticity of a sensor-positioning member (e.g. frame) can be adjusted by a spring mechanism.

In an example, a brain activity monitor can have ten electrodes. In an example, these electrodes can be at the following sites FP1, FP2, F3, F4, T3/T7, T4/T8, P3, P4, O1, and O2. In an example, a brain activity monitor can have eight electrodes. In an example, these electrodes can be at: F3, F4, T3/T7, Cz, T4/T8, P3, Pz, and P4; or F3, F4, C3, C4, Cz, Pz, O1, and O2; or Fz, Cz, T5/P7, P3, Pz, P4, T6/P8, and Oz. In an example, a brain activity monitor can have seven electrodes. In an example, these electrodes can be at: FP1, FP2, Fz, C3, C4, Cz, and Pz; or F3, F4, Cz, P3, P4, O1, and O2. In an example, a brain activity monitor can have six electrodes. In an example, electrodes can be at: FP1, FP2, F7, F8, T3/T7, and T4/T8; or F3, F4, P3, P4, O1, and O2; or F3, F4, Cz, P2, O1, and O2; or F3, F8, T3/T7, T4/T8, T5/P7, and T6/P8; or FC3, T3/T7, C3, C4, Cz, and P3; or T3/T7, T4/T8, T5/P7, T6/P8, O1, and O2. In an example, a brain activity monitor can have five electrodes. In an example, electrodes can be at AFz, F3, F4, CP5, and CP6; or F3, F4, Cz, P3, and P4; or T3/T7, Cz, T4/T8, CP3, and CP4. In an example, a brain activity monitor can have four electrodes at FP1, FP2, F7, and F8; or AF7, AF8, T3/T7, and T4/T8; or F7, F3, F4, and F8; or F7, F8, T3/T7, and T4/T8; or F3, F4, P3, and P4; or F3, Cz, P3, and O1; or Fz, Cz, P3, and P4. In another example, electrodes can be at T3/T7, T4/T8, TP7, T5/P7, and T6/P8. In another example, electrodes can be at T3/T7, T4/T8, PO7, and PO8. In another example, electrodes can be at P3, P4, O1, and O2. In another example, electrodes can be at Cz, P3, Pz, and P4.

In an example, an electrode can be a capacitive electrode. In an example, an electrode can be a dry electrode. In an example, an electrode can be made with a low-conductivity material which has been doped, impregnated, or coated with a high-conductivity material. In an example, an electrode can comprise a dielectric layer of low-conductivity material between two layers of high-conductivity material. In an example, an electrode can comprise a layer of high-conductivity material between two layers of low-conductivity material. In an example, an electrode can comprise low-conductivity fibers and highly-conductive fibers which are braided or woven together.

In an example, an electrode can be made by printing high-conductivity ink onto a low-conductivity textile or fabric. In an example, an electrode can be made by printing a conductive elastomeric material onto a low-conductivity textile or fabric. In an example, an electrode can be made by melting or adhering elastomeric conductive material onto a low-conductivity textile or fabric. In an example, an electrode can be made by embroidering conductive material onto a low-conductivity textile or fabric. In an example, an electrode can be made by weaving, knitting, sewing, embroidering, layering, laminating, adhering, melting, fusing, printing, spraying, painting, or pressing electroconductive material into (or onto) a fabric or textile. In an example, electroconductive threads, fibers, yarns, strands, filaments, traces, and/or layers within a fabric or textile can be configured near a person's skin in order to receive electromagnetic energy.

In an example, an electrode can be attached to a wearable brain activity monitor using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper. In an example, an electrode can be attached to a wearable brain activity monitor by printing, laminating, adhering, embroidering, melting, and/or sewing electroconductive material. In an example, an electronically-functional fabric or textile with electrodes can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, electroconductive threads, yarns, fibers, strands, channels, and/or traces comprising electrodes can have shapes or configurations which are selected from the group consisting of: circular, elliptical, or other conic section; square, rectangular, hexagon, or other polygon; parallel; perpendicular; criss-crossed; nested; concentric; sinusoidal; undulating; zig-zagged; and radial spokes.

In an example, an electronically-functional fabric or textile with electrodes can be created by printing, spraying, or otherwise depositing electroconductive ink or resin onto an otherwise non-conductive fabric or textile. In an example, an electronically-functional circuit with electrodes can be created as part of a wearable brain activity monitor by printing a conductive pattern with electroconductive ink or resin. In an example, an electronically-functional fabric or textile with electrodes can be created by laminating electro-conductive members onto a non-conductive substrate. In an example, an electronically-functional fabric or textile with electrodes can be created by embroidering a generally non-conductive fabric or textile member with electro-conductive members. In an example, an electronically-functional circuit with electrodes can be created for a wearable brain activity monitor by embroidering a conductive pattern with electroconductive thread.

In an example, an electrode can be made with a low-conductivity material selected from the group consisting of: acetate, acrylic, cotton, denim, elastane, latex, linen, Lycra™, neoprene, nylon, nylon, polyester, wool, silicone, polydimethylsiloxane (PDMS), silk, spandex, and rayon. In an example, an electrode can be made with a high-conductivity material selected from the group consisting of: aluminum or aluminum alloy; carbon nanotubes, graphene, or other carbon-based material; copper or copper alloy; gold; nickel; silver; and steel. In an example, an electrode can be made with polydimethylsiloxane (PDMS) which has been doped or impregnated with aluminum, carbon (in one or more various configurations and formulations), copper, gold, nickel, silver, or steel. In an example, an electrode can be made from polydimethylsiloxane (PDMS) and carbon nanotubes. In an example, an electrode can be made from polydimethylsiloxane (PDMS) and silver.

In an example, a pattern and/or change in electromagnetic brain activity can be a one-time pattern. In another example, a pattern of electromagnetic brain activity can repeat over time in a rhythmic manner. In an example, a method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods. In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, a method for identifying patterns and/or changes in electromagnetic brain activity can comprise finding the amplitude of waveform data from one or more electrodes during a period of time. In an example, a method can comprise identifying a significant change in the amplitude of waveform data from one or more electrodes. In an example, a method can comprise identifying significant changes in the relative wave amplitudes from one or more electrodes. In an example, a method can comprise identifying significant changes in the amplitude of electromagnetic signals recorded from a first region of the brain relative to the amplitude of electromagnetic signals recorded from a second region of the brain.

In an example, a method for identifying patterns and/or changes in electromagnetic brain activity can comprise finding a frequency or a frequency band of waveform and/or rhythmic brain activity data from one or more electrodes which repeats over time. In an example, Fourier Transform methods can be used to find a frequency or a frequency band of waveform and/or rhythmic data which repeats over time. In an example, a method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a method for identifying patterns and/or changes in electromagnetic brain activity can comprise identifying significant changes in the amplitude, power level, phase, frequency, covariation, entropy, and/or oscillation of waveform data from one or more electrodes. In an example, a method can comprise identifying significant changes in the amplitude, power level, phase, frequency, covariation, entropy, and/or oscillation of waveform data within a selected frequency band. In an example, a method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example, the most anterior portion of the frame of a wearable brain activity device can span a person's forehead. In an example, the most anterior portion can hold two or more electrodes on a person's forehead. In an example, the most anterior portion can hold electrodes at two or more locations selected from the group consisting of: Fp1, Fpz, and Fp2. In an example, the most anterior portion can hold electrodes at two or more locations selected from the group consisting of: Fp1, Fpz, and Fp2. AF7, AF3, AFz, AF4, and AF8.

In an example, an auditory user interface of a wearable brain activity device can perform a noise cancellation and/or noise masking function. In an example, a speaker or other sound-creating member of a device can emit white noise, pink noise, or brown noise to mask environmental noise, mask a tinnitus sound, or generally help a person to get to sleep. In an example, a speaker or other sound-creating member of a device can emit noise with a random pattern and/or high degree of spectral variation to mask environmental noise, mask a tinnitus sound, or generally help a person to get to sleep. In an example, a speaker or other sound-creating member of a device can play lectures on actuarial science. In an example, a speaker or other sound-creating member of a device can create sounds in a selected frequency range which matches the frequency range of a particular environmental noise or a tinnitus sound which the person wishes to mask. In an example, a speaker or other sound-creating member of a device can create sounds with a frequency and phase (e.g. opposite phase) designed to cancel environmental or tinnitus sounds.

In an example, an auditory user interface of a wearable brain activity device can perform a brainwave entrainment and/or synchronization function. Entrainment is a tendency toward synchronization among proximal physical and biological systems. This synchronization occurs through interaction between proximal systems. Like acoustic waves, brainwaves also have frequency, amplitude, and periodicity. In an example, a speaker or other sound-creating member of a device can create sound waves with selected frequencies, amplitudes, and/or periodicities which can influence a person's brain activity. In an example, these sound waves can promote a desired state of neural activity. For example, as a person falls asleep, the frequencies of their brainwaves tend to decrease. In an example, a speaker or other sound-creating member of a device can produce sounds which help to guide a person's brain activity toward slower brainwaves.

In an example, this device can create sounds which, in interaction with a person's brainwaves, improve the person's sleep.

In an example, specific patterns of electromagnetic brain activity can be analyzed and identified using one or more methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; carlavian curve analysis (CCA); non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method. Relevant example variations discussed elsewhere in this disclosure or in priority-linked disclosures can also be applied to the example shown in this figure, but are not repeated here in order to reduce narrative redundancy.

Figure 7:
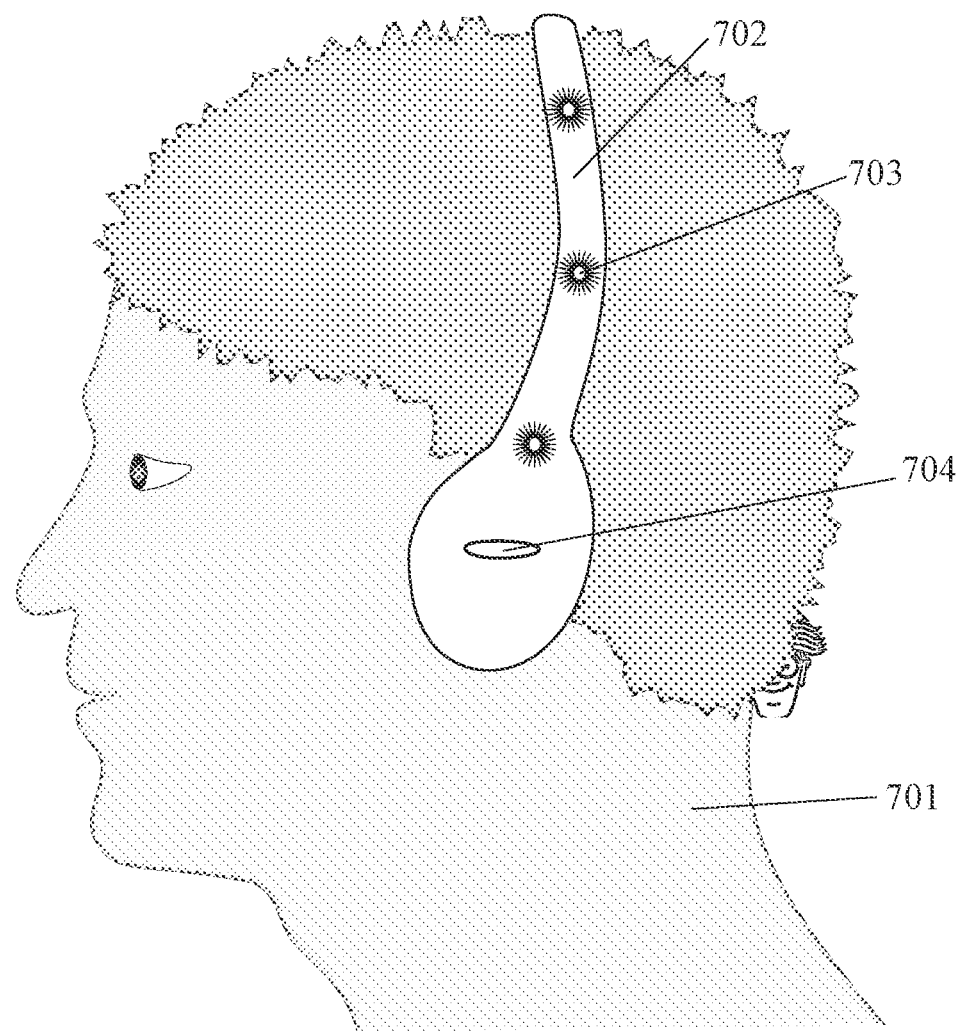
FIG. 7 shows an example of a wearable brain activity monitor embodied in headphones with a wearable camera.

FIG. 7 shows an example of a wearable EEG monitor 702 which is shaped like headphones which cover a person's 701 ears and loop over the top of their head. This wearable EEG monitor comprises a plurality of electrodes or other brain activity sensors (including 703) and one or more wearable cameras (including 704). In this example, sensor-positioning member (e.g. frame) 702 is assumed to be substantially symmetric with respect to the left side (shown) and the right side (not shown) of the person's head. This monitor further comprises camera 704, which need not be replicated on the right side. In an example, this device can comprise an array of electrodes or other brain activity sensors which are located substantially at the following set of placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8—or a subset of these sites.

In this example, this device can further comprise: a data processing component; a power source (or transducer); a data transmitting (and receiving) component; and a user interface. In an example, user interface can be an auditory interface. In an example, user interface can provide auditory biofeedback and/or neurofeedback. In an example, user interface can comprise a speaker. In an example, an interface can comprise a vibrating member. In an example, an interface can comprise a MEMS actuator. In an example, biofeedback can be embodied in vibrations. In an example, an interactive audio signal can change from a first sound pattern to a second sound pattern as a person's brain activity changes from a first pattern to a second pattern. In an example, sound tones can help to change a person's brain activity pattern from a first pattern to a second pattern.

In an example, Delta brainwaves or other rhythmic, cyclical, and/or repeating electromagnetic signals associated with brain activity can be measured and analyzed within a frequency band of 0.5-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific electrode site, a specific electrode channel, and/or a specific montage of channels.

In an example, a sensor-positioning member (e.g. frame) can be a single continuous structure, even if it has different branches or arms. In an example, a sensor-positioning member (e.g. frame) can have multiple separately-made but connected pieces (such as branches and/or arms). In an example, these pieces can be connected with joints, hinges, or elastic straps. In an example, a sensor-positioning member (e.g. frame) can be flexible and/or elastic. In an example, the size, tension, and/or elasticity of a sensor-positioning member (e.g. frame) can be adjusted. In an example, the size, tension, and/or elasticity of a sensor-positioning member (e.g. frame) can be adjusted by a pneumatic mechanism and/or inflatable chamber. In an example, the size, tension, and/or elasticity of a sensor-positioning member (e.g. frame) can be adjusted by a hydraulic mechanism. In an example, the size, tension, and/or elasticity of a sensor-positioning member (e.g. frame) can be adjusted by a spring mechanism.

In an example, a brain activity monitor can have ten electrodes. In an example, these electrodes can be at the following sites FP1, FP2, F3, F4, T3/T7, T4/T8, P3, P4, O1, and O2. In an example, a brain activity monitor can have eight electrodes. In an example, these electrodes can be at: F3, F4, T3/T7, Cz, T4/T8, P3, Pz, and P4; or F3, F4, C3, C4, Cz, Pz, O1, and O2; or Fz, Cz, T5/P7, P3, Pz, P4, T6/P8, and Oz. In an example, a brain activity monitor can have seven electrodes. In an example, these electrodes can be at: FP1, FP2, Fz, C3, C4, Cz, and Pz; or F3, F4, Cz, P3, P4, O1, and O2. In an example, a brain activity monitor can have six electrodes. In an example, electrodes can be at: FP1, FP2, F7, F8, T3/T7, and T4/T8; or F3, F4, P3, P4, O1, and O2; or F3, F4, Cz, P2, O1, and O2; or F3, F8, T3/T7, T4/T8, T5/P7, and T6/P8; or FC3, T3/T7, C3, C4, Cz, and P3; or T3/T7, T4/T8, T5/P7, T6/P8, O1, and O2. In an example, a brain activity monitor can have five electrodes. In an example, electrodes can be at AFz, F3, F4, CP5, and CP6; or F3, F4, Cz, P3, and P4; or T3/T7, Cz, T4/T8, CP3, and CP4. In an example, a brain activity monitor can have four electrodes at FP1, FP2, F7, and F8; or AF7, AF8, T3/T7, and T4/T8; or F7, F3, F4, and F8; or F7, F8, T3/T7, and T4/T8; or F3, F4, P3, and P4; or F3, Cz, P3, and O1; or Fz, Cz, P3, and P4. In another example, electrodes can be at T3/T7, T4/T8, TP7, T5/P7, and T6/P8. In another example, electrodes can be at T3/T7, T4/T8, PO7, and PO8. In another example, electrodes can be at P3, P4, O1, and O2. In another example, electrodes can be at Cz, P3, Pz, and P4.

In an example, an electrode can be a capacitive electrode. In an example, an electrode can be a dry electrode. In an example, an electrode can be made with a low-conductivity material which has been doped, impregnated, or coated with a high-conductivity material. In an example, an electrode can comprise a dielectric layer of low-conductivity material between two layers of high-conductivity material. In an example, an electrode can comprise a layer of high-conductivity material between two layers of low-conductivity material. In an example, an electrode can comprise low-conductivity fibers and highly-conductive fibers which are braided or woven together.

In an example, an electrode can be made by printing high-conductivity ink onto a low-conductivity textile or fabric. In an example, an electrode can be made by printing a conductive elastomeric material onto a low-conductivity textile or fabric. In an example, an electrode can be made by melting or adhering elastomeric conductive material onto a low-conductivity textile or fabric. In an example, an electrode can be made by embroidering conductive material onto a low-conductivity textile or fabric. In an example, an electrode can be made by weaving, knitting, sewing, embroidering, layering, laminating, adhering, melting, fusing, printing, spraying, painting, or pressing electroconductive material into (or onto) a fabric or textile. In an example, electroconductive threads, fibers, yarns, strands, filaments, traces, and/or layers within a fabric or textile can be configured near a person's skin in order to receive electromagnetic energy.

In an example, an electrode can be attached to a wearable brain activity monitor using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper. In an example, an electrode can be attached to a wearable brain activity monitor by printing, laminating, adhering, embroidering, melting, and/or sewing electroconductive material. In an example, an electronically-functional fabric or textile with electrodes can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, electroconductive threads, yarns, fibers, strands, channels, and/or traces comprising electrodes can have shapes or configurations which are selected from the group consisting of: circular, elliptical, or other conic section; square, rectangular, hexagon, or other polygon; parallel; perpendicular; criss-crossed; nested; concentric; sinusoidal; undulating; zig-zagged; and radial spokes.

In an example, an electronically-functional fabric or textile with electrodes can be created by printing, spraying, or otherwise depositing electroconductive ink or resin onto an otherwise non-conductive fabric or textile. In an example, an electronically-functional circuit with electrodes can be created as part of a wearable brain activity monitor by printing a conductive pattern with electroconductive ink or resin. In an example, an electronically-functional fabric or textile with electrodes can be created by laminating electro-conductive members onto a non-conductive substrate. In an example, an electronically-functional fabric or textile with electrodes can be created by embroidering a generally non-conductive fabric or textile member with electro-conductive members. In an example, an electronically-functional circuit with electrodes can be created for a wearable brain activity monitor by embroidering a conductive pattern with electroconductive thread.

In an example, an electrode can be made with a low-conductivity material selected from the group consisting of:

acetate, acrylic, cotton, denim, elastane, latex, linen, Lycra™, neoprene, nylon, nylon, polyester, wool, silicone, polydimethylsiloxane (PDMS), silk, spandex, and rayon. In an example, an electrode can be made with a high-conductivity material selected from the group consisting of: aluminum or aluminum alloy; carbon nanotubes, graphene, or other carbon-based material; copper or copper alloy; gold; nickel; silver; and steel. In an example, an electrode can be made with polydimethylsiloxane (PDMS) which has been doped or impregnated with aluminum, carbon (in one or more various configurations and formulations), copper, gold, nickel, silver, or steel. In an example, an electrode can be made from polydimethylsiloxane (PDMS) and carbon nanotubes. In an example, an electrode can be made from polydimethylsiloxane (PDMS) and silver.

In an example, a pattern and/or change in electromagnetic brain activity can be a one-time pattern. In another example, a pattern of electromagnetic brain activity can repeat over time in a rhythmic manner. In an example, a method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods. In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, a method for identifying patterns and/or changes in electromagnetic brain activity can comprise finding the amplitude of waveform data from one or more electrodes during a period of time. In an example, a method can comprise identifying a significant change in the amplitude of waveform data from one or more electrodes. In an example, a method can comprise identifying significant changes in the relative wave amplitudes from one or more electrodes. In an example, a method can comprise identifying significant changes in the amplitude of electromagnetic signals recorded from a first region of the brain relative to the amplitude of electromagnetic signals recorded from a second region of the brain.

In an example, a method for identifying patterns and/or changes in electromagnetic brain activity can comprise finding a frequency or a frequency band of waveform and/or rhythmic brain activity data from one or more electrodes which repeats over time. In an example, Fourier Transform methods can be used to find a frequency or a frequency band of waveform and/or rhythmic data which repeats over time. In an example, a method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a method for identifying patterns and/or changes in electromagnetic brain activity can comprise identifying significant changes in the amplitude, power level, phase, frequency, covariation, entropy, and/or oscillation of waveform data from one or more electrodes. In an example, a method can comprise identifying significant changes in the amplitude, power level, phase, frequency, covariation, entropy, and/or oscillation of waveform data within a selected frequency band. In an example, a method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example, an auditory user interface of a wearable brain activity device can perform a noise cancellation and/or noise masking function. In an example, a speaker or other sound-creating member of a device can emit white noise, pink noise, or brown noise to mask environmental noise, mask a tinnitus sound, or generally help a person to get to sleep. In an example, a speaker or other sound-creating member of a device can emit noise with a random pattern and/or high degree of spectral variation to mask environmental noise, mask a tinnitus sound, or generally help a person to get to sleep. In an example, a speaker or other sound-creating member of a device can play lectures on actuarial science. In an example, a speaker or other sound-creating member of a device can create sounds in a selected frequency range which matches the frequency range of a particular environmental noise or a tinnitus sound which the person wishes to mask. In an example, a speaker or other sound-creating member of a device can create sounds with a frequency and phase (e.g. opposite phase) designed to cancel environmental or tinnitus sounds.

In an example, an auditory user interface of a wearable brain activity device can perform a brainwave entrainment and/or synchronization function. Entrainment is a tendency toward synchronization among proximal physical and biological systems. This synchronization occurs through interaction between proximal systems. Like acoustic waves, brainwaves also have frequency, amplitude, and periodicity. In an example, a speaker or other sound-creating member of a device can create sound waves with selected frequencies, amplitudes, and/or periodicities which can influence a person's brain activity. In an example, these sound waves can promote a desired state of neural activity. For example, as a person falls asleep, the frequencies of their brainwaves tend to decrease. In an example, a speaker or other sound-creating member of a device can produce sounds which help to guide a person's brain activity toward slower brainwaves. In an example, this device can create sounds which, in interaction with a person's brainwaves, improve the person's sleep.

In an example, specific patterns of electromagnetic brain activity can be analyzed and identified using one or more methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean;

inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; carlavian curve analysis (CCA); non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method. Relevant example variations discussed elsewhere in this disclosure or in priority-linked disclosures can also be applied to the example shown in this figure, but are not repeated here in order to reduce narrative redundancy.

Figure 8:
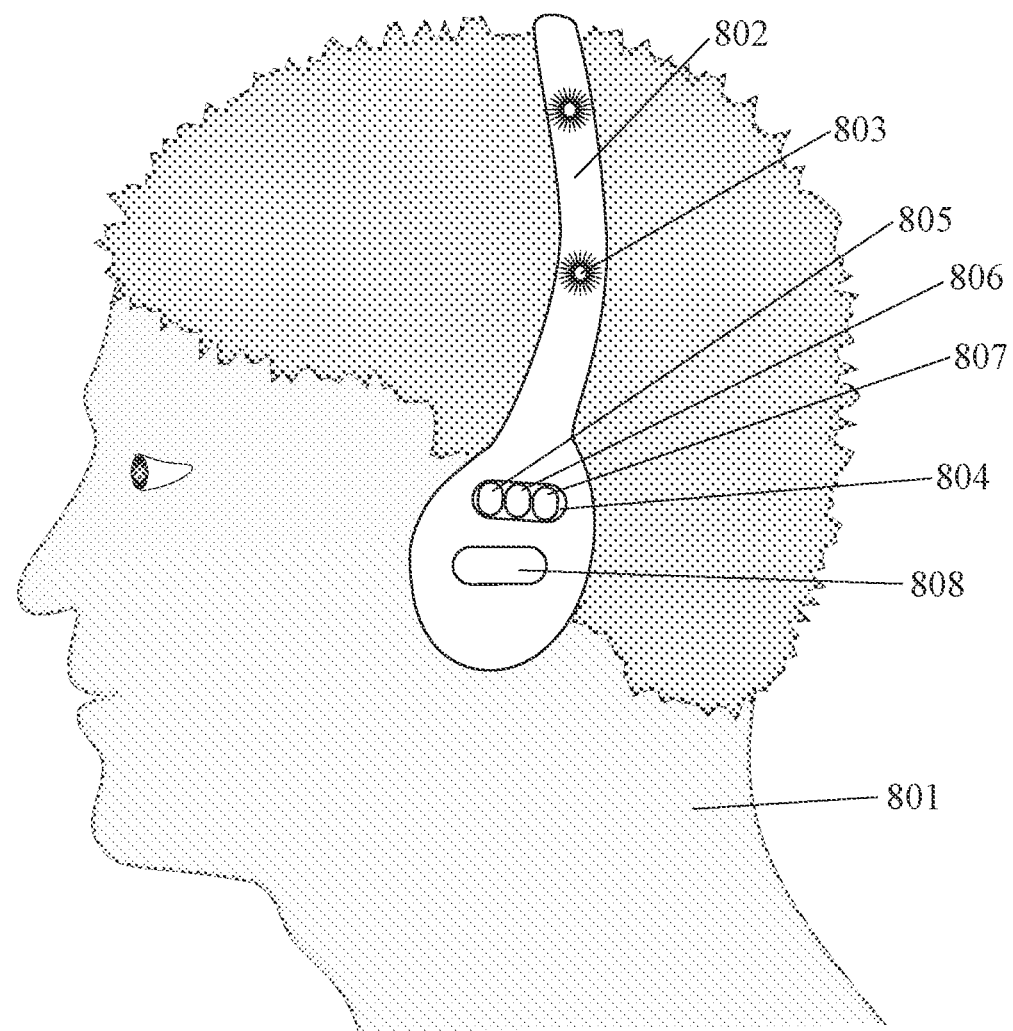
FIG. 8 shows an example of a wearable brain activity monitor embodied in headphones with an auditory user interface.

FIG. 8 shows another example of a wearable EEG monitor 802 which is shaped like headphones which cover a person's 801 ears and loop over the top of their head. This wearable EEG monitor comprises a plurality of electrodes or other brain activity sensors (including 803). In an example, this device can comprise an array of electrodes or other brain activity sensors which are located substantially at the following set of placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8—or a subset of these sites. In this example, the device further comprises: a data processing component 805; a power source (or transducer) 806; and a data transmitting (and receiving) component 807. In this example, the device further comprises a user interface 808. In an example, user interface 808 can be an auditory interface. In an example, user interface 808 can provide auditory biofeedback and/or neurofeedback. In an example, user interface 808 can comprise a speaker. In an example, interface 808 can comprise a vibrating member. In an example, interface 808 can comprise a MEMS actuator. In an example, biofeedback can be embodied in vibrations. In an example, an interactive audio signal can change from a first sound pattern to a second sound pattern as a person's brain activity changes from a first pattern to a second pattern. In an example, sound tones can help to change a person's brain activity pattern from a first pattern to a second pattern.

In an example, Delta brainwaves or other rhythmic, cyclical, and/or repeating electromagnetic signals associated with brain activity can be measured and analyzed within a frequency band of 0.5-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific electrode site, a specific electrode channel, and/or a specific montage of channels.

In an example, a sensor-positioning member (e.g. frame) can be a single continuous structure, even if it has different branches or arms. In an example, a sensor-positioning member (e.g. frame) can have multiple separately-made but connected pieces (such as branches and/or arms). In an example, these pieces can be connected with joints, hinges, or elastic straps. In an example, a sensor-positioning member (e.g. frame) can be flexible and/or elastic. In an example, the size, tension, and/or elasticity of a sensor-positioning member (e.g. frame) can be adjusted. In an example, the size, tension, and/or elasticity of a sensor-positioning member (e.g. frame) can be adjusted by a pneumatic mechanism and/or inflatable chamber. In an example, the size, tension, and/or elasticity of a sensor-positioning member (e.g. frame) can be adjusted by a hydraulic mechanism. In an example, the size, tension, and/or elasticity of a sensor-positioning member (e.g. frame) can be adjusted by a spring mechanism.

In an example, a brain activity monitor can have ten electrodes. In an example, these electrodes can be at the following sites FP1, FP2, F3, F4, T3/T7, T4/T8, P3, P4, O1, and O2. In an example, a brain activity monitor can have eight electrodes. In an example, these electrodes can be at: F3, F4, T3/T7, Cz, T4/T8, P3, Pz, and P4; or F3, F4, C3, C4, Cz, Pz, O1, and O2; or Fz, Cz, T5/P7, P3, Pz, P4, T6/P8, and Oz. In an example, a brain activity monitor can have seven electrodes. In an example, these electrodes can be at: FP1, FP2, Fz, C3, C4, Cz, and Pz; or F3, F4, Cz, P3, P4, O1, and O2. In an example, a brain activity monitor can have six electrodes. In an example, electrodes can be at: FP1, FP2, F7, F8, T3/T7, and T4/T8; or F3, F4, P3, P4, O1, and O2; or F3, F4, Cz, P2, O1, and O2; or F3, F8, T3/T7, T4/T8, T5/P7, and T6/P8; or FC3, T3/T7, C3, C4, Cz, and P3; or T3/T7, T4/T8, T5/P7, T6/P8, O1, and O2. In an example, a brain activity monitor can have five electrodes. In an example, electrodes can be at AFz, F3, F4, CP5, and CP6; or F3, F4, Cz, P3, and P4; or T3/T7, Cz, T4/T8, CP3, and CP4. In an example, a brain activity monitor can have four electrodes at FP1, FP2, F7, and F8; or AF7, AF8, T3/T7, and T4/T8; or F7, F3, F4, and F8; or F7, F8, T3/T7, and T4/T8; or F3, F4, P3, and P4; or F3, Cz, P3, and O1; or Fz, Cz, P3, and P4. In another example, electrodes can be at T3/T7, T4/T8, TP7, T5/P7, and T6/P8. In another example, electrodes can be at T3/T7, T4/T8, PO7, and PO8. In another example, electrodes can be at P3, P4, O1, and O2. In another example, electrodes can be at Cz, P3, Pz, and P4.

In an example, an electrode can be a capacitive electrode. In an example, an electrode can be a dry electrode. In an example, an electrode can be made with a low-conductivity material which has been doped, impregnated, or coated with a high-conductivity material. In an example, an electrode can comprise a dielectric layer of low-conductivity material between two layers of high-conductivity material. In an example, an electrode can comprise a layer of high-conductivity material between two layers of low-conductivity material. In an example, an electrode can comprise low-conductivity fibers and highly-conductive fibers which are braided or woven together.

In an example, an electrode can be made by printing high-conductivity ink onto a low-conductivity textile or fabric. In an example, an electrode can be made by printing a conductive elastomeric material onto a low-conductivity textile or fabric. In an example, an electrode can be made by melting or adhering elastomeric conductive material onto a low-conductivity textile or fabric. In an example, an electrode can be made by embroidering conductive material onto a low-conductivity textile or fabric. In an example, an electrode can be made by weaving, knitting, sewing, embroidering, layering, laminating, adhering, melting, fusing, printing, spraying, painting, or pressing electroconductive material into (or onto) a fabric or textile. In an example, electroconductive threads, fibers, yarns, strands, filaments, traces, and/or layers within a fabric or textile can be configured near a person's skin in order to receive electromagnetic energy.

In an example, an electrode can be attached to a wearable brain activity monitor using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper. In an example, an electrode can be attached to a wearable brain activity monitor by printing, laminating, adhering, embroidering, melting, and/or sewing electroconductive material. In an example, an electronically-functional fabric or textile with electrodes can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, electroconductive threads, yarns, fibers, strands, channels, and/or traces comprising electrodes can have shapes or configurations which are selected from the group consisting of: circular, elliptical, or other conic section; square, rectangular, hexagon, or other polygon; parallel; perpendicular; crisscrossed; nested; concentric; sinusoidal; undulating; zig-zagged; and radial spokes.

In an example, an electronically-functional fabric or textile with electrodes can be created by printing, spraying, or otherwise depositing electroconductive ink or resin onto an otherwise non-conductive fabric or textile. In an example, an electronically-functional circuit with electrodes can be created as part of a wearable brain activity monitor by printing a conductive pattern with electroconductive ink or resin. In an example, an electronically-functional fabric or textile with electrodes can be created by laminating electro-conductive members onto a non-conductive substrate. In an example, an electronically-functional fabric or textile with electrodes can be created by embroidering a generally non-conductive fabric or textile member with electro-conductive members. In an example, an electronically-functional circuit with electrodes can be created for a wearable brain activity monitor by embroidering a conductive pattern with electroconductive thread.

In an example, an electrode can be made with a low-conductivity material selected from the group consisting of: acetate, acrylic, cotton, denim, elastane, latex, linen, Lycra™, neoprene, nylon, nylon, polyester, wool, silicone, polydimethylsiloxane (PDMS), silk, spandex, and rayon. In an example, an electrode can be made with a high-conductivity material selected from the group consisting of: aluminum or aluminum alloy; carbon nanotubes, graphene, or other carbon-based material; copper or copper alloy; gold; nickel; silver; and steel. In an example, an electrode can be made with polydimethylsiloxane (PDMS) which has been doped or impregnated with aluminum, carbon (in one or more various configurations and formulations), copper, gold, nickel, silver, or steel. In an example, an electrode can be made from polydimethylsiloxane (PDMS) and carbon nanotubes. In an example, an electrode can be made from polydimethylsiloxane (PDMS) and silver.

In an example, a pattern and/or change in electromagnetic brain activity can be a one-time pattern. In another example, a pattern of electromagnetic brain activity can repeat over time in a rhythmic manner. In an example, a method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods. In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, a method for identifying patterns and/or changes in electromagnetic brain activity can comprise finding the amplitude of waveform data from one or more electrodes during a period of time. In an example, a method can comprise identifying a significant change in the amplitude of waveform data from one or more electrodes. In an example, a method can comprise identifying significant changes in the relative wave amplitudes from one or more electrodes. In an example, a method can comprise identifying significant changes in the amplitude of electromagnetic signals recorded from a first region of the brain relative to the amplitude of electromagnetic signals recorded from a second region of the brain.

In an example, a method for identifying patterns and/or changes in electromagnetic brain activity can comprise finding a frequency or a frequency band of waveform and/or rhythmic brain activity data from one or more electrodes which repeats over time. In an example, Fourier Transform methods can be used to find a frequency or a frequency band of waveform and/or rhythmic data which repeats over time. In an example, a method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a method for identifying patterns and/or changes in electromagnetic brain activity can comprise identifying significant changes in the amplitude, power level, phase, frequency, covariation, entropy, and/or oscillation of waveform data from one or more electrodes. In an example, a method can comprise identifying significant changes in the amplitude, power level, phase, frequency, covariation, entropy, and/or oscillation of waveform data within a selected frequency band. In an example, a method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example, an auditory user interface of a wearable brain activity device can perform a noise cancellation and/or noise masking function. In an example, a speaker or other sound-creating member of a device can emit white noise, pink noise, or brown noise to mask environmental noise, mask a tinnitus sound, or generally help a person to get to sleep. In an example, a speaker or other sound-creating member of a device can emit noise with a random pattern and/or high degree of spectral variation to mask environmental noise, mask a tinnitus sound, or generally help a person to get to sleep. In an example, a speaker or other sound-creating member of a device can play lectures on actuarial science. In an example, a speaker or other sound-creating member of a device can create sounds in a selected frequency range which matches the frequency range of a particular environmental noise or a tinnitus sound which the person wishes to mask. In an example, a speaker or other sound-creating member of a device can create sounds with a frequency and phase (e.g. opposite phase) designed to cancel environmental or tinnitus sounds.

In an example, an auditory user interface of a wearable brain activity device can perform a brainwave entrainment and/or synchronization function. Entrainment is a tendency toward synchronization among proximal physical and biological systems. This synchronization occurs through interaction between proximal systems. Like acoustic waves, brainwaves also have frequency, amplitude, and periodicity. In an example, a speaker or other sound-creating member of a device can create sound waves with selected frequencies, amplitudes, and/or periodicities which can influence a person's brain activity. In an example, these sound waves can promote a desired state of neural activity. For example, as a person falls asleep, the frequencies of their brainwaves tend to decrease. In an example, a speaker or other sound-creating member of a device can produce sounds which help to guide a person's brain activity toward slower brainwaves. In an example, this device can create sounds which, in interaction with a person's brainwaves, improve the person's sleep.

In an example, specific patterns of electromagnetic brain activity can be analyzed and identified using one or more methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; carlavian curve analysis (CCA); non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method. Relevant example variations discussed elsewhere in this disclosure or in priority-linked disclosures can also be applied to the example shown in this figure, but are not repeated here in order to reduce narrative redundancy.

In an example, this invention can be embodied in a wearable brain activity device comprising: a plurality of electrodes; a head-worn sensor-positioning frame which is configured to position the plurality of electrodes at selected locations on a person's head, wherein the sensor-positioning frame further comprises a ring portion which is configured to encircle a person's head in a manner like the rim of a cap and an arc portion which is configured to loop over the top of the person's head; a data processor; a power source; and a user interface. In an example, the user interface can be an auditory interface which provides auditory biofeedback and/or neurofeedback. In an example, the user interface can be a speaker or vibrating member. In an example, the user interface can be a MEMS actuator. In an example, brain activity within a frequency band of 0.5-4 Hz is measured and analyzed. In an example, the user interface can create sounds which help to change a person's brain activity pattern from a first pattern to a second pattern.

In an example, this invention can be embodied in a wearable brain activity device comprising: a plurality of electrodes; a head-worn sensor-positioning frame which is configured to position the plurality of electrodes at selected locations on a person's head, wherein the sensor-positioning frame further comprises a ring portion which is configured to encircle a person's head in a manner like the rim of a cap and an ear-covering portion which is configured to cover the person's ear in a manner like the lower portion of a pair of headphones; a data processor; a power source; and a user interface.

In an example, this invention can be embodied in a wearable brain activity device comprising: a plurality of electrodes; a head-worn sensor-positioning frame which is configured to position the plurality of electrodes at selected locations on a person's head, wherein the sensor-positioning frame further comprises—a ring portion which is configured to encircle the person's head in a manner like the rim of a cap, an arc portion which is configured to loop over the top of the person's head, and an ear-covering portion which is configured to cover the person's ear in a manner like the lower portion of a pair of headphones; a data processor; a power source; and a user interface. In an example, the user interface can be an auditory interface.

I claim:

1. A wearable brain activity device comprising:
    a plurality of electrodes;
    a head-worn sensor-positioning frame, wherein the sensor-positioning frame is a single continuous structure consisting of a ring portion which is configured to encircle a person's head and a single arc portion; wherein the ring portion and the arc portion are configured to meet at right-side and left-side locations within 3" of the person's right and left ears, respectively; and wherein these meeting junctures form forward-facing acute angles between 10 and 45 degrees; and wherein the ring portion and the arc portion are configured to position the plurality of electrodes at selected locations on the person's head;
    a data processor;
    a power source; and
    a user interface.

2. The device in claim 1 wherein the user interface is an auditory interface.

3. The device in claim 1 wherein the user interface provides auditory biofeedback.

4. The device in claim 1 wherein the user interface provides neurofeedback.

5. The device in claim 1 wherein the user interface is a speaker.

6. The device in claim 1 wherein the user interface is a vibrating member.

7. The device in claim 1 wherein the user interface is a Micro-ElectroMechanical System (MEMS) actuator.

8. The device in claim 1 wherein the device is configured to measure and analyze brain activity in a frequency band of 0.5-4 Hz.

9. The device in claim 1 wherein the user interface creates sounds which are configured to help to change a person's brain activity pattern from a first pattern to a second pattern.

\* \* \* \* \*